(12) United States Patent
Phillips et al.

(10) Patent No.: US 9,487,408 B2
(45) Date of Patent: Nov. 8, 2016

(54) REDUCING ALUMINOSILICATE SCALE IN THE BAYER PROCESS

(75) Inventors: Everett C. Phillips, Batavia, IL (US); Timothy La, Kardinya (AU); Kailas B. Sawant, Aurora, IL (US)

(73) Assignee: Nalco Company, Naperville, IL (US)

( * ) Notice: Subject to any disclaimer, the term of this patent is extended or adjusted under 35 U.S.C. 154(b) by 253 days.

(21) Appl. No.: 13/403,282

(22) Filed: Feb. 23, 2012

(65) Prior Publication Data

US 2012/0148462 A1    Jun. 14, 2012

Related U.S. Application Data

(63) Continuation-in-part of application No. 12/567,116, filed on Sep. 25, 2009, now Pat. No. 8,545,776, and a continuation-in-part of application No. 13/035,124, filed on Feb. 25, 2011, now Pat. No. 8,889,096.

(51) Int. Cl.
| | |
|---|---|
| *C01F 7/02* | (2006.01) |
| *C01F 7/47* | (2006.01) |
| *C01F 7/06* | (2006.01) |

(52) U.S. Cl.
CPC .............. *C01F 7/47* (2013.01); *C01F 7/0606* (2013.01); *C01F 7/0633* (2013.01)

(58) Field of Classification Search
None
See application file for complete search history.

(56) References Cited

U.S. PATENT DOCUMENTS

| | | |
|---|---|---|
| 5,118,484 A | 6/1992 | The et al. |
| 5,314,626 A | 5/1994 | Dimas |
| 5,415,782 A | 5/1995 | Dimas |
| 5,650,072 A | 7/1997 | McClain et al. |
| 6,086,771 A | 7/2000 | Selvarajan et al. |
| 6,551,515 B1 | 4/2003 | Bruening et al. |
| 6,569,908 B2 | 5/2003 | Noguchi et al. |
| 6,808,768 B2 | 10/2004 | Satou et al. |
| 6,814,873 B2 | 11/2004 | Spitzer et al. |
| 6,867,318 B1 | 3/2005 | Cui |
| 7,390,415 B2 | 6/2008 | Spitzer et al. |
| 7,442,755 B2 | 10/2008 | Spitzer et al. |
| 7,763,698 B2 | 7/2010 | Spitzer et al. |
| 2004/0011744 A1 | 1/2004 | Spitzer et al. |
| 2004/0162406 A1 | 8/2004 | Spitzer et al. |
| 2005/0010008 A2 | 1/2005 | Spitzer et al. |
| 2005/0231436 A1 | 10/2005 | McLean et al. |
| 2007/0178041 A1 | 8/2007 | Tizon et al. |
| 2007/0231249 A1 | 10/2007 | Batllo et al. |
| 2008/0111103 A1 | 5/2008 | Heitner |
| 2009/0008335 A1 | 1/2009 | Flocken et al. |
| 2009/0026064 A1 | 1/2009 | McCausland et al. |
| 2010/0256317 A1 | 10/2010 | Spitzer et al. |
| 2011/0076209 A1 | 3/2011 | La et al. |
| 2011/0212006 A1 | 9/2011 | La et al. |

FOREIGN PATENT DOCUMENTS

| | | |
|---|---|---|
| CN | 101747361 A | 6/2010 |
| EP | 2214632 A2 | 8/2010 |
| FR | 2922760 A1 | 5/2009 |
| WO | 96/06043 | 2/1996 |
| WO | 97/41065 | 11/1997 |
| WO | 97/41075 | 11/1997 |
| WO | 2002070411 | 9/2002 |
| WO | WO 02/085486 A1 | 10/2002 |
| WO | WO 03/002057 A2 | 1/2003 |
| WO | 2006003470 | 1/2006 |
| WO | 2008017109 | 2/2008 |
| WO | 2008045677 | 4/2008 |
| WO | WO 2009/056778 A2 | 5/2009 |
| WO | WO 2009/056778 A3 | 5/2009 |

OTHER PUBLICATIONS

Robson, Product Silica Control Options, Light Metals (1998), pp. 87-94.
The, A Novel Approach to Post-Desilicating Bayer Process Liquor, Light Metals (1998), pp. 117-122.
Spitzer et al., Reagents for the elimination of sodalite scaling, Light Metals (2005), pp. 183-88.
Spitzer et al., Max HT Sodalite Scale Inhibitor: Plant Experience and Impact on the Process, Light Metals (2008), pp. 57-62.
Oliveira et al., Performance Appraisal of Evaporation System with Scale Inhibitor Application in Alnorte Plant, Light Metals (2008), pp. 133-136.
International Search Report for PCT/US2010/049555 (parent PCT application).
International Search Report for PCT/2012/024099 (parent PCT application).
Deoliveira et al., "Ethylenediamine attached to silica as an efficient, reusable nanocatalyst for the addition of nitromethane to cyclopentenone." *J. of Mol. Catalysis*, A: Chemical 271, Feb. 25, 2007, pp. 63-69.
Sales et al., "Interaction of divalent copper with two diaminealkyl hexagonal mesoporous silicas evaluated by adsorption and thermochemical data," *Surface Science*, 590, Jul. 6, 2005, pp. 51-62.
Sales et al., "Epoxide silylant agent ethylenediamine reaction product anchored on silica gel—thermodynamics of cation—nitrogen interaction at solid/liquid interface," *J. of Non-Crystalline Solids*, 330, Feb. 11, 2003, pp. 142-149.

*Primary Examiner* — Robert Xu
(74) *Attorney, Agent, or Firm* — Leydig, Voit & Mayer, Ltd.

(57) ABSTRACT

The invention provides a method of inhibiting the accumulation of DSP scale in the liquor circuit of Bayer process equipment. The method includes adding one or more particular silane based small molecules to the liquor fluid circuit. These scale inhibitors reduce DSP scale formation and thereby increase fluid throughput, increase the amount of time Bayer process equipment can be operational and reduce the need for expensive and dangerous acid washes of Bayer process equipment. As a result, the invention provides a significant reduction in the total cost of operating a Bayer process.

12 Claims, No Drawings

REDUCING ALUMINOSILICATE SCALE IN THE BAYER PROCESS

CROSS-REFERENCE TO RELATED APPLICATIONS

This application is a continuation-in-part application of U.S. patent application Ser. No. 12/567,116, filed on Sep. 25, 2009, now U.S. Pat. No. 8,545,776 and Ser. No. 13/035,124, filed on Feb. 25, 2011, from which filing priority is hereby claimed and the disclosures of which are hereby incorporated by reference.

STATEMENT REGARDING FEDERALLY SPONSORED RESEARCH OR DEVELOPMENT

Not Applicable.

BACKGROUND OF THE INVENTION

This invention relates to compositions of matter and methods of using them to treat scale in various industrial process streams, in particular certain silane based small molecules that have been found to be particularly effective in treating aluminosilicate scale in a Bayer process stream.

As described among other places in U.S. Pat. No. 6,814,873 the contents of which are incorporated by reference in their entirety, the Bayer process is used to manufacture alumina from Bauxite ore. The process uses caustic solution to extract soluble alumina values from the bauxite. After dissolution of the alumina values from the bauxite and removal of insoluble waste material from the process stream the soluble alumina is precipitated as solid alumina trihydrate. The remaining caustic solution known as "liquor" and/or "spent liquor" is then recycled back to earlier stages in the process and is used to treat fresh bauxite. It thus forms a fluid circuit. For purposes of this application, this description defines the term "liquor." The recycling of liquor within the fluid circuit however has its own complexities.

Bauxite often contains silica in various forms and amounts. Some of the silica is unreactive so it does not dissolve and remains as solid material within the Bayer circuit. Other forms of silica (for example clays) are reactive and dissolve in caustic when added into Bayer process liquors, thus increasing the silica concentration in the liquor. As liquor flows repeatedly through the circuit of the Bayer process, the concentration of silica in the liquor further increases, eventually to a point where it reacts with aluminum and soda to form insoluble aluminosilicate particles. Aluminosilicate solid is observed in at least two forms, sodalite and cancrinite. These and other forms of aluminosilicate are commonly referred to, and for the purposes of this application define, the terms "desilication, product" or "DSP."

DSP can have a formula of $3(Na_2O.Al_2O_3.2SiO_2.0-2H_2O).2NaX$ where X represents $OH^-$, $Cl^-$, $CO_3^{2-}$, $SO_4^{2-}$. Because DSP has an inverse solubility (precipitation increases at higher temperatures) and it can precipitate as fine scales of hard insoluble crystalline solids, its accumulation in Bayer process equipment is problematic. As DSP accumulates in Bayer process pipes, vessels, heat transfer equipment, and other process equipment, it forms flow bottlenecks and obstructions and can adversely affect liquor throughput. In addition because of its thermal conductivity properties, DSP scale on heat exchanger surfaces reduce the efficiency of heat exchangers.

These adverse effects are typically managed through a descaling regime, which involves process equipment being taken off line and the scale being physically or chemically treated and removed. A consequence of this type of regime is significant and regular periods of down-time for critical equipment. Additionally as part of the descaling process the use of hazardous concentrated acids such as sulfuric acid are often employed and this constitutes an undesirable safety hazard.

Another way Bayer process operators manage the buildup of silica concentration in the liquor is to deliberately precipitate DSP as free crystals rather than as scale. Typically a "desilication" step in the Bayer process is used to reduce the concentration of silica in solution by precipitation of silica as DSP, as a free precipitate. While such desilication reduces the overall silica concentration within the liquor, total elimination of all silica from solution is impractical and changing process conditions within various parts of the circuit (for example within heat exchangers) can lead to changes in the solubility of DSP, resulting in consequent precipitation as scale.

Previous attempts at controlling and/or reducing DSP scale in the Bayer process have included adding polymer materials containing three alkyloxy groups bonded to one silicon atom as described in U.S. Pat. No. 6,814,873 B2, US published applications 2004/0162406 A1, 2004/0011744 A1, 2005/0010008 A2, international published application WO 2008/045677 A1, and published article *Max HT™ Sodalite Scale Inhibitor: Plant Experience and Impact on the Process*, by Donald Spitzer et. al., Pages 57-62, *Light Metals* 2008, (2008) all of whose contents are incorporated by reference in their entirety.

Manufacturing and use of these trialkoxysilane-grafted polymers however can involve unwanted degrees of viscosity, making handling and dispersion of the polymer through the Bayer process liquor problematic. Other previous attempts to address foulant buildup are described in U.S. Pat. Nos. 5,650,072 and 5,314,626, both of which are incorporated by reference in their entirety.

Thus while a range of methods are available to Bayer process operators to manage and control DSP scale formation, there is a clear need for, and utility in, an improved method of preventing or reducing DSP scale formation on Bayer process equipment. The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

BRIEF SUMMARY OF THE INVENTION

At least one embodiment is directed towards a method for reducing siliceous scale in a Bayer process comprising the step of adding to a Bayer liquor an aluminosilicate scale inhibiting amount of reaction product between an amine-containing molecule and an amine-reactive molecule containing at least one amine-reactive group per molecule and at least one $—Si(OR)_n$ group per molecule, where n=1, 2, or 3, and R=H, C1-C12 Alkyl, Aryl, Na, K, Li, or $NH_4$, or a mixture of such reaction products.

Another embodiment is directed towards a method for reducing siliceous scale in a Bayer process comprising the step of adding to a Bayer liquor an efficacious amount of a reaction product between: 1) an amine-containing small molecule, and 2) an amine-reactive small molecule containing at least one amine-reactive group per molecule and at least one —Si(OR)$_n$ group per molecule, where n=1, 2, or 3, and R=H, C1-C12 Alkyl, Aryl, Na, K, Li, or NH$_4$, or a mixture of such reaction products, and 3) a non-polymeric amine reactive hydrophobic hydrocarbon.

At least one embodiment is directed towards a method of reducing DSP in a Bayer process comprising the step of adding to the Bayer process stream an aluminosilicate scale inhibiting amount of a mixture of products as defined above.

In one embodiment, the disclosure is directed to a method for the reduction of aluminosilicate-containing scale in a Bayer process. The method comprises adding to a Bayer process stream an aluminosilicate scale inhibiting amount of a composition comprising a non-polymeric molecule. The non-polymeric molecule comprises at least three components. A first component of the at least three components has a general formula:

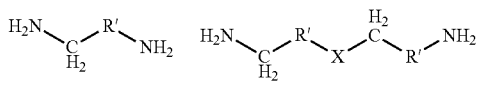

where R'=CH$_2$, or CH$_2$—CH$_2$; and X=NH$_2$, NH$_2$—R'—NH$_2$, or NH$_2$—R'—NH$_2$—R'—NH$_2$. A second component of the at least three components is 3-glycidoxypropyltrimethyloxysilane. A third component of the at least three components is 2-ethylhexylglycidyl ether. Synthesis of the non-polymeric molecule proceeds by combining the first component with the second component at a reactive hydrogen of the first component to form an intermediate, and then combining the intermediate with the third component to form the non-polymeric molecule.

DETAILED DESCRIPTION OF THE INVENTION

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description of the Invention," relates to a requirement of the United States Patent Office, and does not imply, nor should be inferred to limit the subject matter disclosed herein.

For purposes of this application the definition of these terms is as follows:

"Polymer" means a chemical compound comprising essentially repeating structural units each containing two or more atoms. While many polymers have large molecular weights of greater than 500, some polymers such as polyethylene can have molecular weights of less than 500. Polymer includes copolymers and homo polymers.

"Small molecule" means a chemical compound comprising essentially non-repeating structural units. Because an oligomer (with more than 10 repeating units) and a polymer are essentially comprised of repeating structural units, they are not small molecules. Small molecules can have molecular weights above and below 500. The terms "small molecule" and "polymer" are mutually exclusive.

"Foulant" means a material deposit that accumulates on equipment during the operation of a manufacturing and/or chemical process which may be unwanted and which may impair the cost and/or efficiency of the process. DSP is a type of foulant.

"Amine" means a molecule containing one or more nitrogen atoms and having at least one secondary amine or primary amine group. By this definition, monoamines such as dodecylamine, diamines such as hexanediamine, triamines such as diethylene triamine, and tetraethylene pentamine are all amines, as well as hexamine diamine.

"GPS" is 3-glycidoxypropyltrimethoxysilane.

"Alkyloxy" means having the structure of OX where X is a hydrocarbon and O is oxygen. It can also be used interchangeably with the term "alkoxy". Typically in this application, the oxygen is bonded both to the X group as well as to a silicon atom of the small molecule. When X is C$_1$ the alkyloxy group consists of a methyl group bonded to the oxygen atom. When X is C$_2$ the alkyloxy group consists of an ethyl group bonded to the oxygen atom. When X is C$_3$ the alkyloxy group consists of a propyl group bonded to the oxygen atom. When X is C4 the alkyloxy group consists of a butyl group bonded to the oxygen atom. When X is C$_5$ the alkyloxy group consists of a pentyl group bonded to the oxygen atom. When X is C$_6$ the alkyloxy group consists of a hexyl group bonded to the oxygen atom.

"Monoalkyloxy" means that attached to a silicon atom is one alkyloxy group.

"Dialkyloxy" means that attached to a silicon atom are two alkyloxy groups.

"Trialkyloxy" means that attached to a silicon atom are three alkyloxy groups.

"Synthetic Liquor" or "Synthetic Spent Liquor" is a laboratory created liquid used for experimentation whose composition in respect to alumina, soda, and caustic corresponds with the liquor produced by recycling through the Bayer process.

"Bayer Liquor" is actual liquor that has run through a Bayer process in an industrial facility.

"Alkylamine" means entities where hydrogen bonds of ammonia are substituted with alkyl groups.

"Alkylene" means an unsaturated, aliphatic hydrocarbon with one or more carbon-carbon double bonds.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology*, 5th Edition, (2005), (Published by Wiley, John & Sons, Inc.) this definition shall control how the term is to be defined in the claims.

In the Bayer process for manufacturing alumina, bauxite ore passes through a grinding stage and alumina, together with some impurities including silica, are dissolved in added liquor. The mixture then typically passes through a desilication stage where silica is deliberately precipitated as DSP to reduce the amount of silica in solution. The slurry is passed on to a digestion stage where any remaining reactive silica dissolves, thus again increasing the concentration of silica in solution which may subsequently form more DSP as the process temperature increases. The liquor is later separated from undissolved solids, and alumina is recovered by precipitation as gibbsite. The spent liquor completes its circuit as it passes through a heat exchanger and back into the grinding stage. DSP scale accumulates throughout the Bayer process but particularly at the digestion stage and most particularly at or near the heat exchanger, where the recycled liquor passes through.

In this invention, it was discovered that dosing of various types of silane-based products can reduce the amount of DSP scale formed.

In at least one embodiment of the invention, an effective concentration of a silane-based small molecule product is added to some point or stage in the liquor circuit of the Bayer process, which minimizes or prevents the accumulation of DSP on vessels or equipment along the liquor circuit.

In at least one embodiment, the small molecule comprises the reaction product between an amine and at least one amine-reactive silane, the silicon of the silane can be monoalkyloxy, dialkyloxy, trialkyloxy or trihydroxy.

In at least one embodiment the small molecule is a reaction product between an amine-containing small molecule and an amine-reactive molecule containing at least one amine-reactive group per molecule and at least one —Si(OR)$_n$ group per molecule, where n=1, 2, or 3, and R═H, C1-C12 Alkyl, Aryl, Na, K, Li, or NH$_4$, or a mixture of such reaction products.

In at least one embodiment the method for the reduction of aluminosilicate containing scale in a Bayer process comprises the steps of:

adding to the Bayer process stream an aluminosilicate scale inhibiting amount of a composition comprising at least one small molecule, the at least one small molecule comprising of at least three components, one being an R$_1$ component, one being an R$_2$ component and one being an R$_3$ component, the components within the small molecule arranged according to the general formula:

wherein the small molecule may be at least one of: carbonates, bicarbonates, carbamates, ureas, amides and salts thereof and:

(i) R$_1$ is selected from the group consisting of H, alkyl, amine, alkylamine, structure (A) and structure (B);

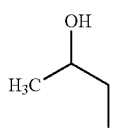
(A)

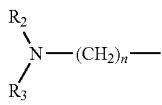
(B)

(ii) R$_2$ is independently selected from the group consisting of: H, alkyl, amine, alkylamine, G and E, G being one item selected from the group consisting of: 3-glycidoxypropyltrimethoxysilane, 3-glycidoxypropyltrialkoxysilane, 3-glycidoxypropylalkyldialkoxysilane, 3-glycidoxypropyldialkylmonoalkoxysilane, 3-isocyanatopropyltrialkoxysilane, 3-isocyanatopropylalkyldialkoxysilane, 3-isocyanatopropyldialkylmonoalkoxysilane, 3-chloropropyltrialkoxysilane, 3-chloropropylalkyldialkoxysilane, and 3-chloropropyldialkylmonoalkoxysilane;

E being 2-ethylhexyl glycidyl ether, n-butyl glycidyl ether, t-butyl glycidyl ether, C$_3$-C$_{22}$ glycidyl ether, C$_3$-C$_{22}$ isocyanate, C$_3$-C$_{22}$ chloride, C$_3$-C$_{22}$ bromide, C$_3$-C$_{22}$ iodide, C$_3$-C$_{22}$ sulfate ester, C$_3$-C$_{22}$ phenolglycidyl ether, and any combination thereof, (iii) R$_3$ is independently selected from the group consisting of: H, alkyl, aminealkylamine, G and E and (iv) n is an integer from 2 to 6.

In at least one embodiment the R$_1$ is independently selected from the group consisting of monoisopropanol amine, ethylene diamine, diethylene triamine, tetraethylene pentamine, isophoronediamine, xylenediamine, bis(aminomethyl)cyclohexane, hexanediainine, C,C,C-trimethylhexanediamine, methylene bis(aminocyclohexane), saturated fatty amines, unsaturated fatty amines such as oleylamine and soyamine, N-fatty-1,3-propanediamine such as cocoalkylpropanediamine, oleylpropanediamine, dodecylpropanediamine, hydrogenized tallow alkylpropanediamine, and tallow alkylpropanediamine and any combination thereof.

In another embodiment, the disclosure is directed to a method for the reduction of aluminosilicate containing scale in a Bayer process. The method comprises adding to a Bayer process stream an aluminosilicate scale inhibiting amount of a composition comprising a non-polymeric molecule. The non-polymeric molecule comprises at least three components. A first component of the at least three components has a general formula:

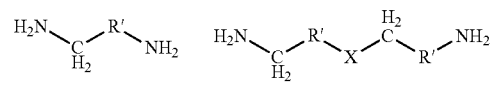

where R'═CH$_2$, or CH$_2$—CH$_2$; and X═NH$_2$, NH$_2$—R'—NH$_2$, or NH$_2$—R'—NH$_2$—R'—NH$_2$. A second component of the at least three components is 3-glycidoxypropyltrimethyloxysilane. A third component of the at least three components is 2-ethylhexylglycidyl ether. Synthesis of the non-polymeric molecule proceeds by combining the first component with the second component at a reactive hydrogen of the first component to form an intermediate, and then combining the intermediate with the third component to form the non-polymeric molecule.

In at least one embodiment said small molecule is selected from the group consisting of (I), (II), (III), (IV), (V), (VI), (VII), (VIII), and (IX):

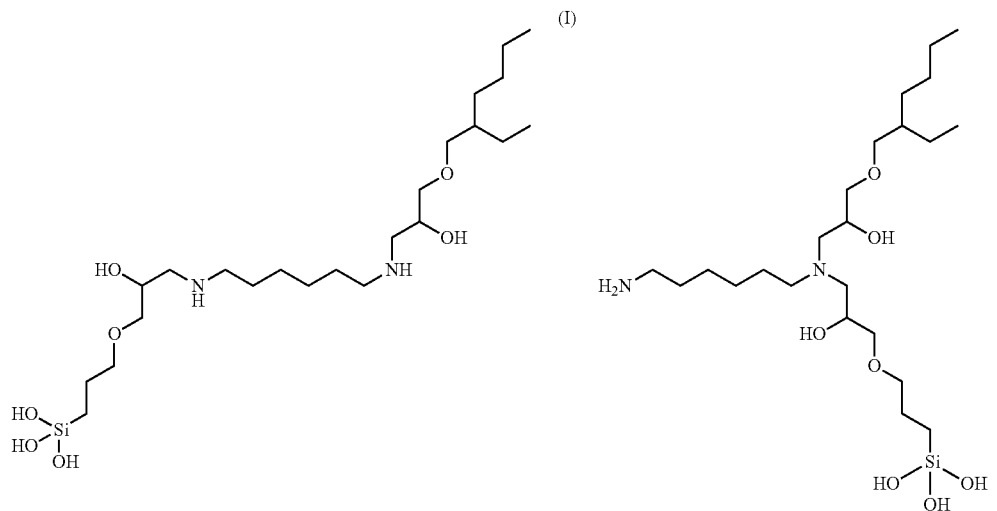
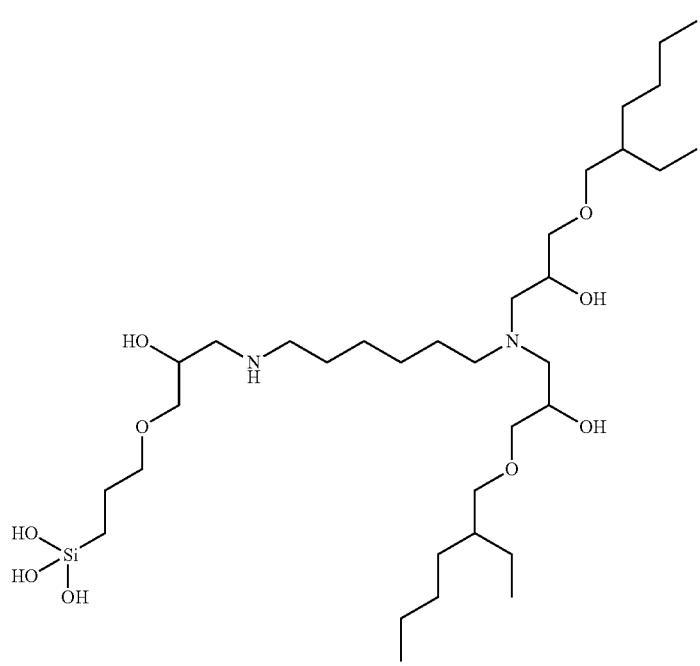

(IV)
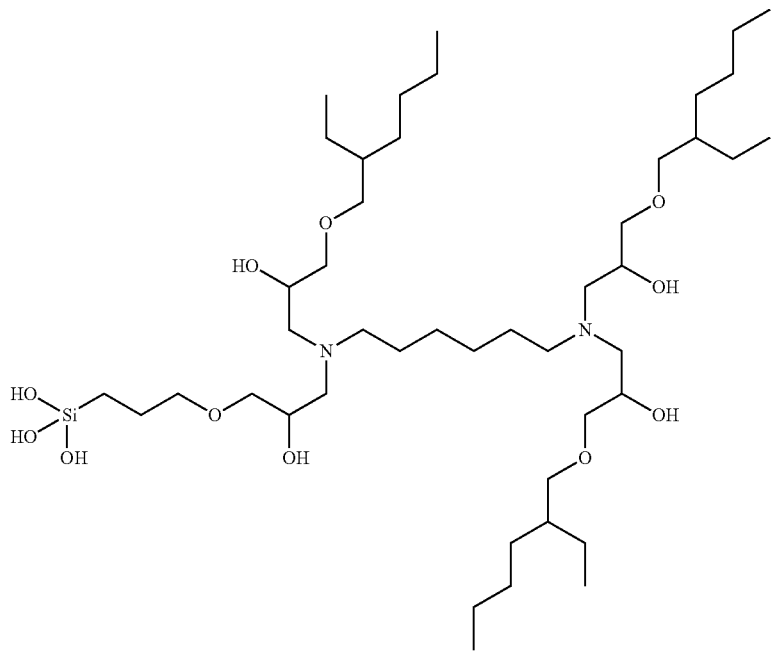
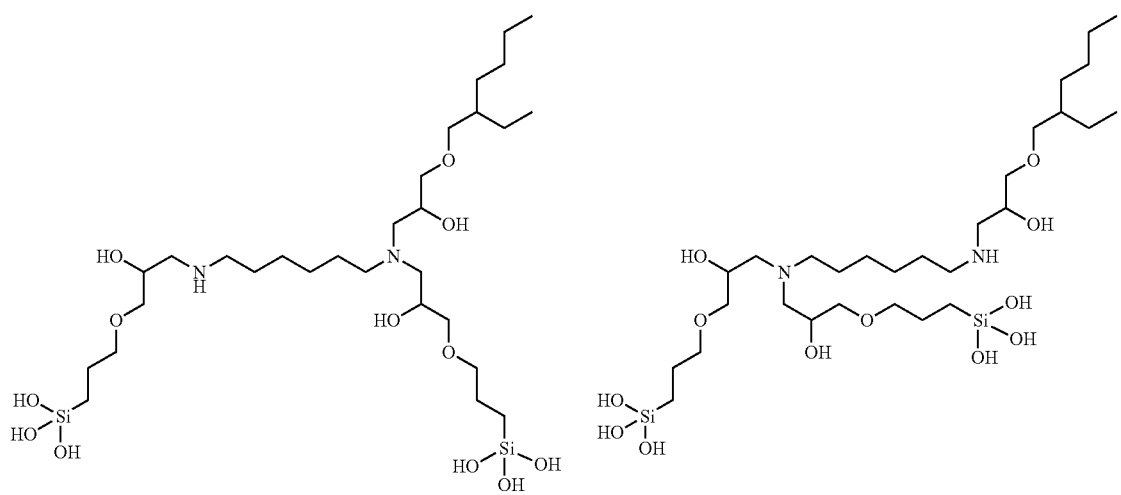
(VII)
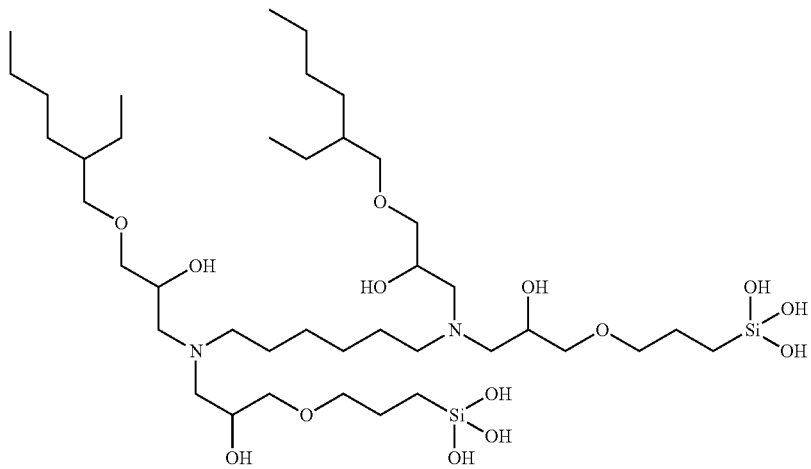

(VIII)
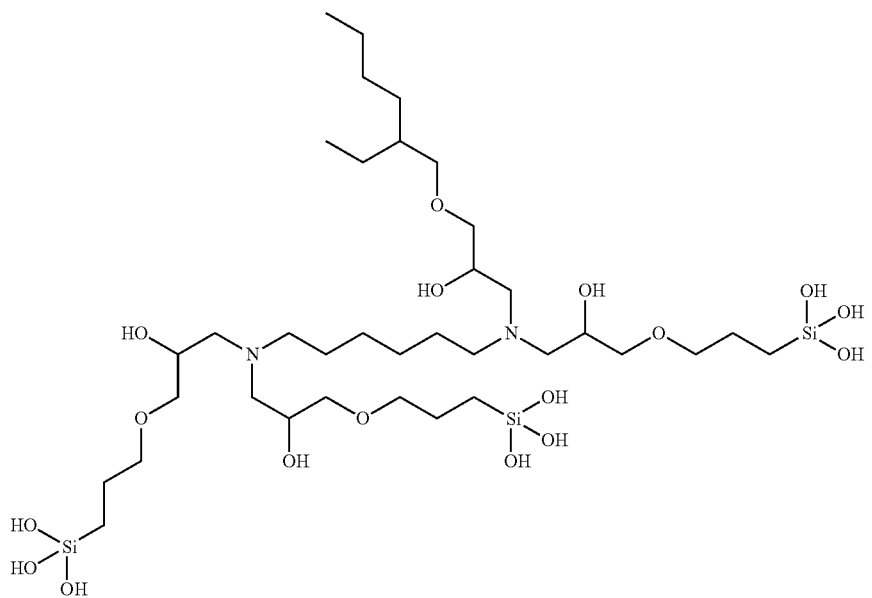
(IX)
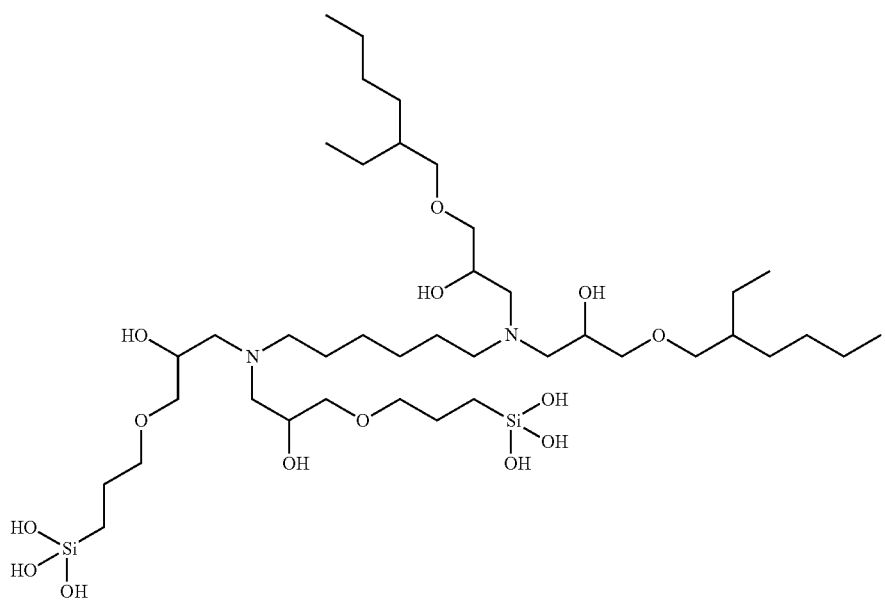

In at least one embodiment the small molecule is selected from the group consisting of: (X) (XI), (XII), (XIII), (XIV), (XV), (XVI), (XVII), (XVIII), and (XIX):
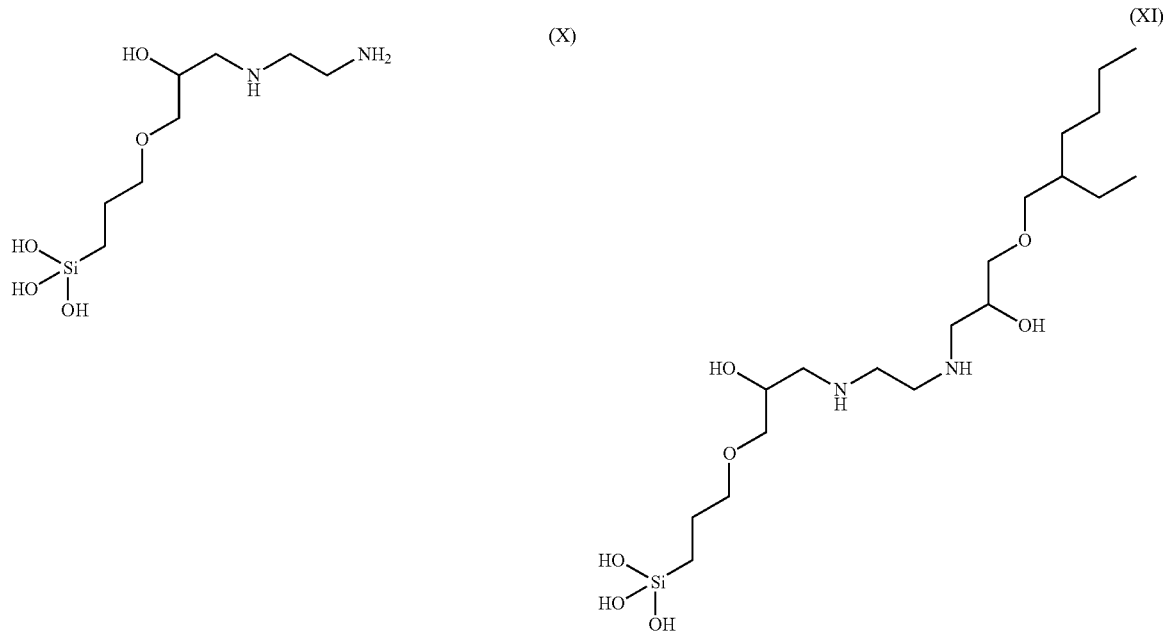
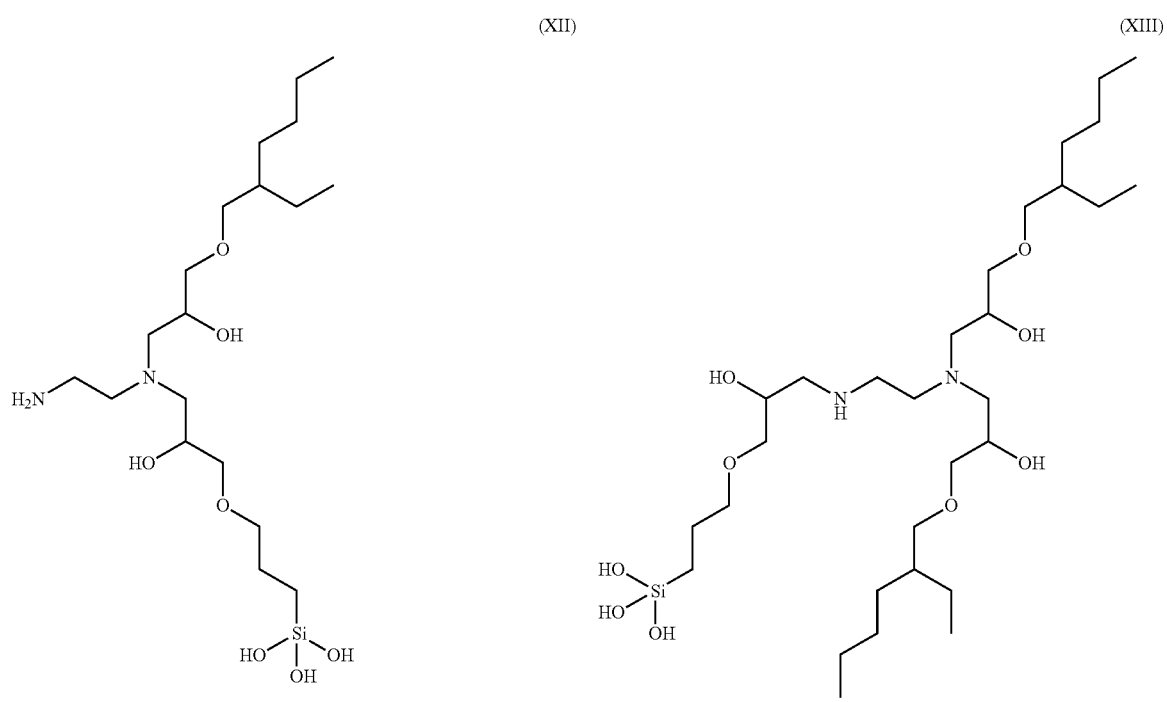

-continued
(XIV)
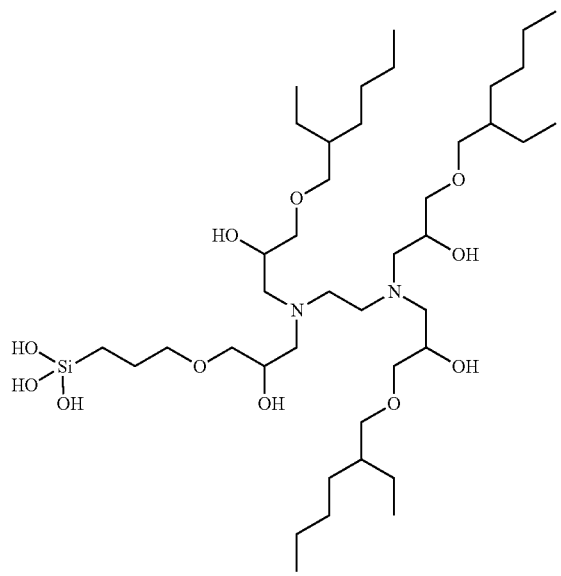
(XV)
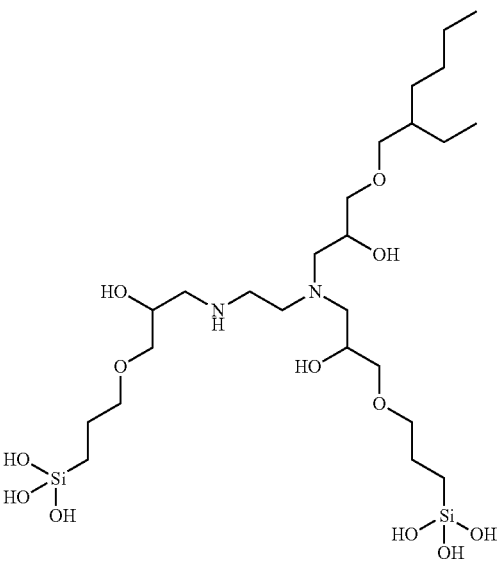
(XVI)
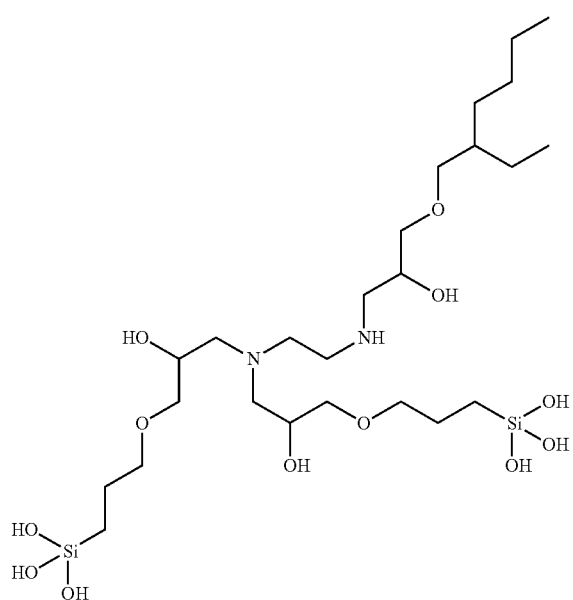
(XVII)
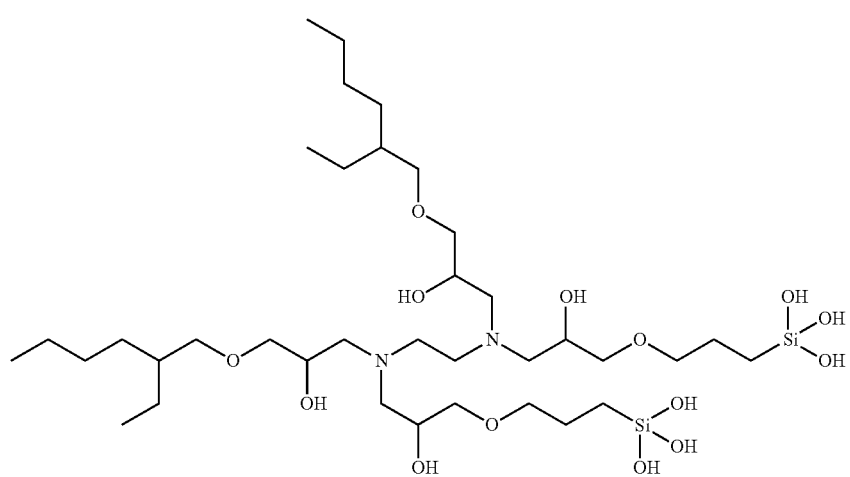

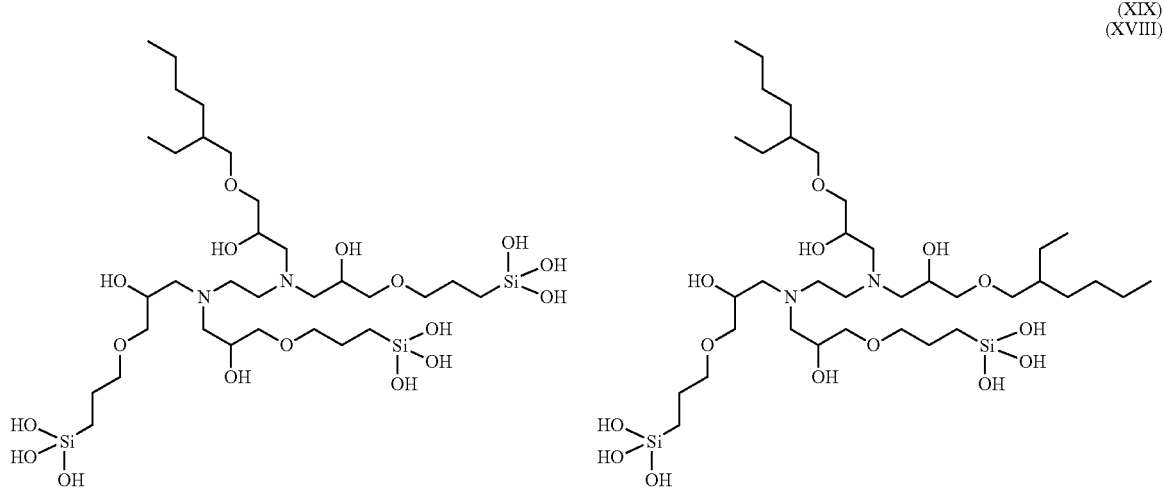 [SMILES: CCCCC(CC)COCC(O)CN(CCN(CC(O)COCCC[Si](O)(O)O)CC(O)COCCC[Si](O)(O)O)CC(O)COCCC[Si](O)(O)O ; CCCCC(CC)COCC(O)CN(CCN(CC(O)COCCC[Si](O)(O)O)CC(O)COCCC[Si](O)(O)O)CC(O)COCC(CC)CCCC]
In at least one embodiment the small molecule is selected from the group consisting of: (XX), (XXI), and (XXII):
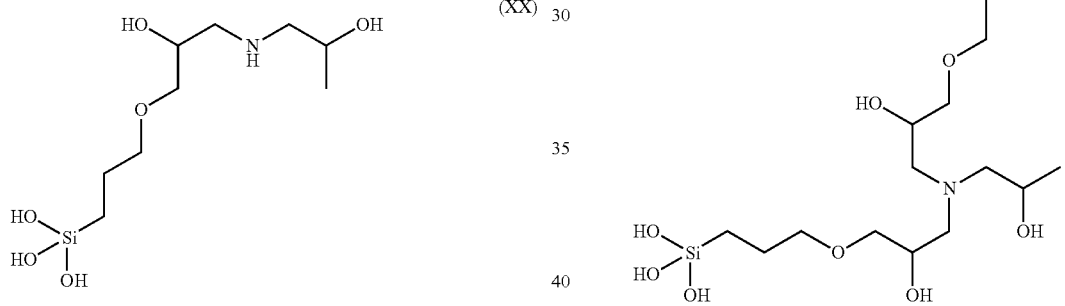
In at least one embodiment the small molecule is selected from the group consisting of: (XXIII), (XXIV), (XXV), (XXVI), (XXVII), (XVIII), and (XIX):
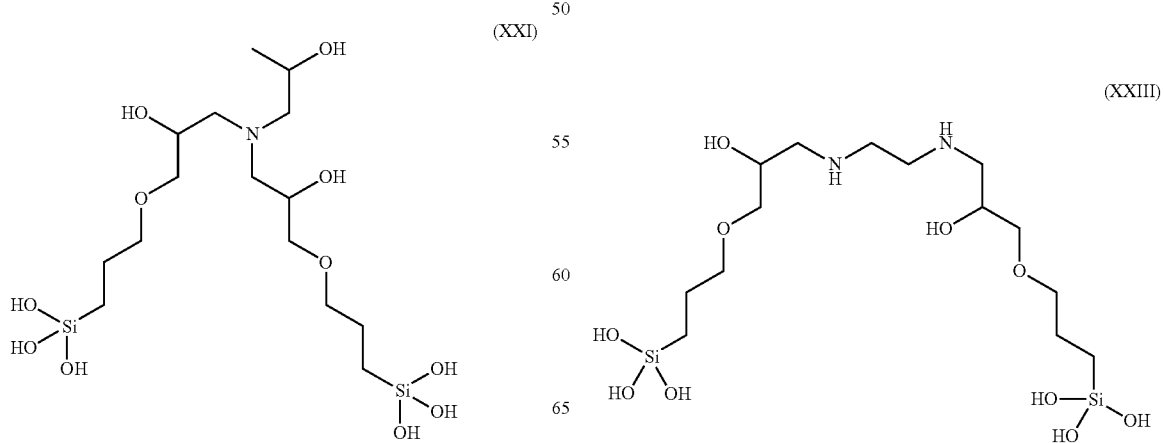

(XXIV)
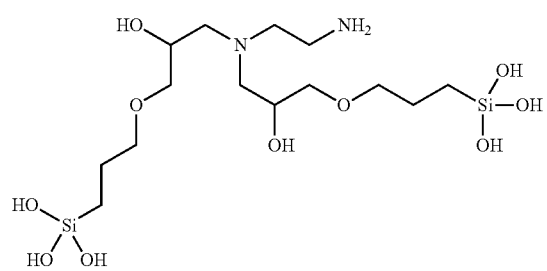
(XXVI)
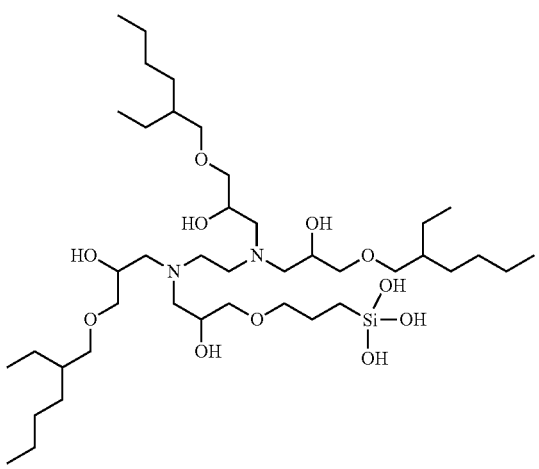
(XXV)
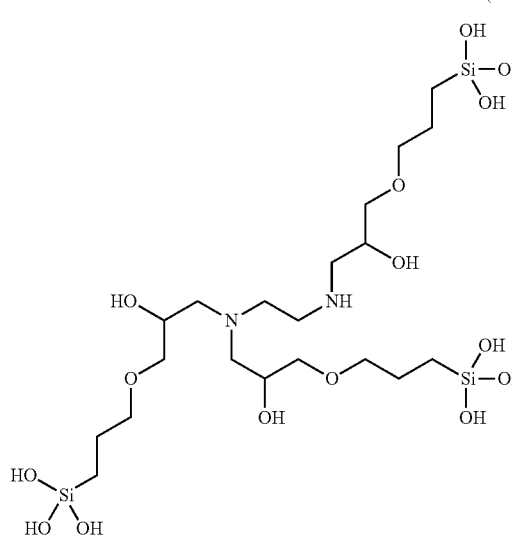
(XXVII)
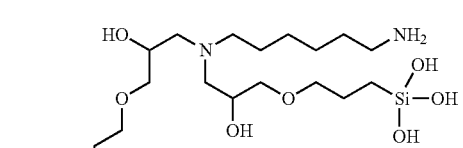
In at least one embodiment the small molecule is selected from the group consisting of: (XXVIII), (XXIX), (XXX), (XXXI), (XXXII) and combinations thereof:
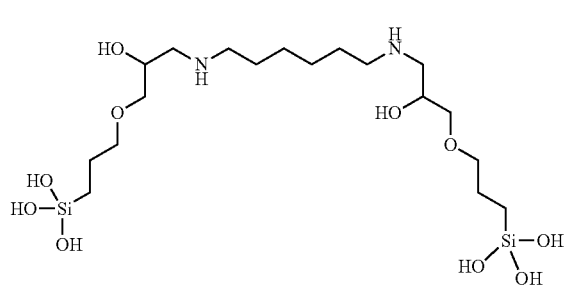
(XXIX)

(XXX)
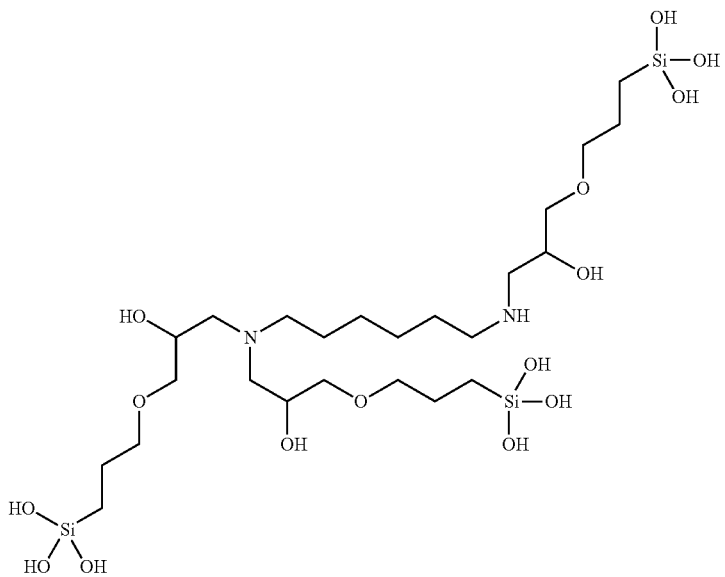
(XXXI)
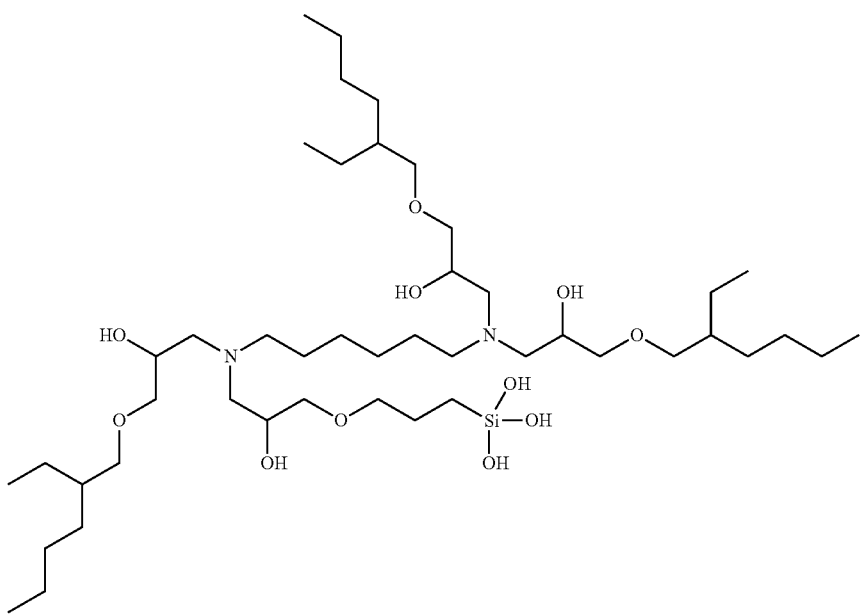

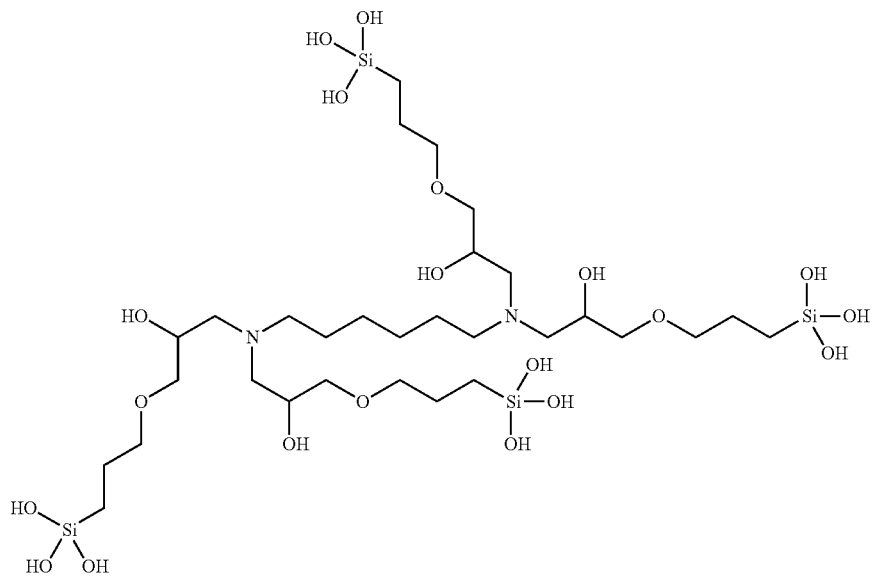
(XXXII)
In at least one embodiment the small molecule is selected from the group consisting of: (XXXIII), (XXXIV), (XXXV), (XXXVI), (XXXVII), (XXXIX), (XL), (XLI), and (XLII):
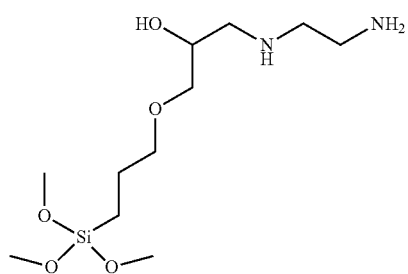
(XXXIII)
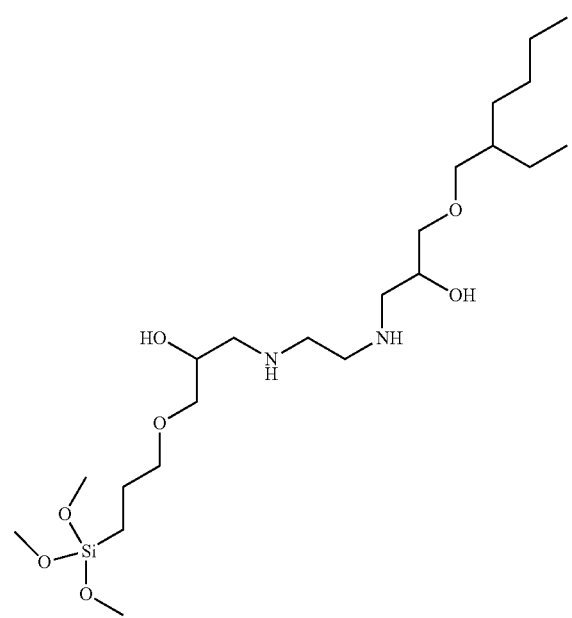
(XXXIV)

-continued
(XXXV)
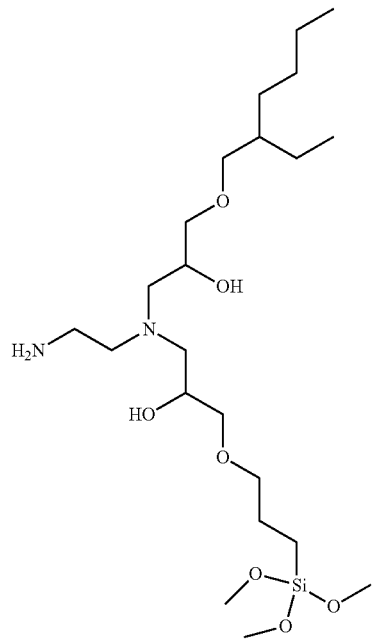
(XXXVI)
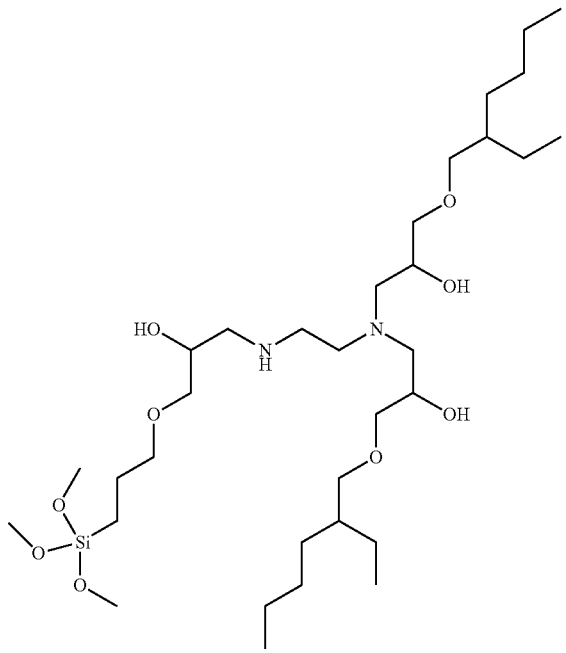
(XXXVII)
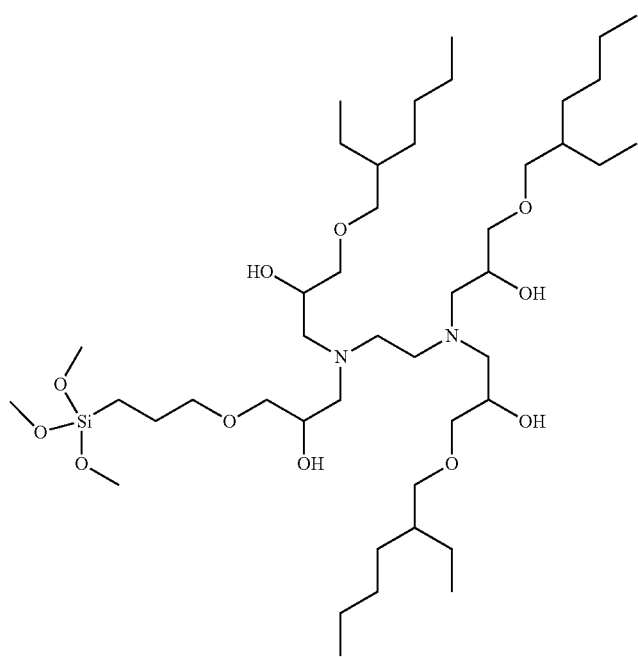

-continued
(XXXVIII)
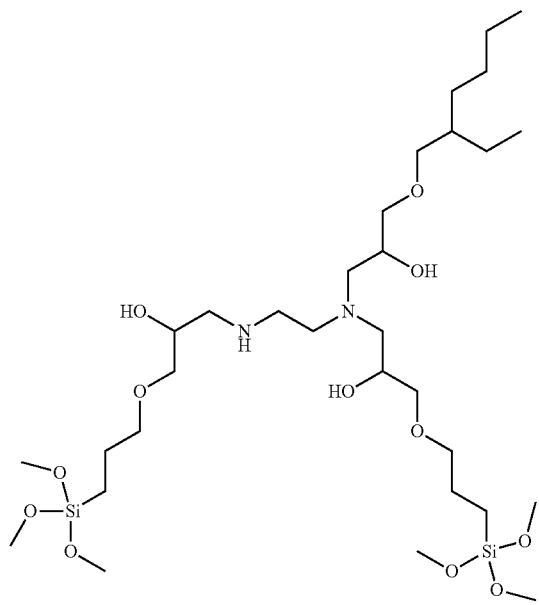
(XXXIX)
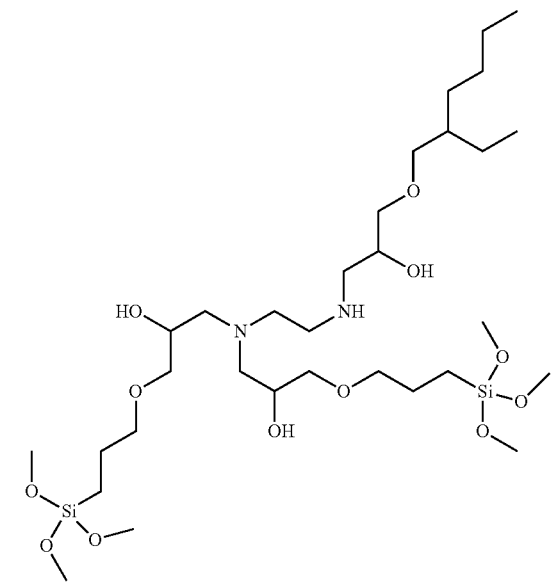
(XL)
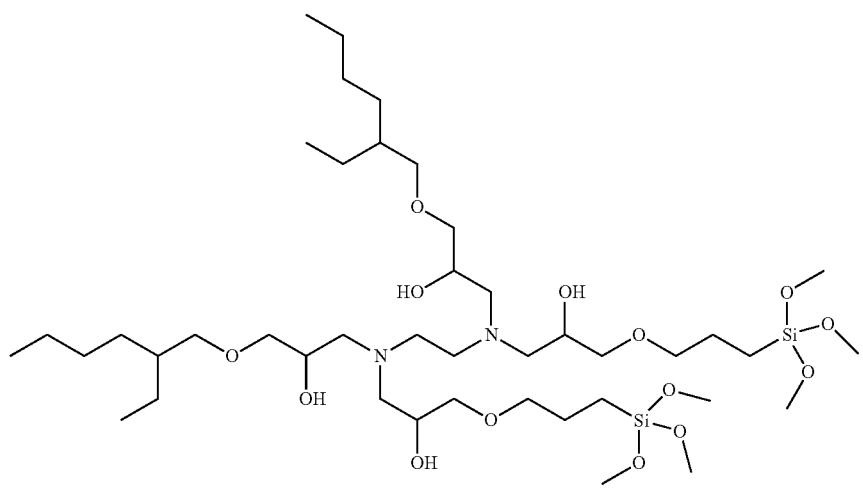
(XLI)
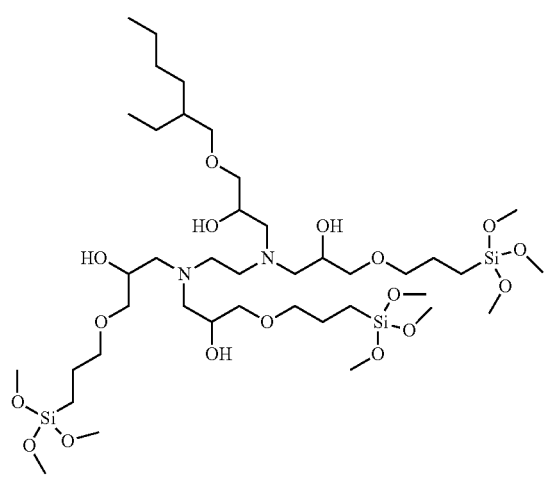
(XLII)
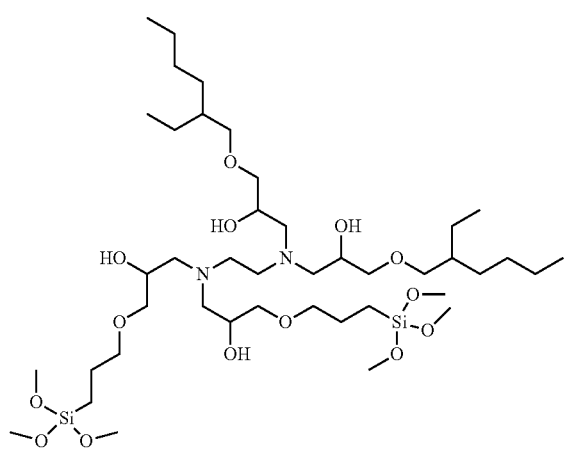

In at least one embodiment the small molecule is selected from the group consisting of: (XLIII), (XLIV), (XLV), (XLVI), (XLVII), (XLIX), (L), (LI), and (LII):
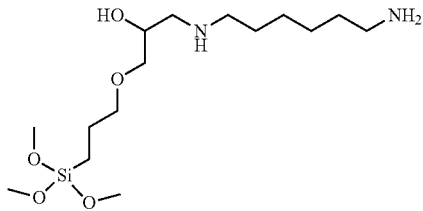
(XLIII)
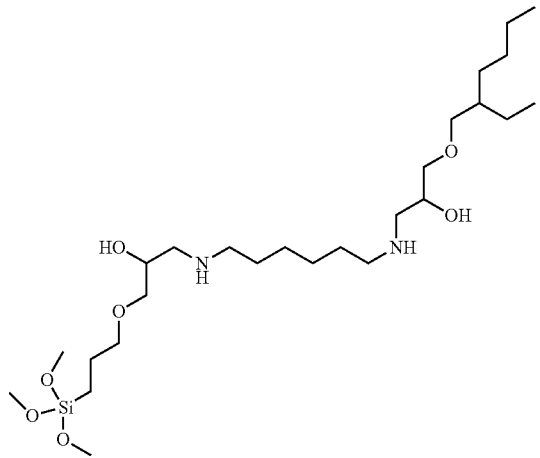
(XLIV)
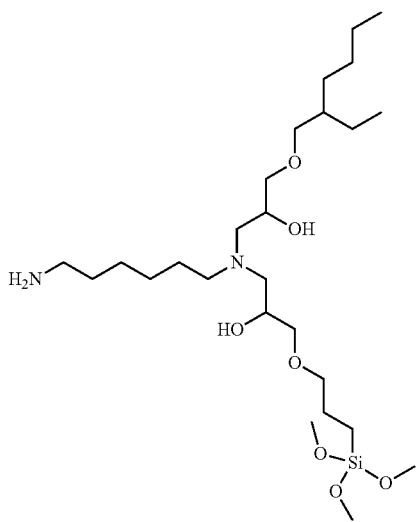
(XLV)
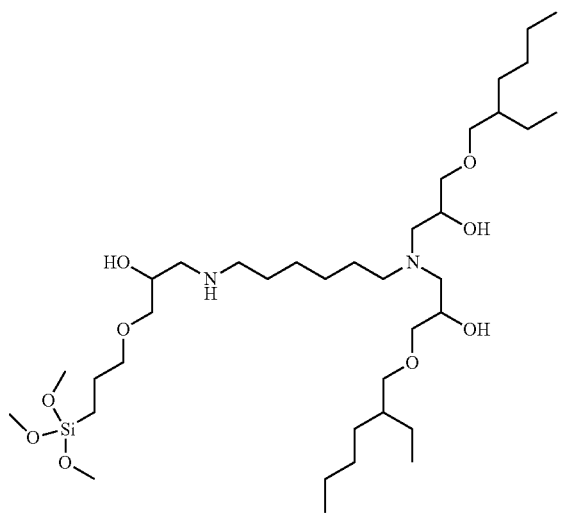
(XLVI)

-continued
(XLVII)
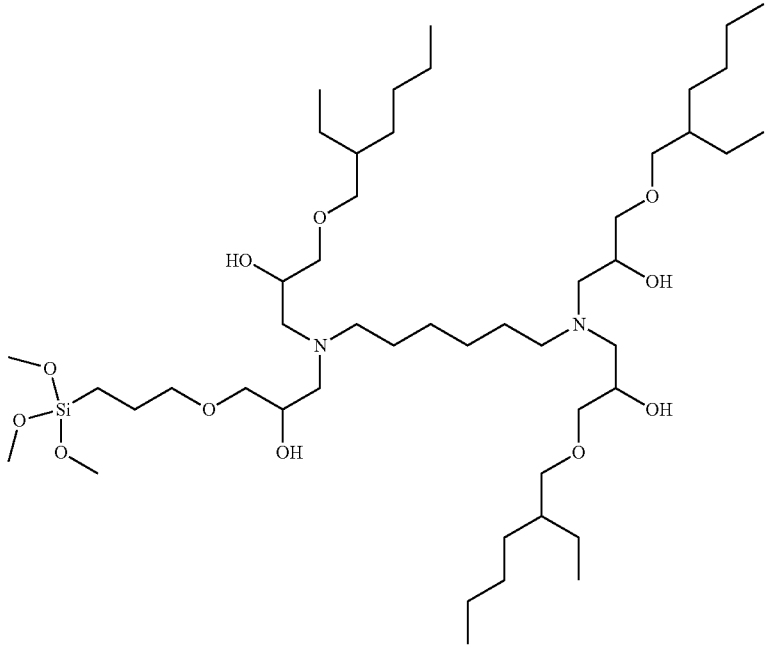
(XLVIII)
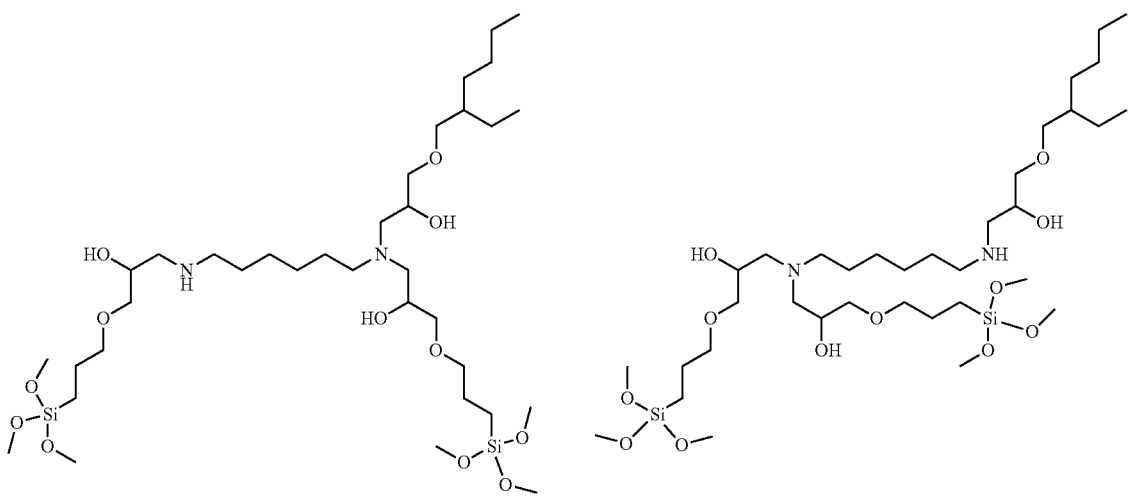
(XLIX)
(L)
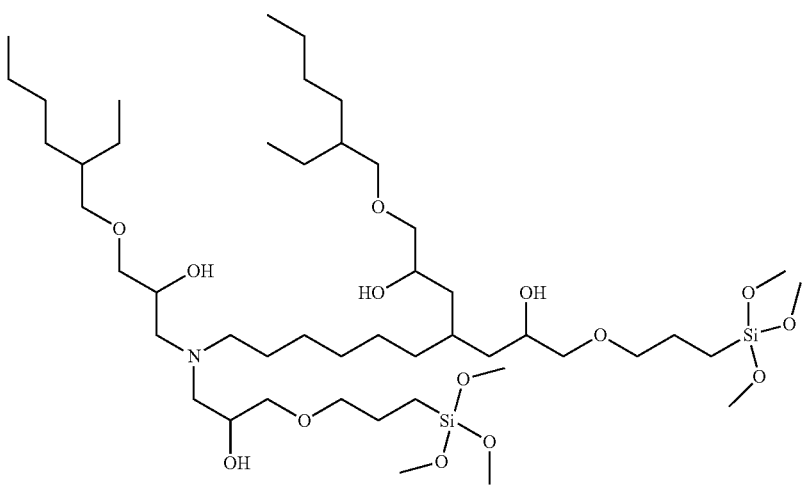

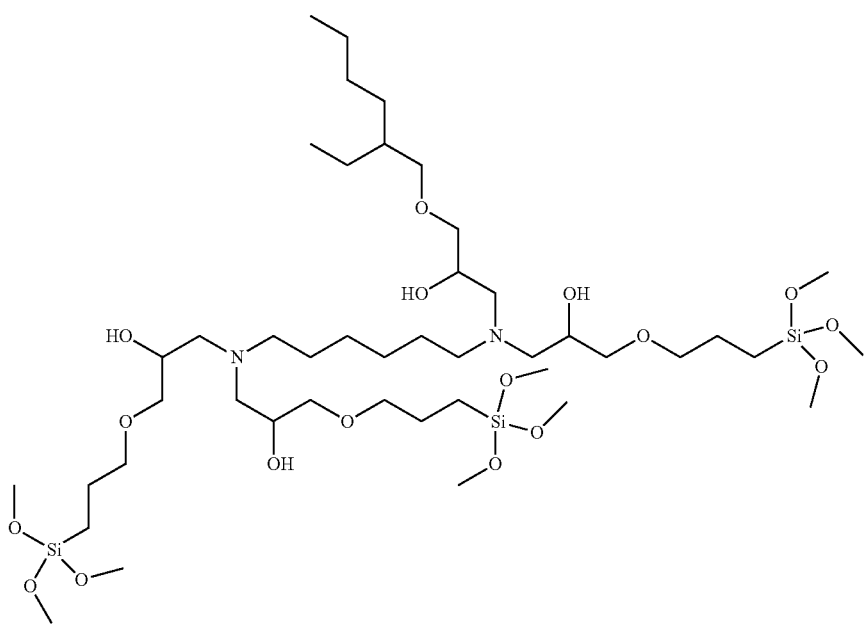
(LI)
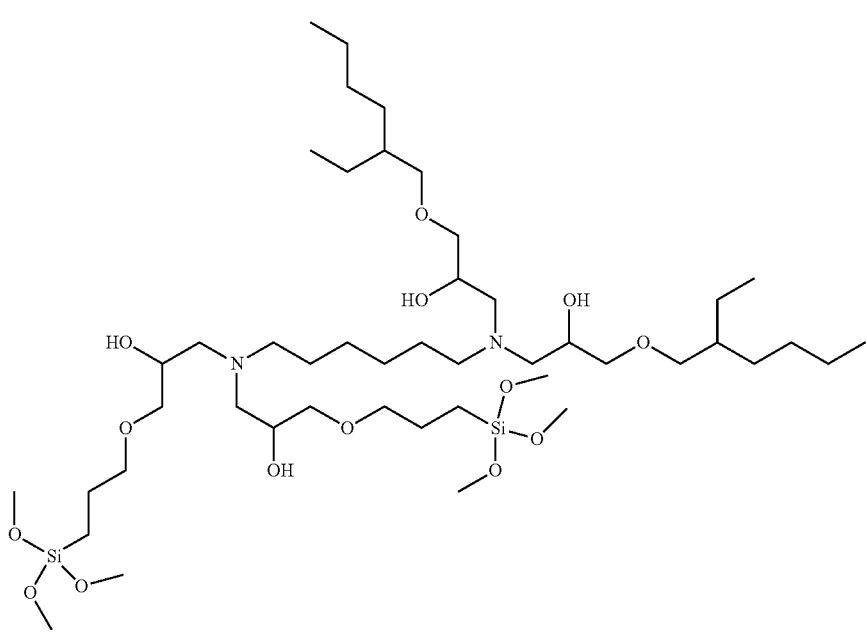
(LII)

In at least one embodiment the small molecule is selected from the group consisting of:
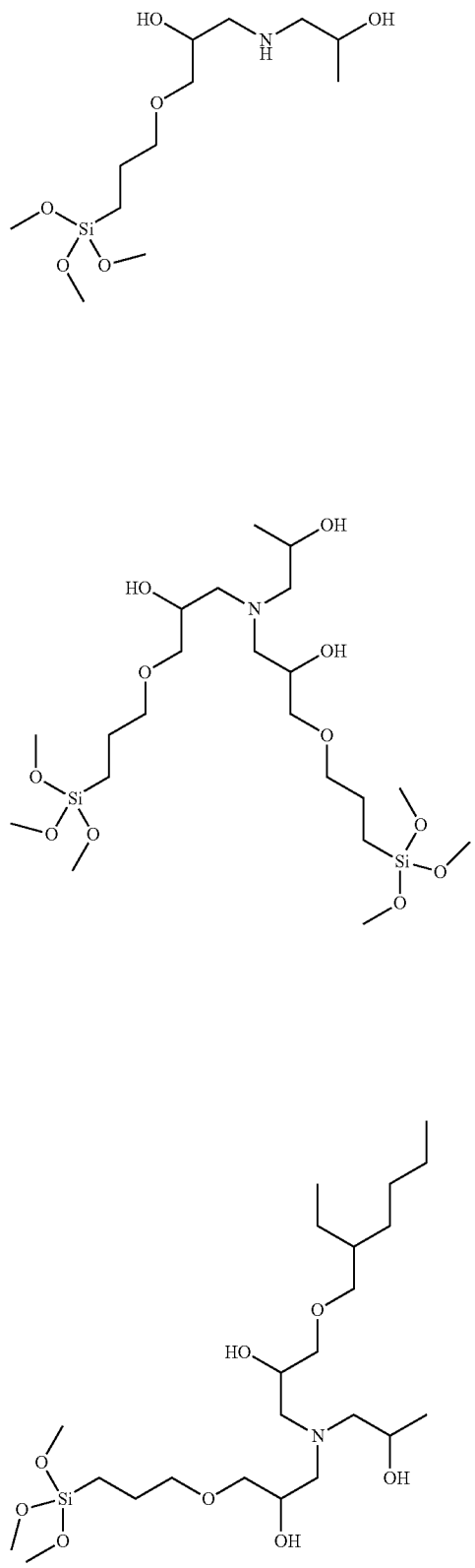
In at least one embodiment the small molecule is selected from the group consisting of (LVI), (LVII), (LVIII), (LIX), (LX), (LI), and (LII):
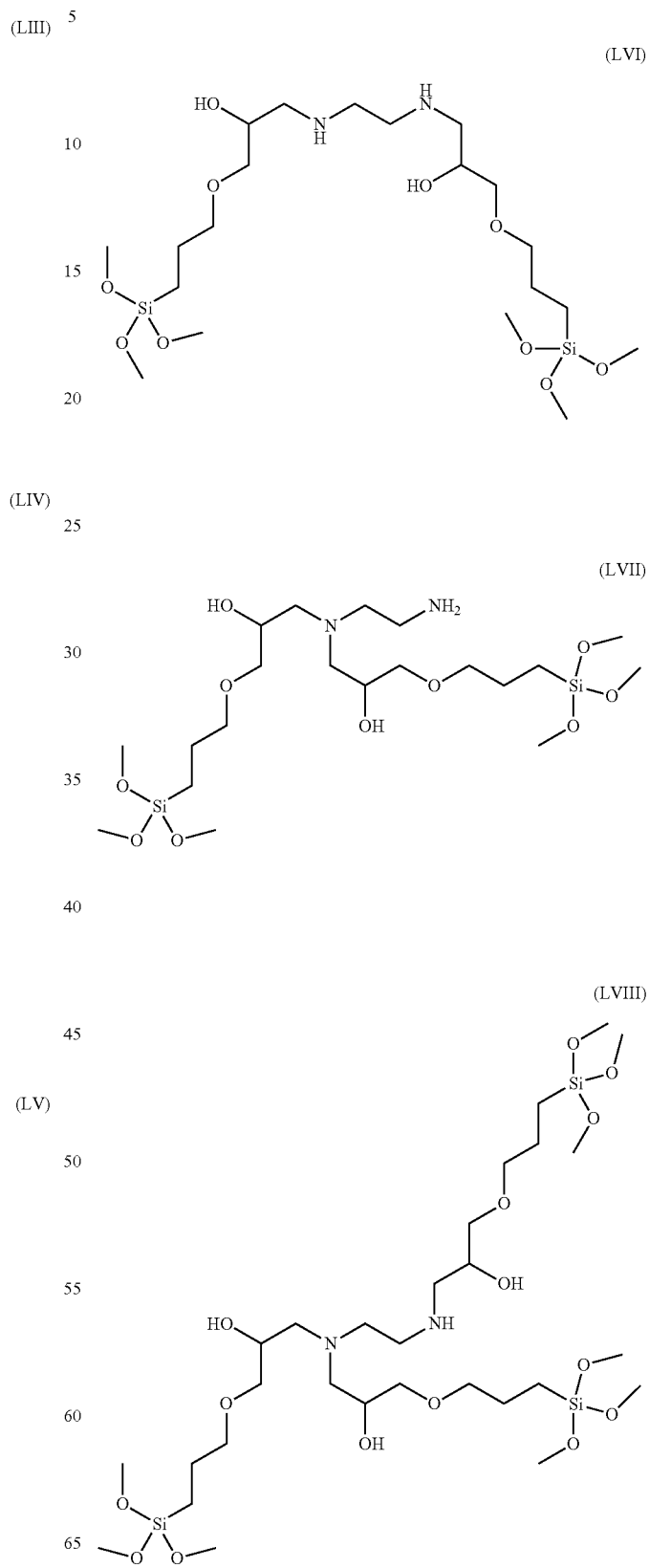

(LIX)
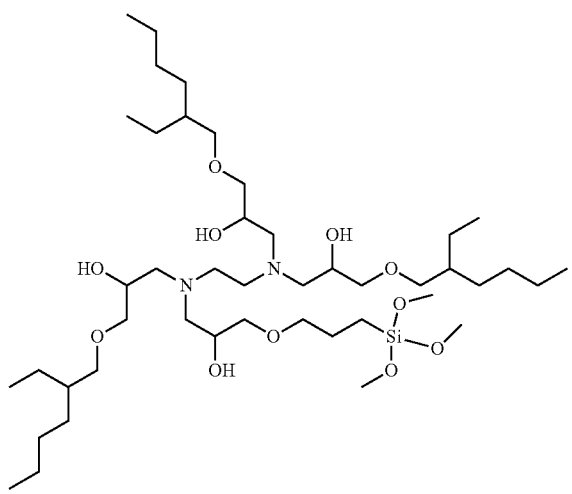
(LX)
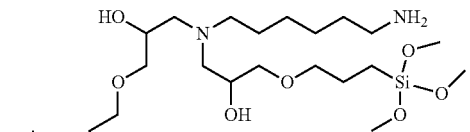
In at least one embodiment the small molecule is selected from the group consisting of (LXI), (LXII), (LXIII), (LXIV) and (LXV):
(LXI) (LXII)
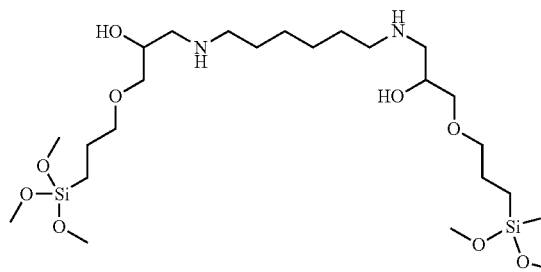
(LXIII)
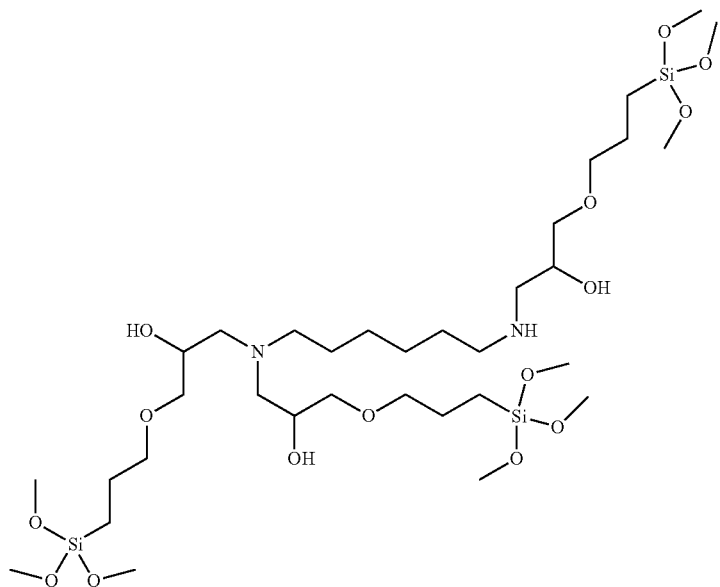

(LXIV)
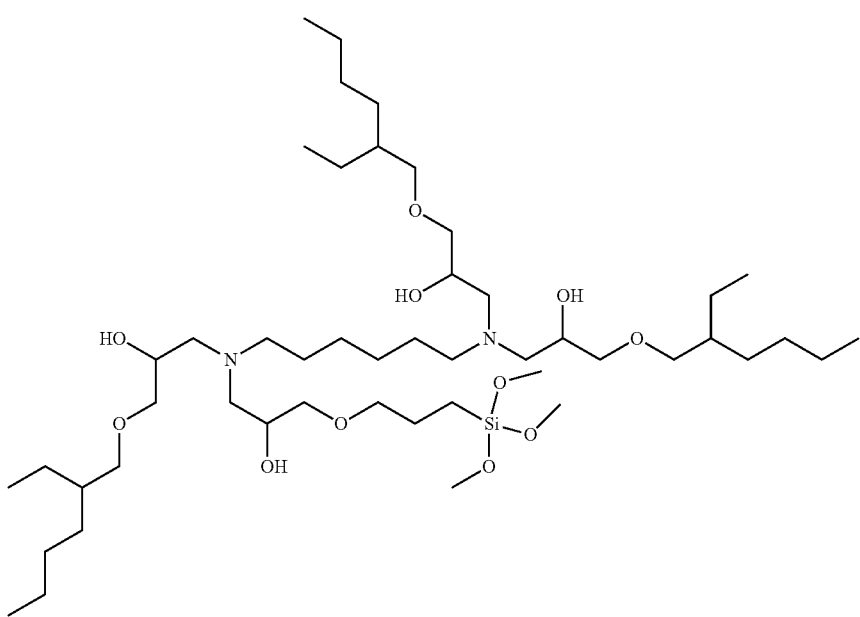
(LXV)
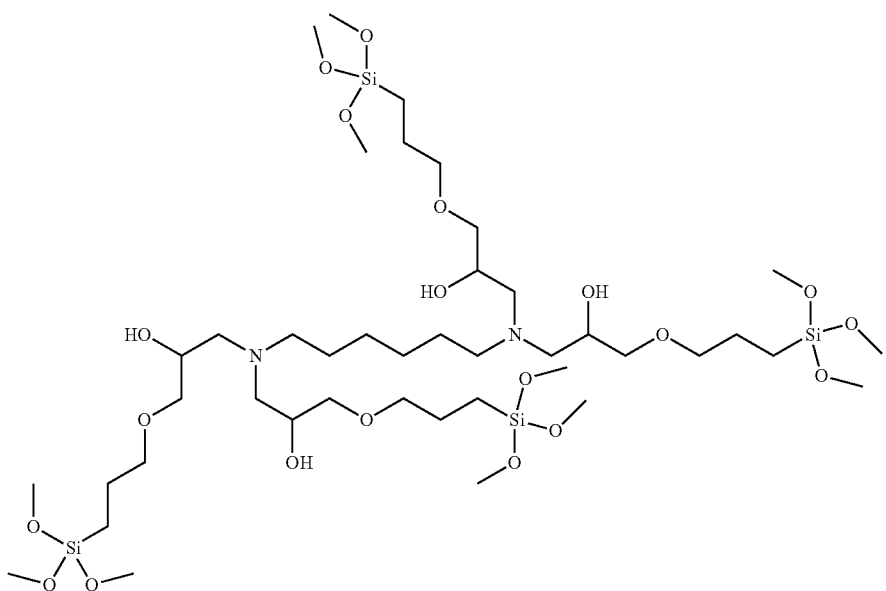
In at least one embodiment the small molecule is selected from the group consisting of (LXVI), (LXVII), (LXVIII), (LXIX), (LXX) and (LXXI):
(LXVI)
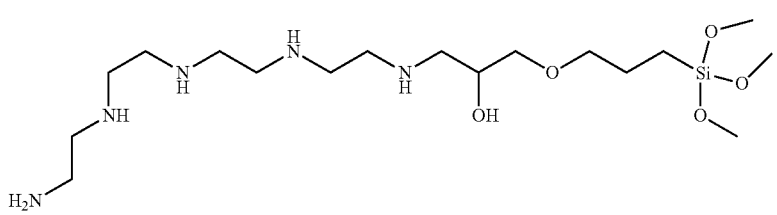

(LXVII)
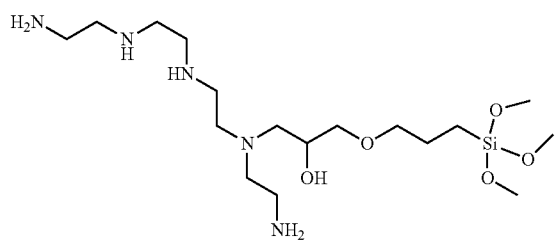
(LXVIII)
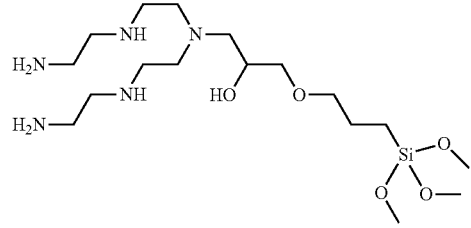
(LXIX)
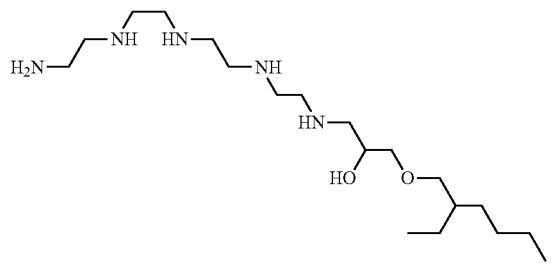
(LXX)
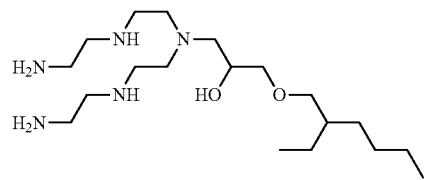
(LXXI)
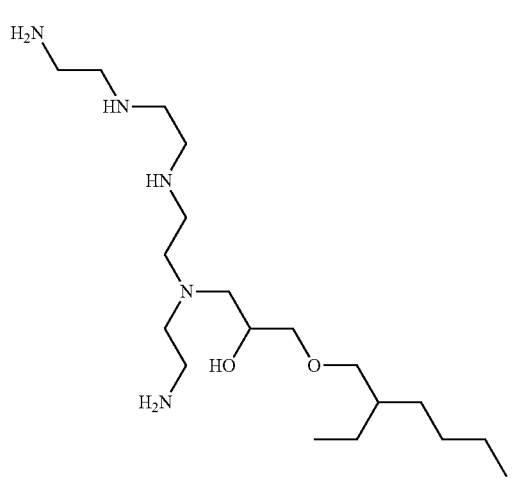

In at least one embodiment the small molecule is selected from the group consisting of: (LXXII), (LXXIII), (LXXIV) and (LXXV):
(LXXII)
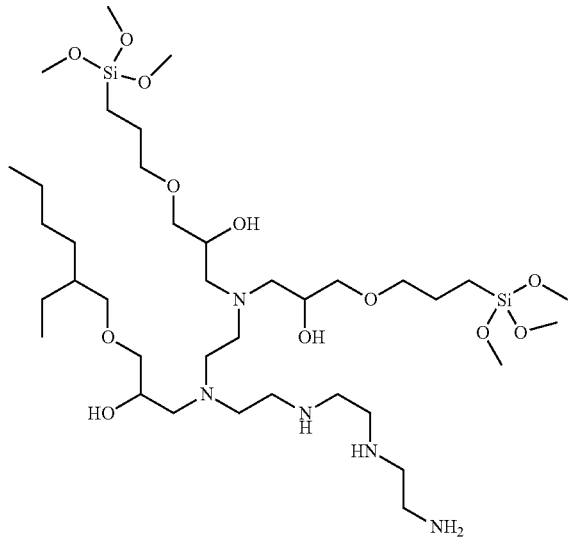
(LXXIV)
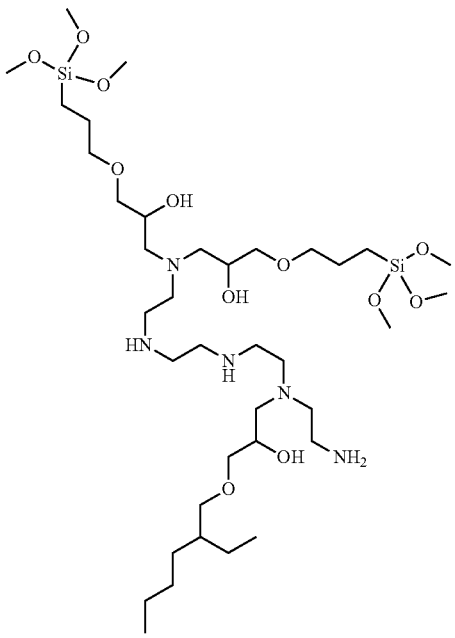
(LXXIII)
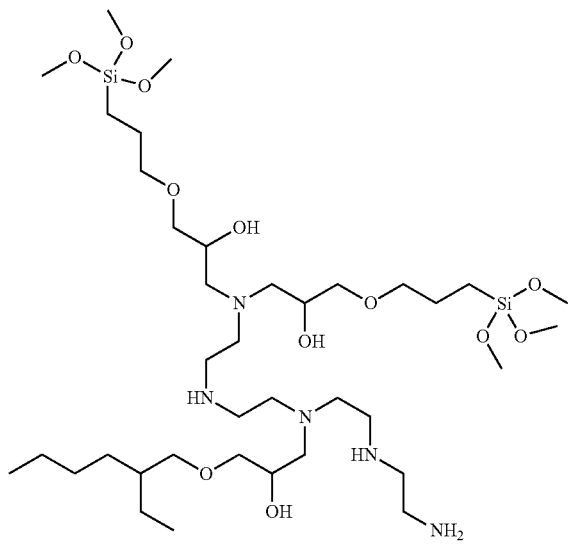
(LXXV)
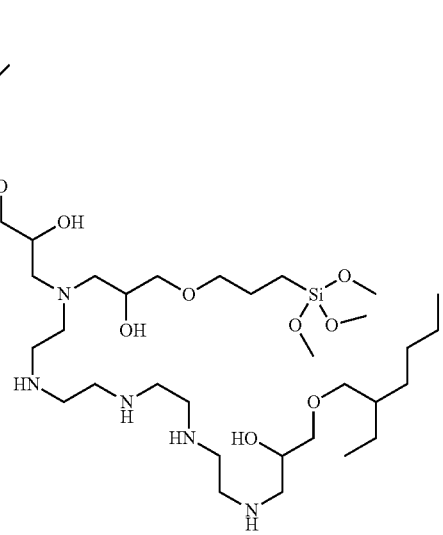
In at least one embodiment the small molecule is selected from the group consisting of (LXXVI), (LXXVII), (LXXVIII) and (LXXIX):

(LXXVI)
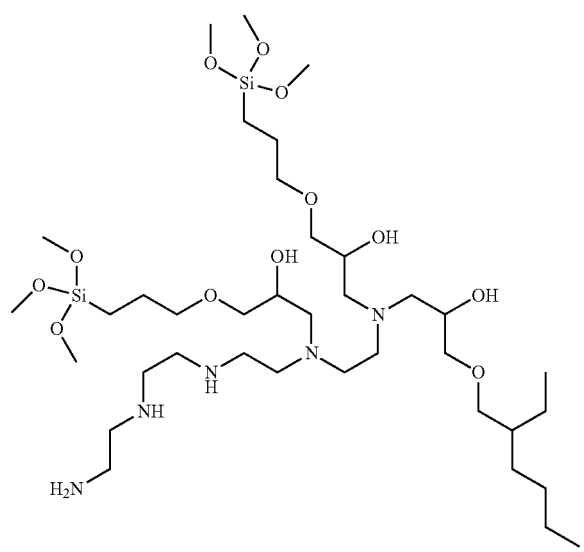
(LXXVII)
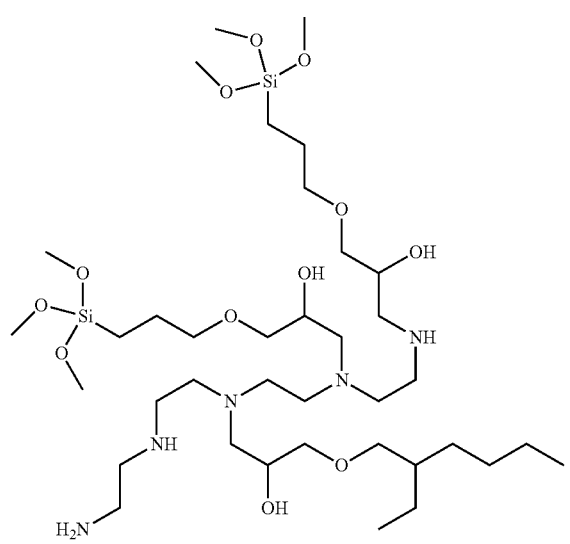
(LXXVIII)
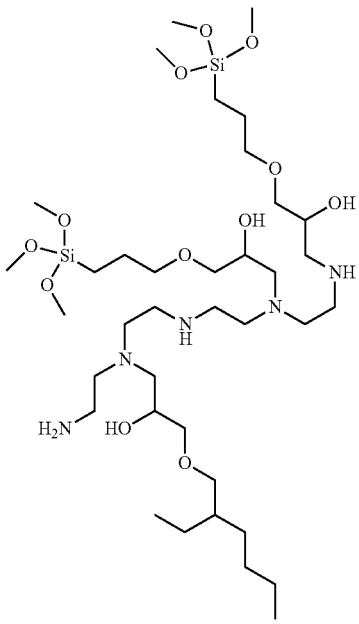
(LXXIX)
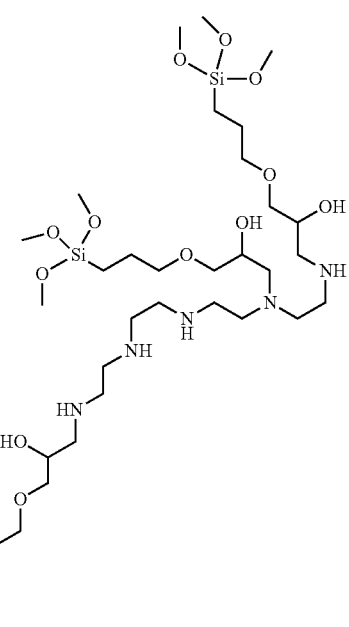
In at least one embodiment the small molecule is selected from the group consisting of: (LXXX), (LXXXI), (LXXXII) and (LXXXIII):

(LXXX)
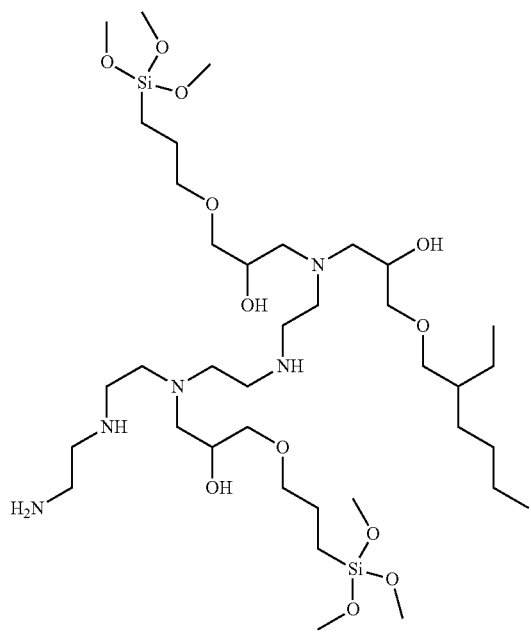
(LXXXI)
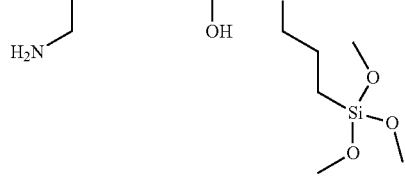
(LXXXII)
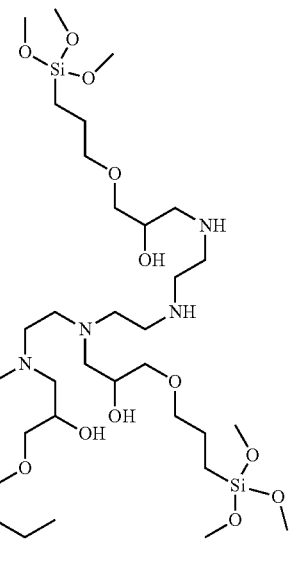
(LXXXIII)
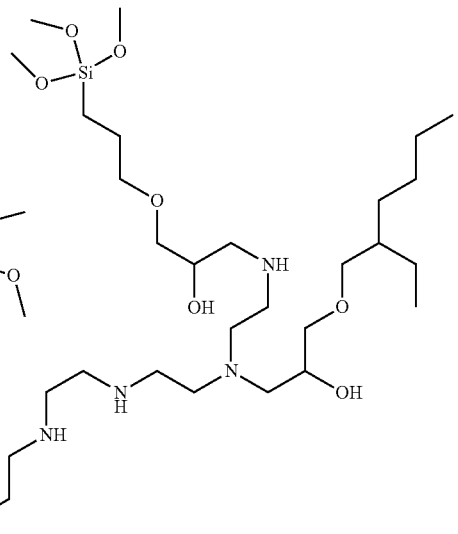
In at least one embodiment the small molecule is selected from the group consisting of: (LXXXIV), (LXXXV), (LXXXVI) and (LXXXVII):

(LXXXIV)
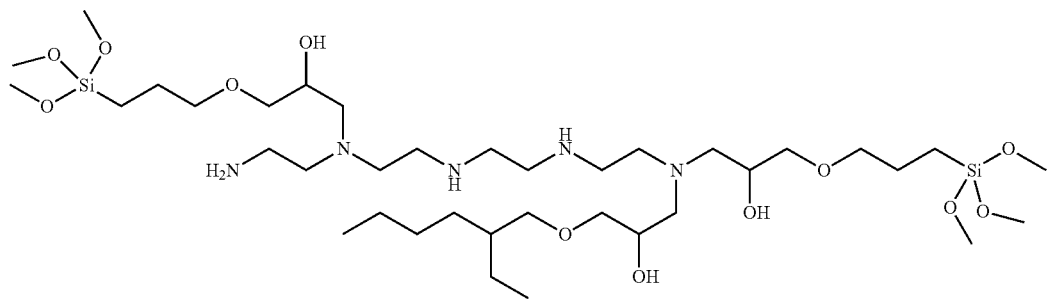
(LXXXV)
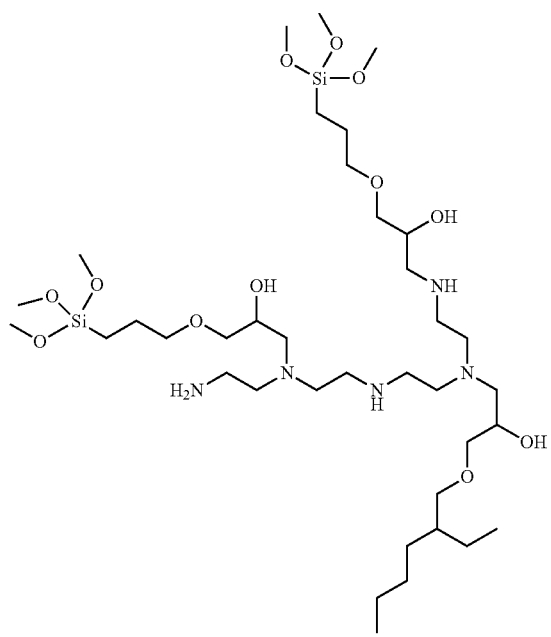
(LXXXVI)
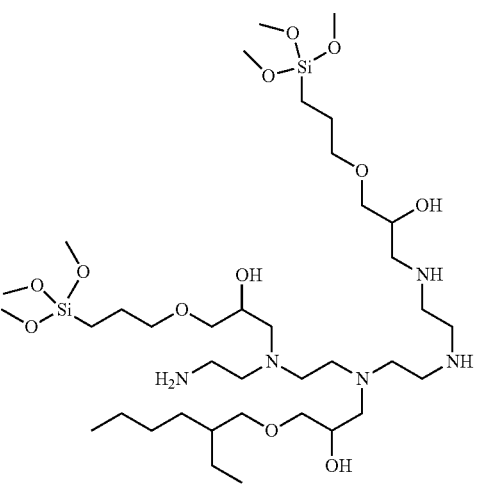
(LXXXVII)
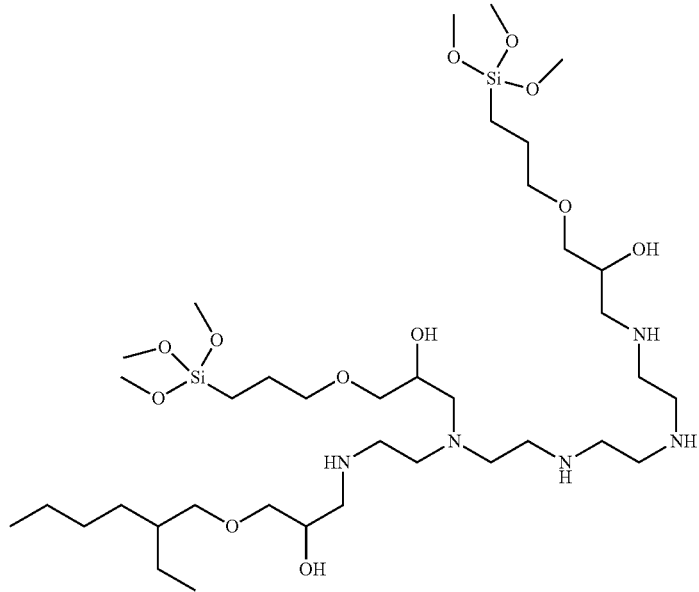

In at least one embodiment the small molecule is selected from the group consisting of (LXXXVIII), (LXXXIX) and (XC):
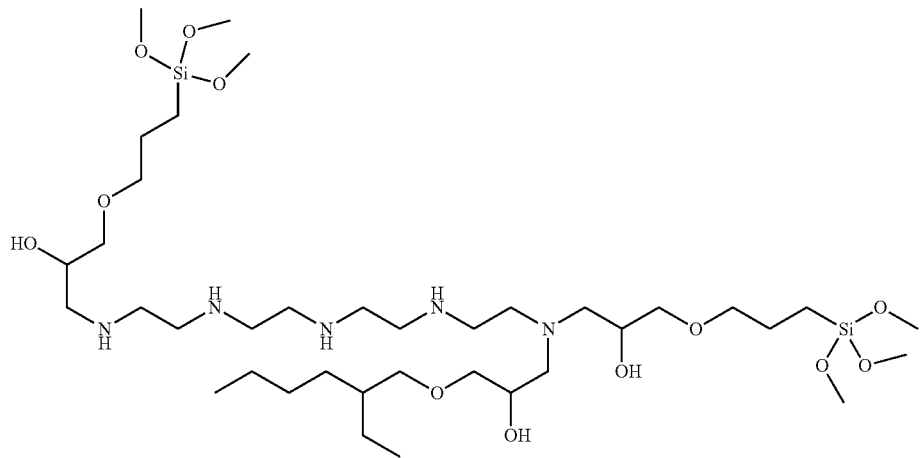
(LXXXVIII)
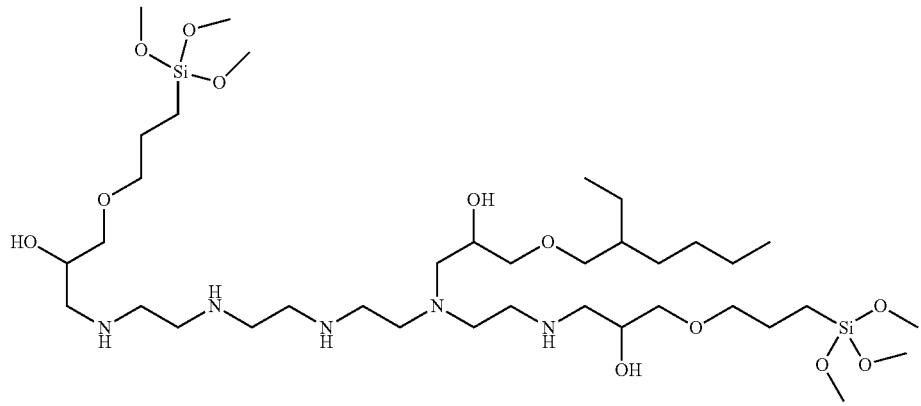
(LXXXIX)
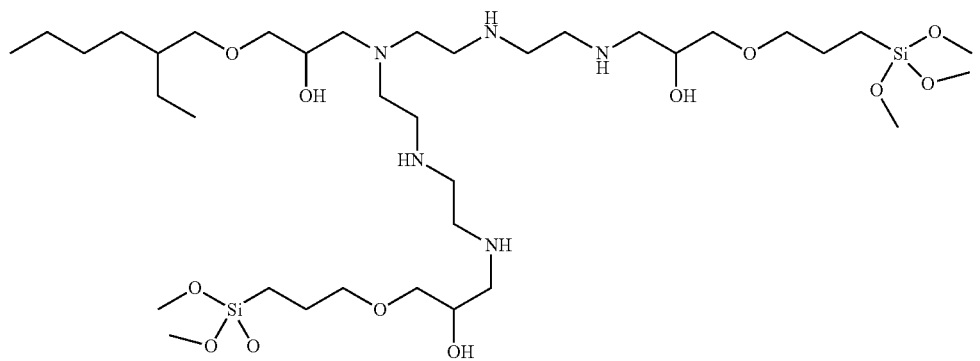
(XC)

In at least one embodiment the small molecule is selected from the group consisting of (XCI), (XCII), (XCIII), (XCIV) and (XCV):
(XCI)
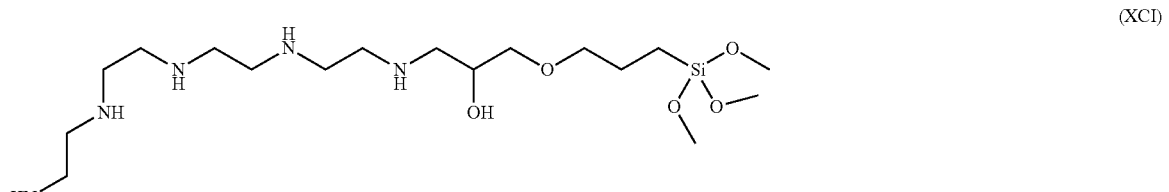
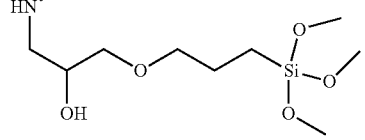
(XCII)
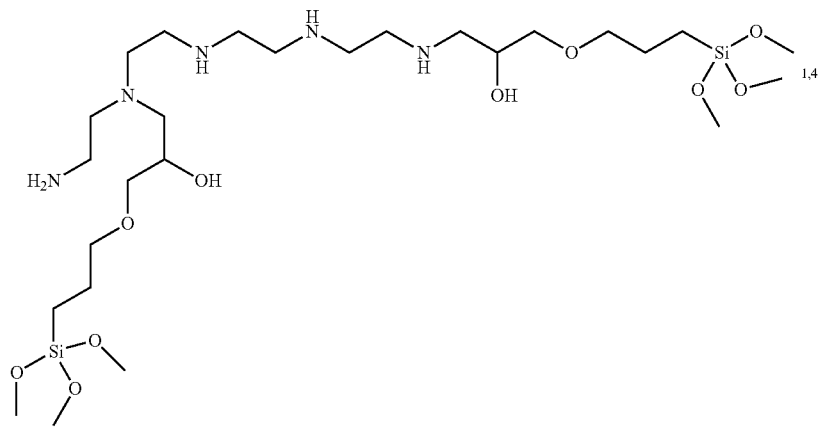
(XCIII)
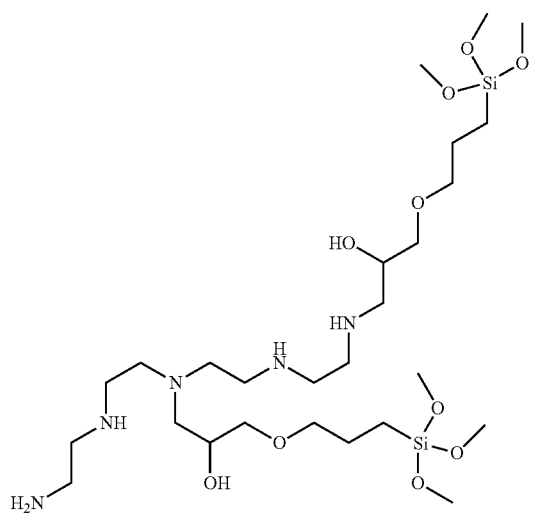
(XCIV)
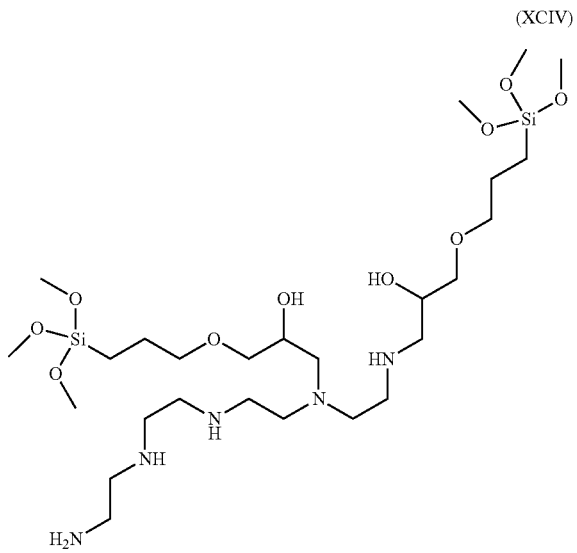

(XCV)
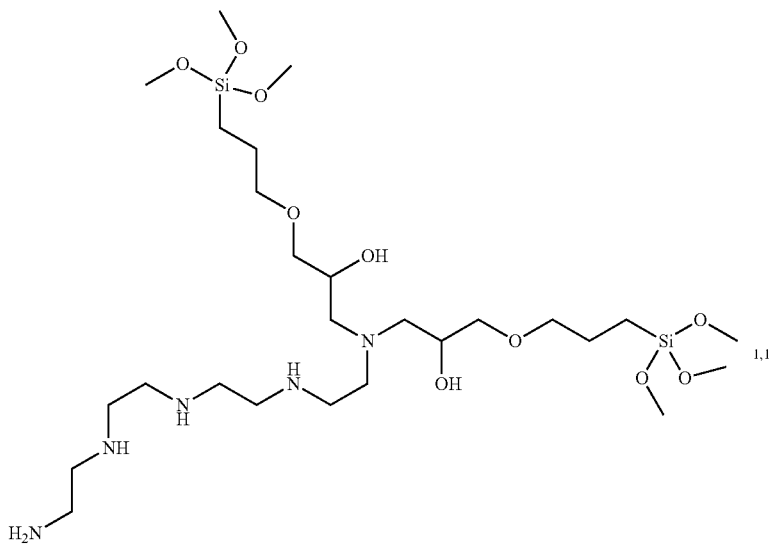
In at least one embodiment the small molecule is selected from the group consisting of: (XCVI), (XCVII) and (XCVIII):
(XCVI)
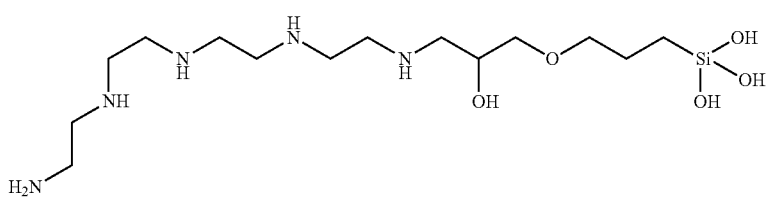
(XCVII)
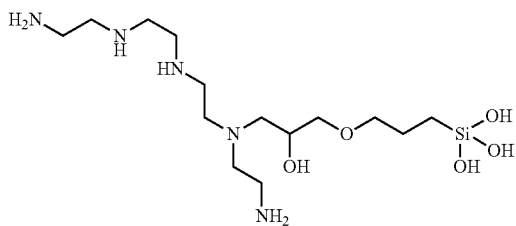
(XCVIII)
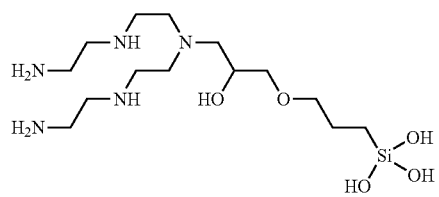

In at least one embodiment the small molecule is selected from the group consisting of (XCIX), (C), (CI) and (CII):
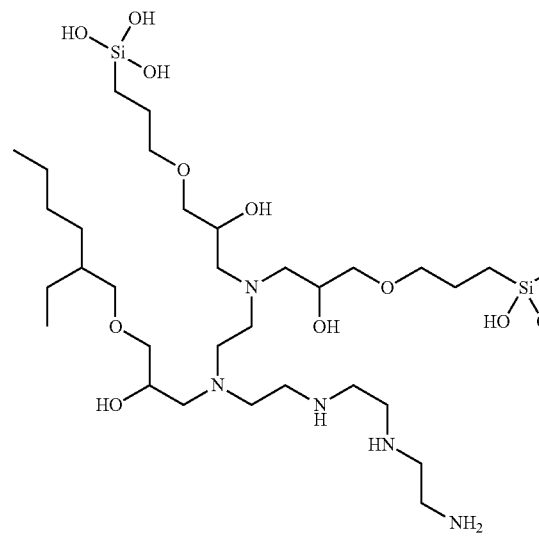
(XCIX)
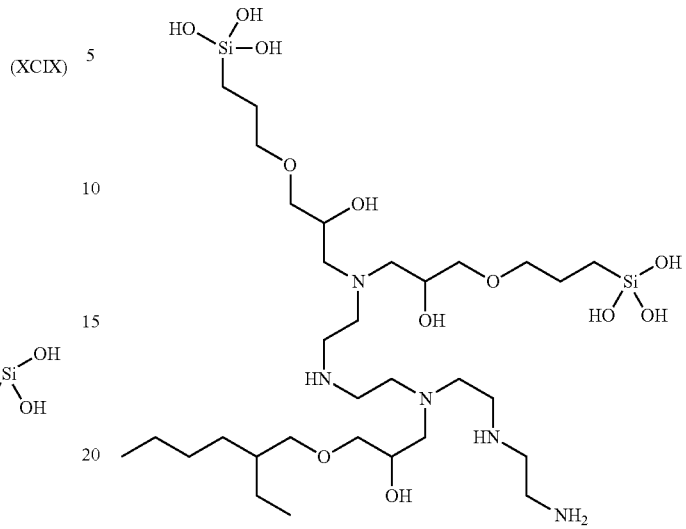
(CI)
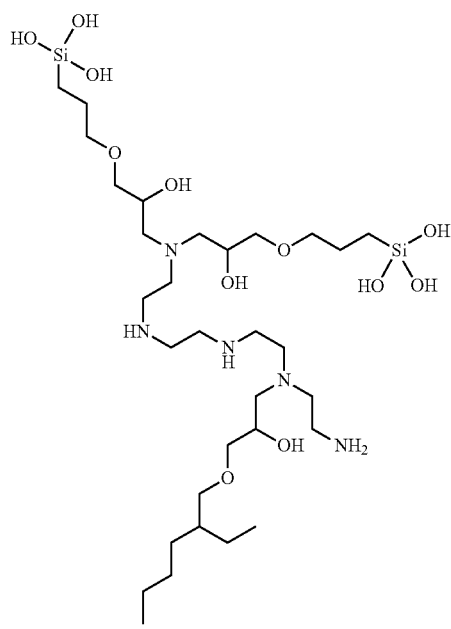
(C)
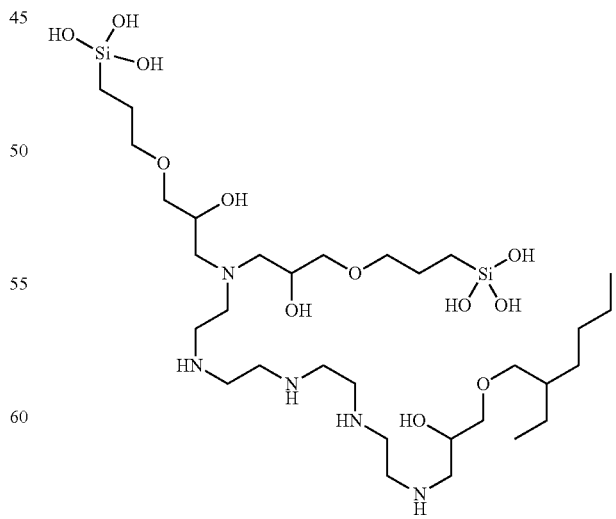
(CII)
In at least one embodiment the small molecule is selected from the group consisting of: (CIII), (CIV), (CV) and (CVI):

(CIII)
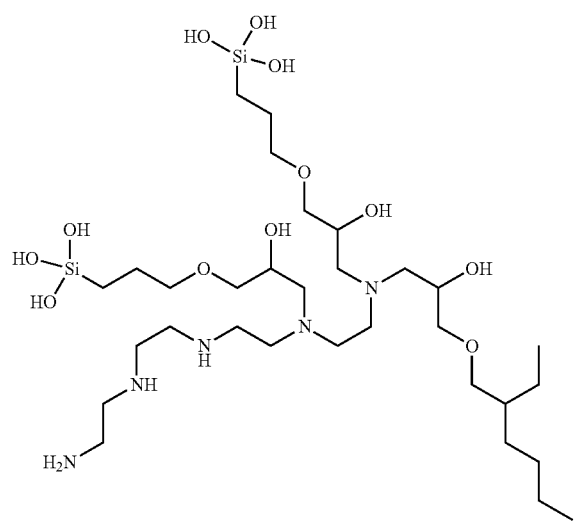
(CV)
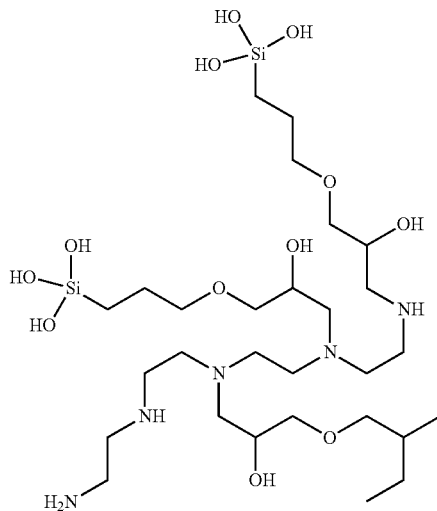
(CIV)
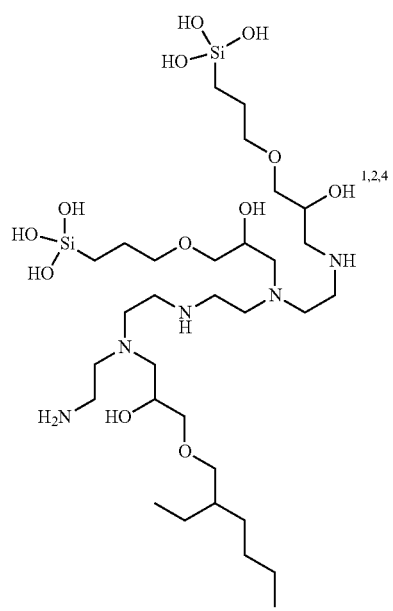
(CVI)
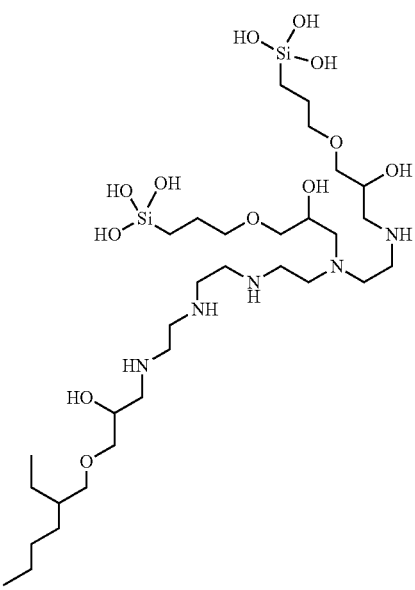
In at least one embodiment the small molecule is selected from the group consisting of: (CVII), (CVIII), (CIX) and (CX):

(CVII)
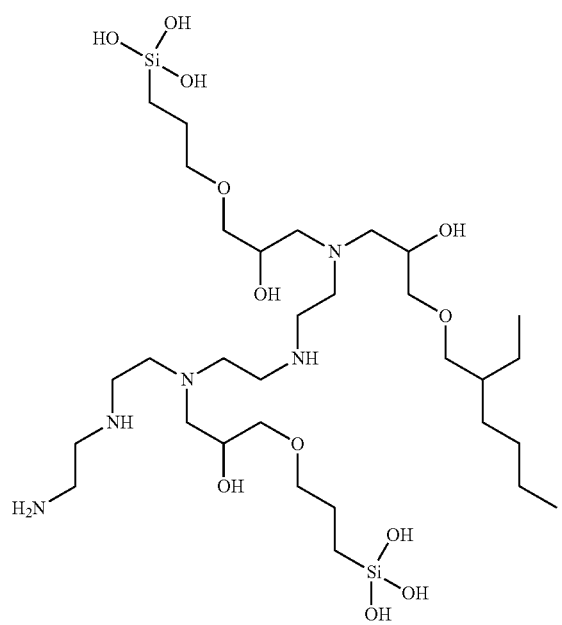
(CXII)
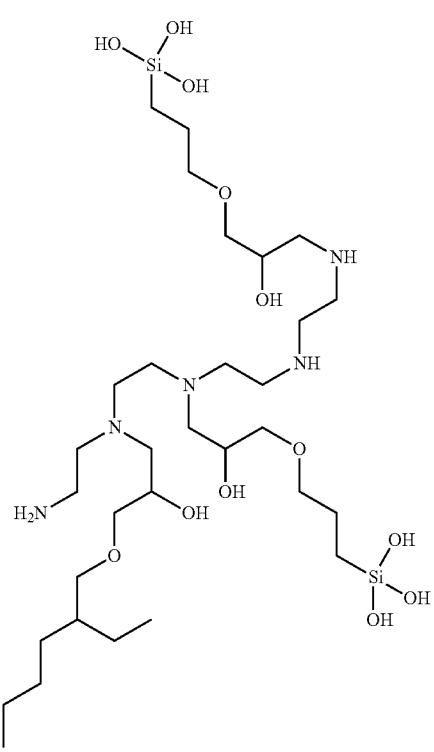
(CIX)
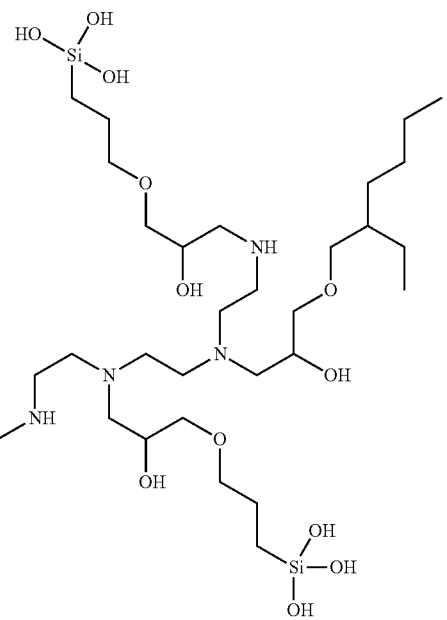
(CX)
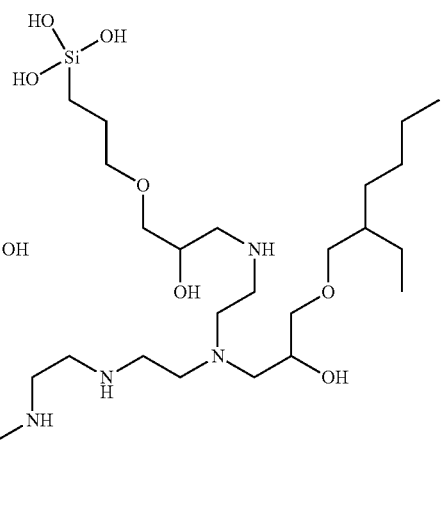
In at least one embodiment the small molecule is selected from the group consisting of: (CXI), (CXII), (CXIII) and (CXIV):

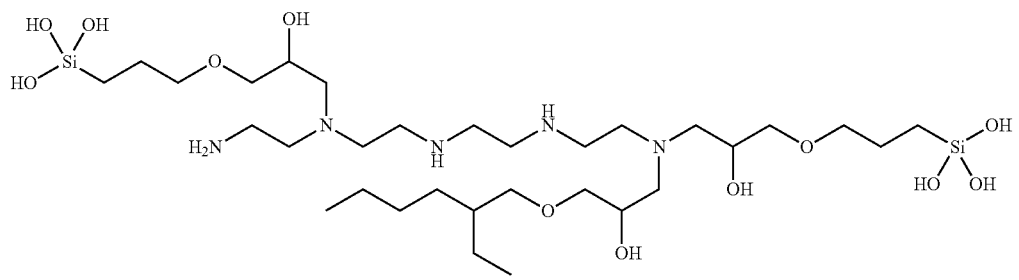
(CXI)
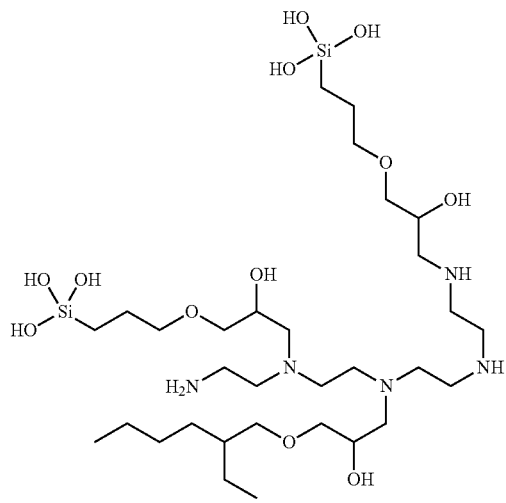
(CXII)
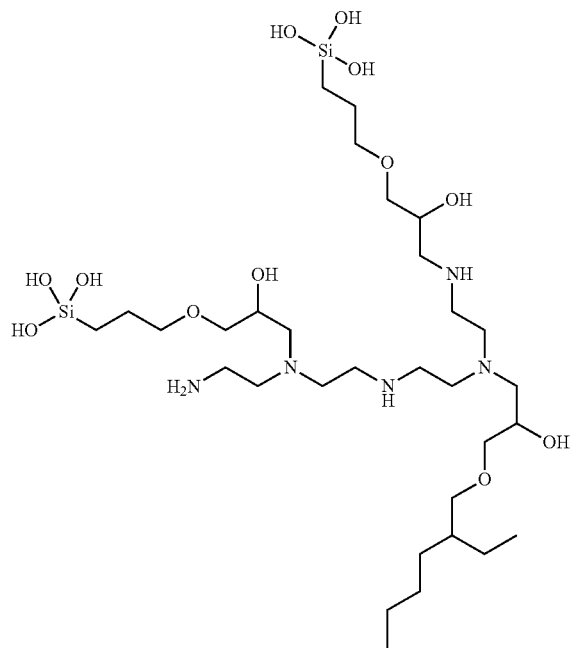
(CXIII)
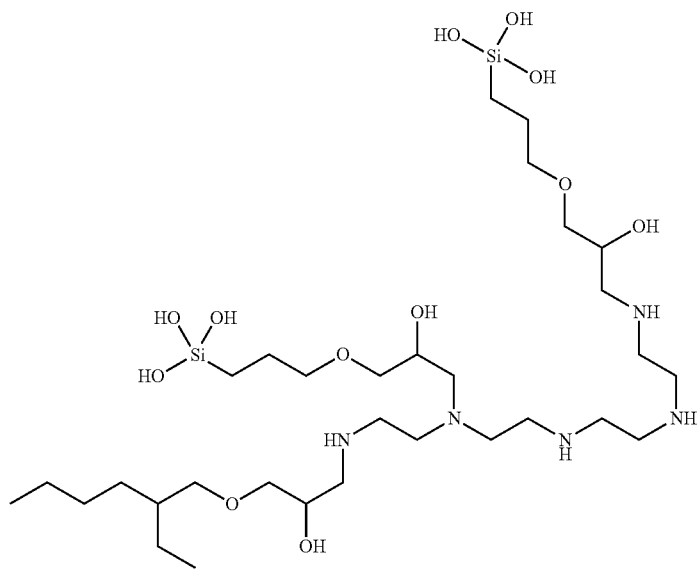
(CXIV)

In at least one embodiment the small molecule is selected from the group consisting of: (CXV), (CXVI) and (CXVII):
(CXV)
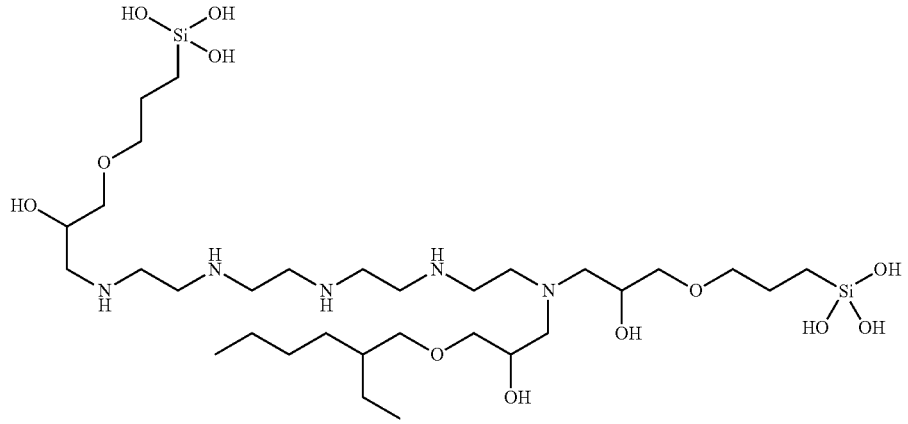
(CXVI)
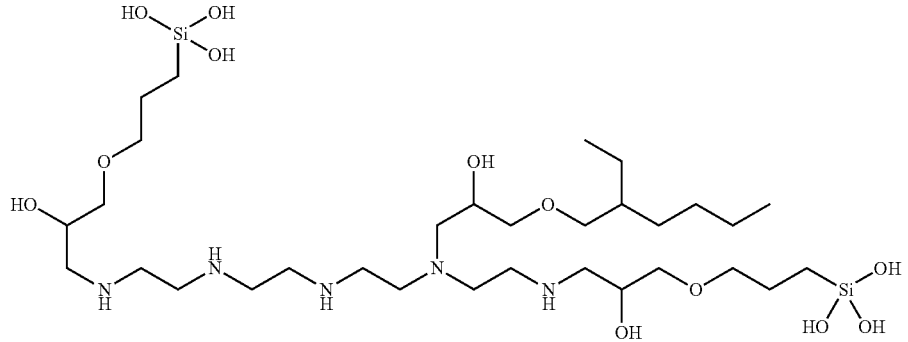

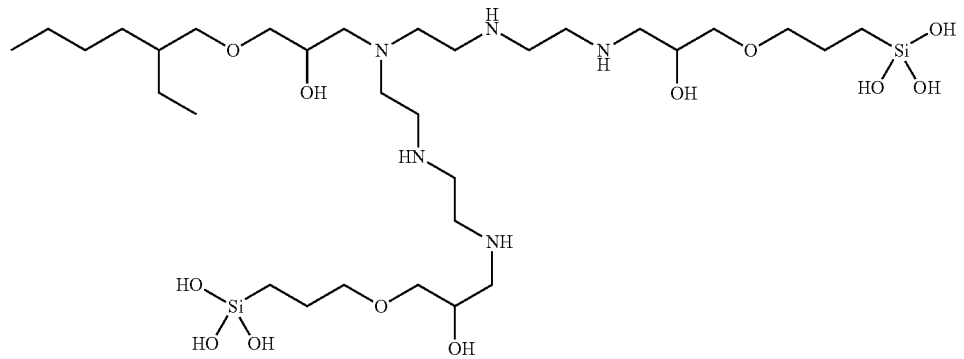
(CXVII)
In at least one embodiment the small molecule is selected from the group consisting of: (CXVIII), (CXIX), (CXX), (CXXI) and (CXXII):
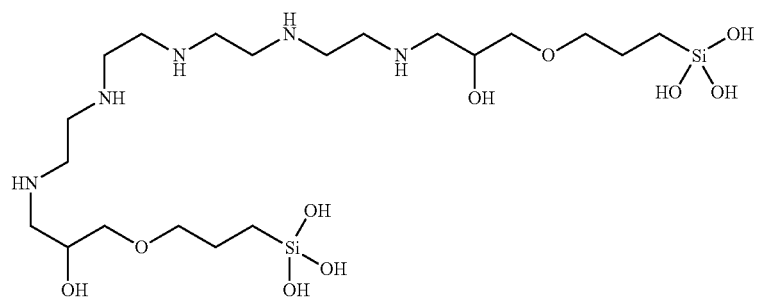
(CXVIII)
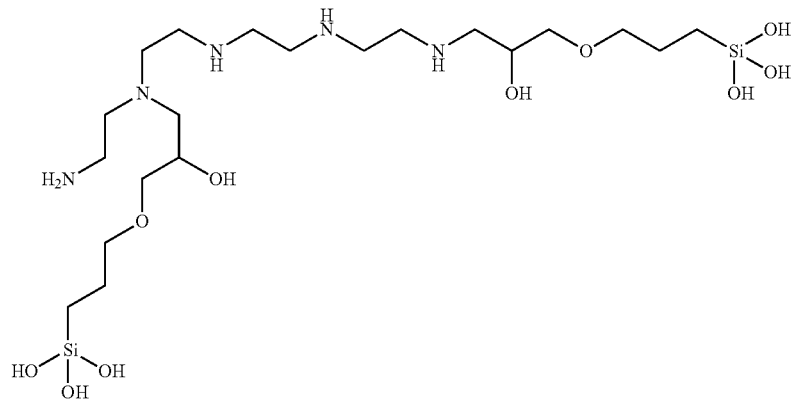
(CXIX)

-continued
(CXX)
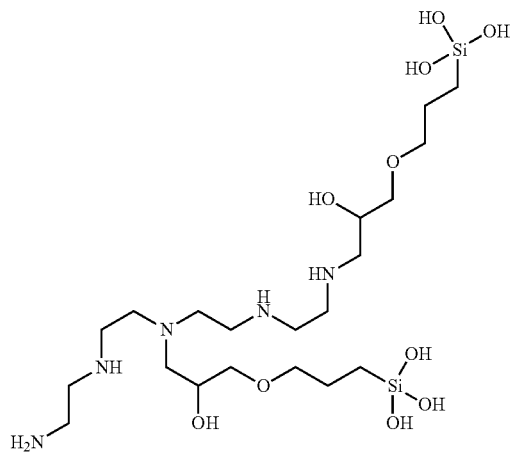
(CXXI)
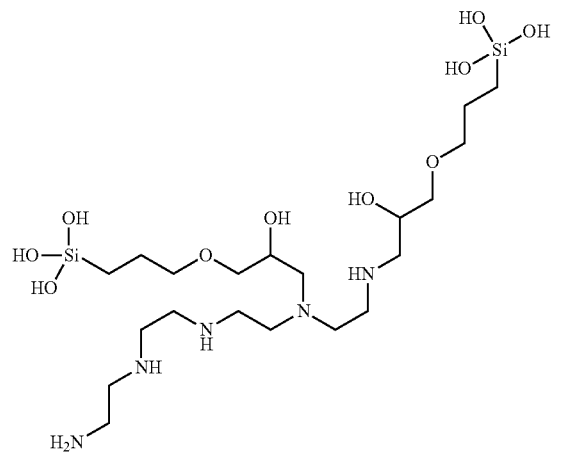
(CXXII)
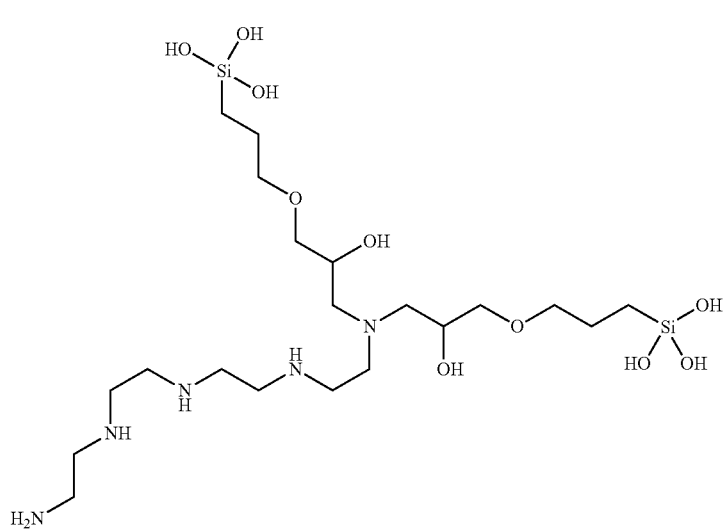

In at least one embodiment the small molecule is selected from the group consisting of: (CXXIII), (CXXIV) and (CXXV):
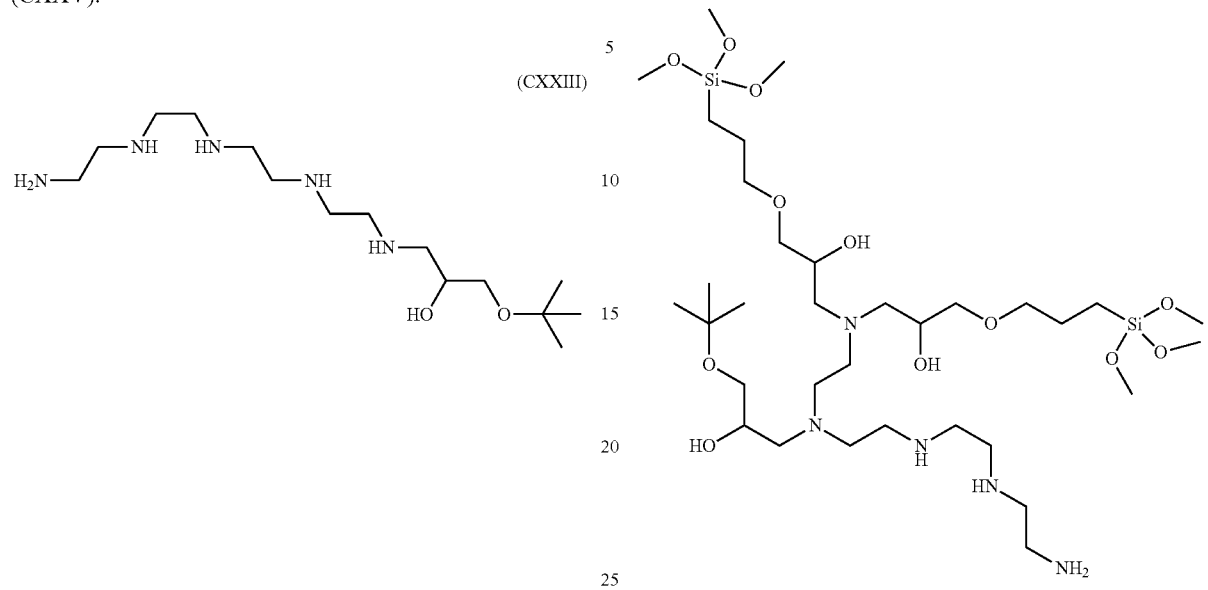
In at least one embodiment the small molecule is selected from the group consisting of: (CXXVI), (CXXVII), (CXXVIII) and (CXXIX):
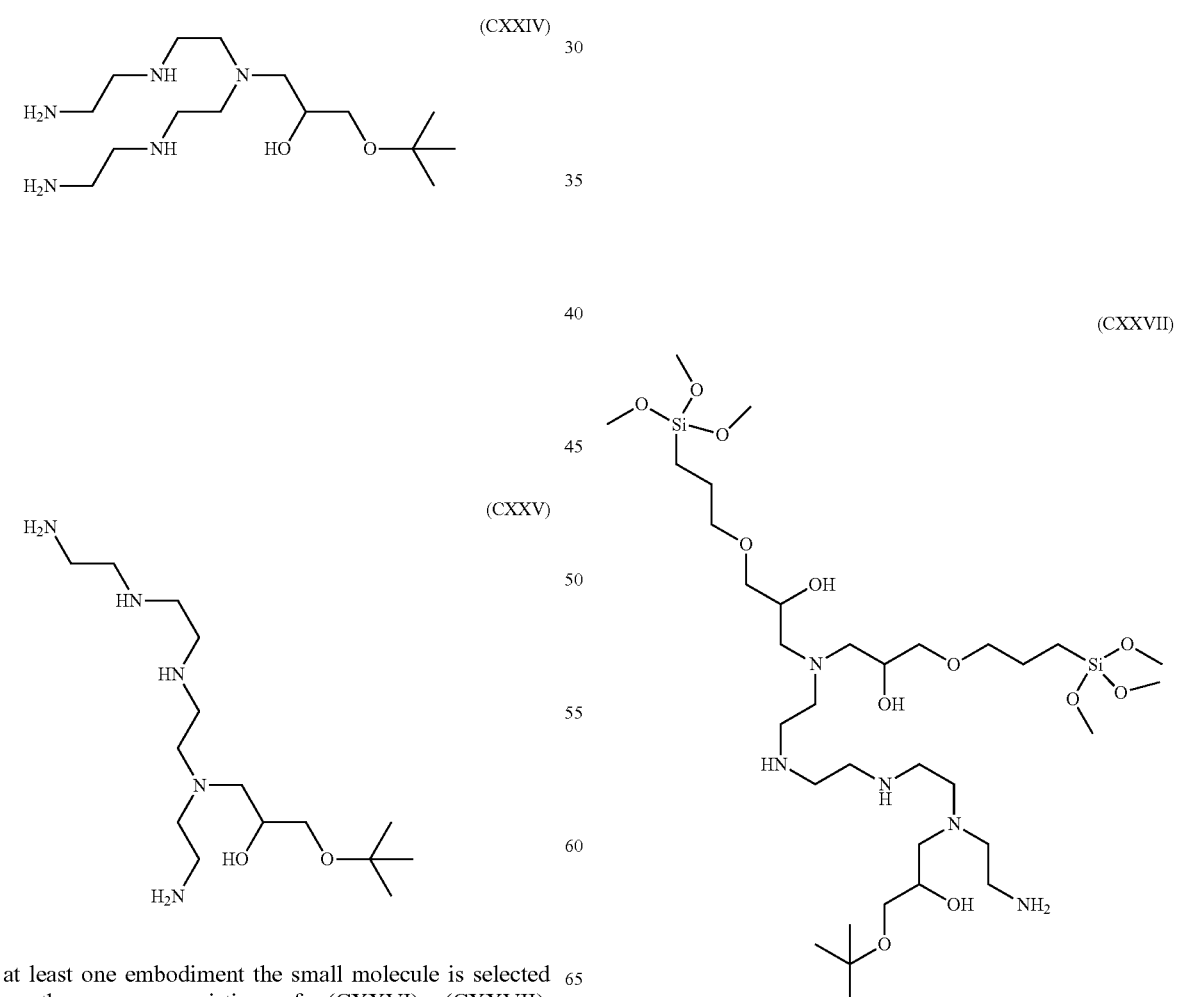

(CXXVIII)
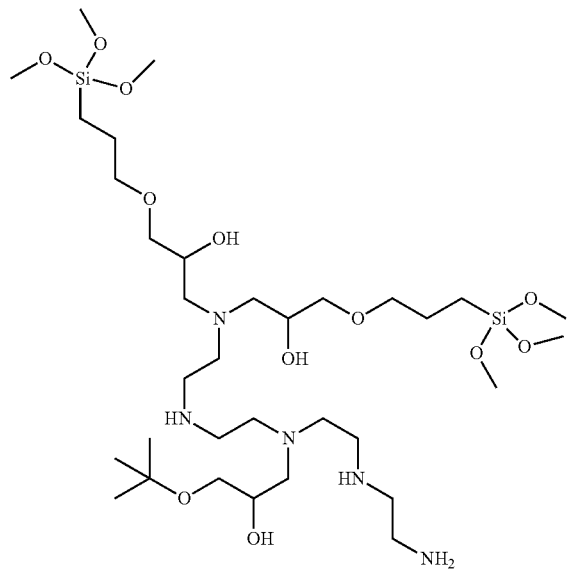
(CXXIX)
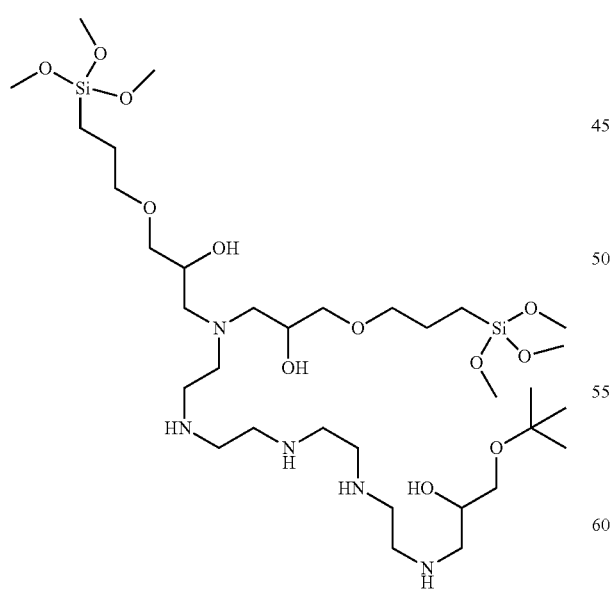
(CXXX)
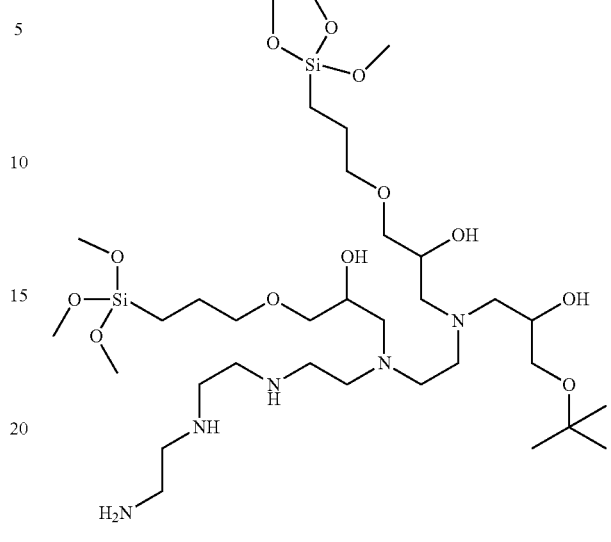
(CXXXI)
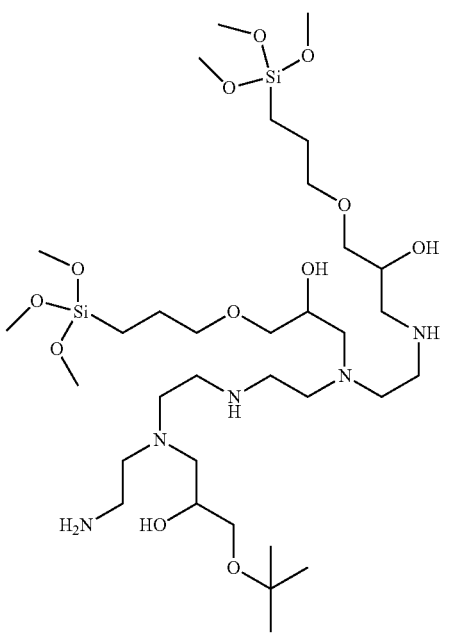
In at least one embodiment the small molecule is selected from the group consisting of: (CXXX), (CXXXI), (CXXXII) and (CXXXIII):

(CXXXII)
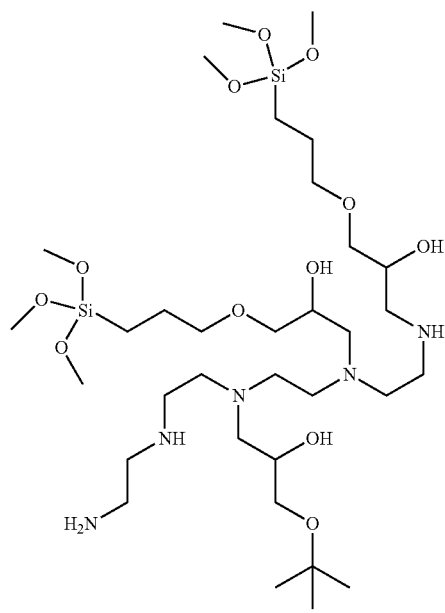
(CXXXIII)
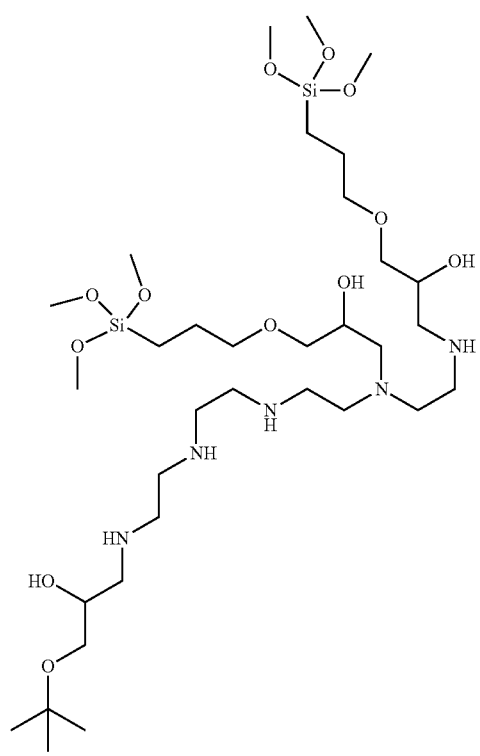
(CXXXIV)
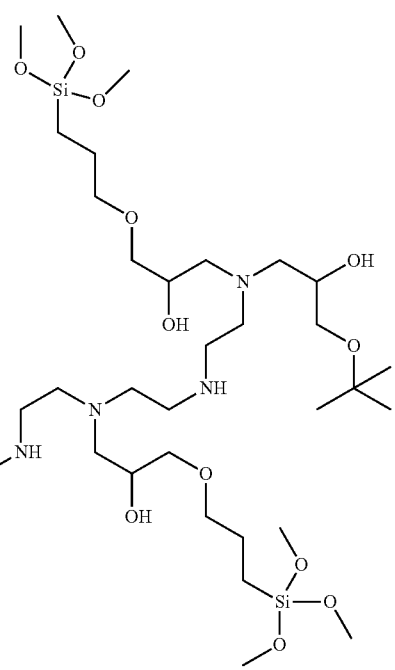
(CXXXV)
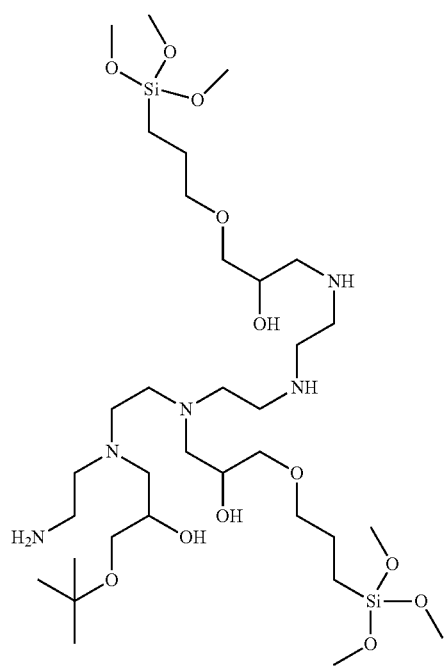
In at least one embodiment the small molecule is selected from the group consisting of: (CXXXIV), (CXXXV), (CXXXVI) and (CXXXVII):

(CXXXVI)
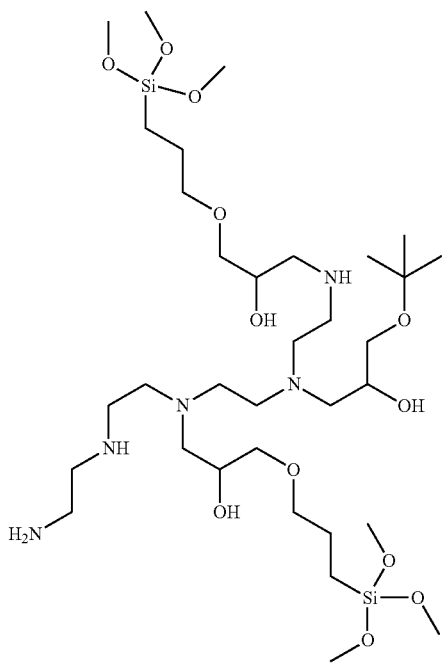
(CXXXVII)
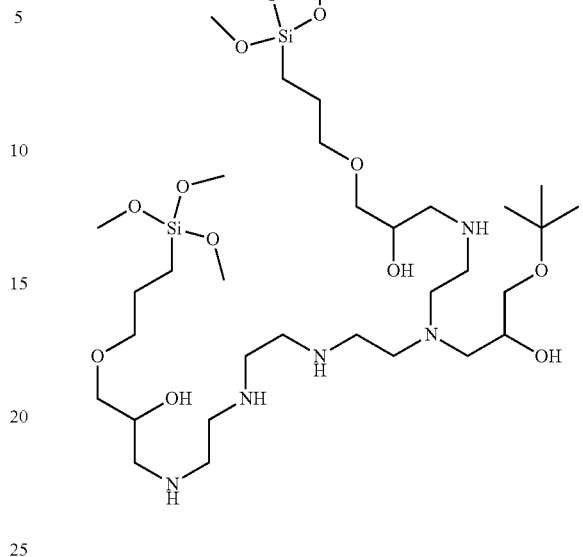
In at least one embodiment the small molecule is selected from the group consisting of: (CXXXVIII), (CXXXIX), (CXL) and (CXLI):
(CXXXVIII)
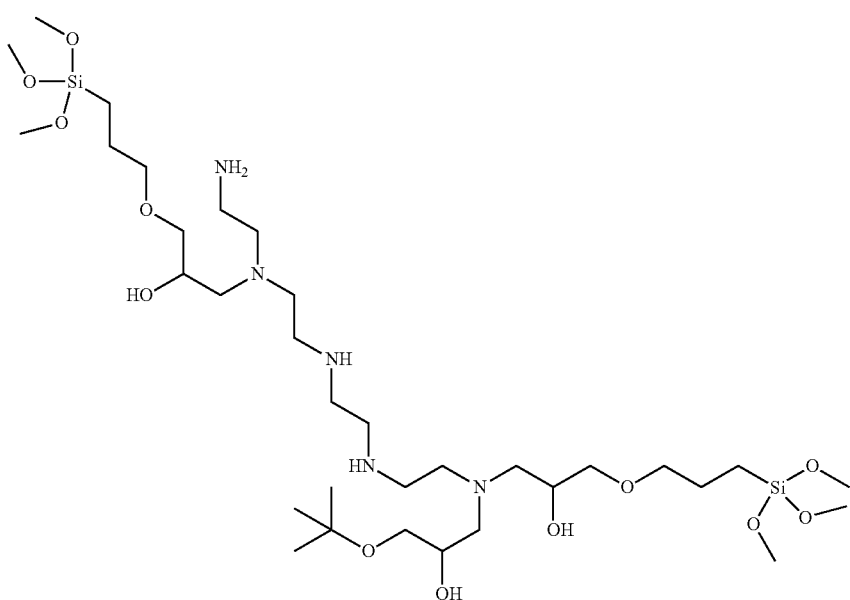

-continued
(CXXXIX)
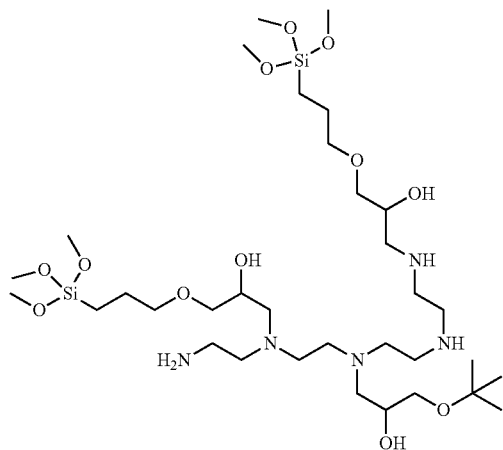
(CXL)
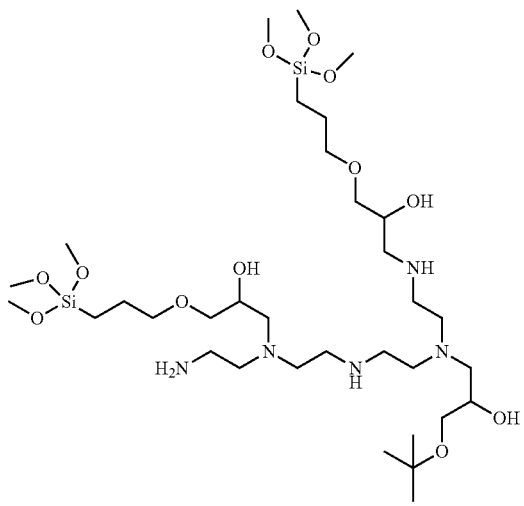
(CXLI)
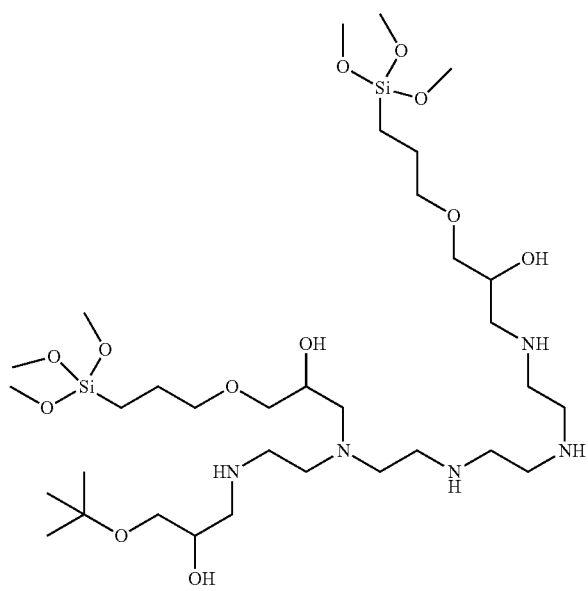

In at least one embodiment the small molecule is selected from the group consisting of: (CXLII), (CXLIII) and (CXLIV):
(CXLII)
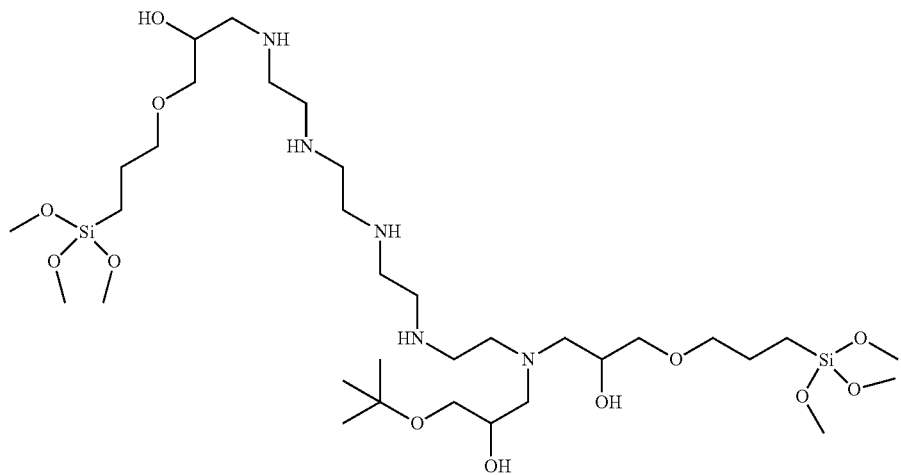
(CXLIII)
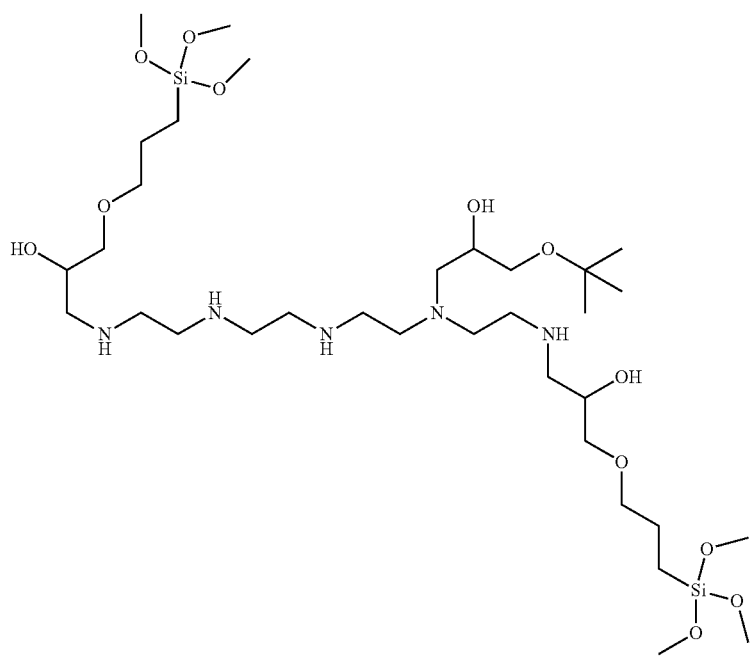
(CXLIV)
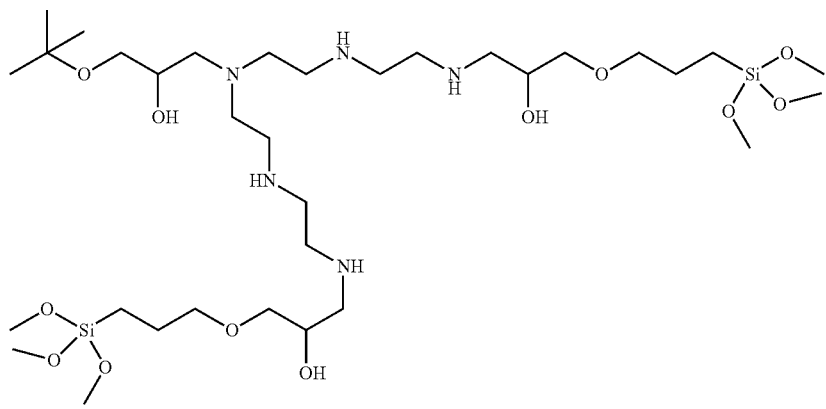

In at least one embodiment the small molecule is selected from the group consisting of: (CXLV), (CXLVI), (CXLVII) and (CXLVIII):
(CXLV)
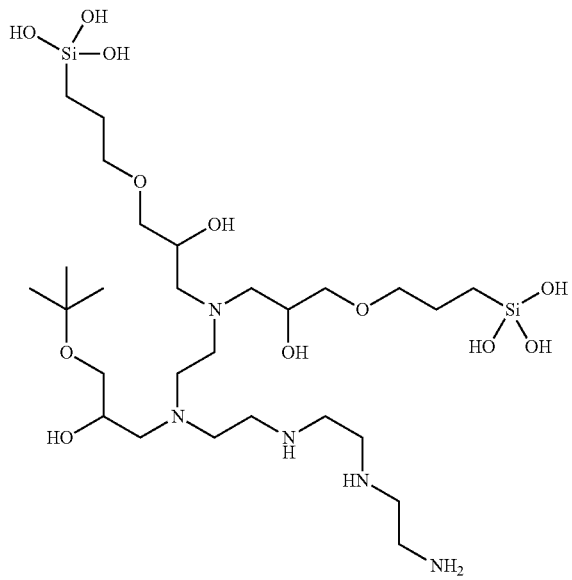
(CXLVII)
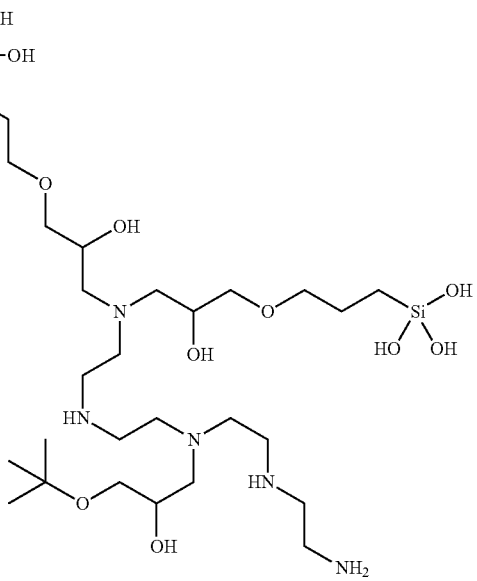
(CXLVI)
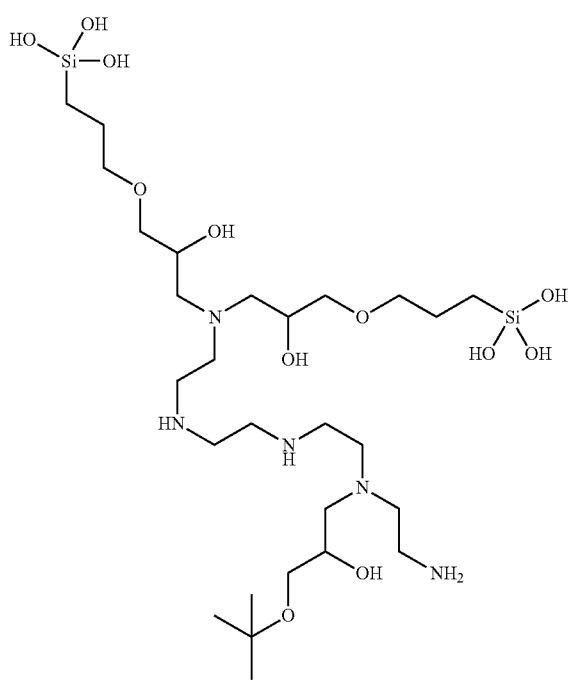
(CXLVIII)
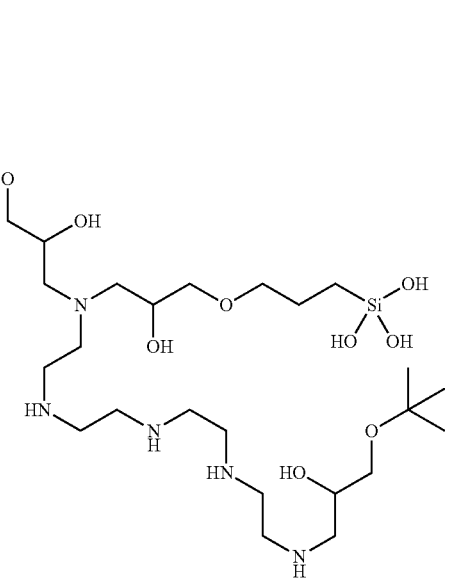
In at least one embodiment the small molecule is selected from the group consisting of (CXLIX), (CL), (CLI) and (CLII):

(CXLIX)
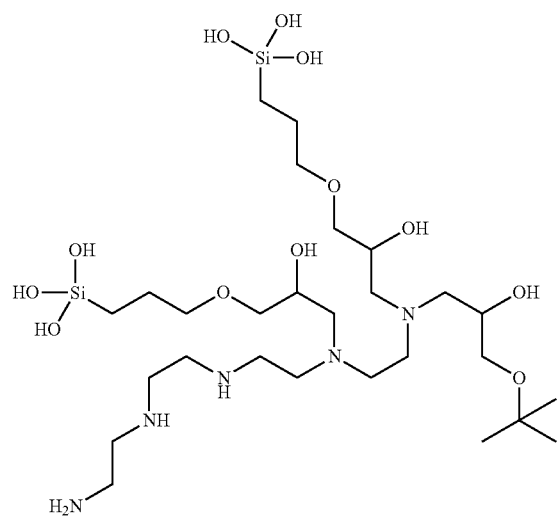
(CLI)
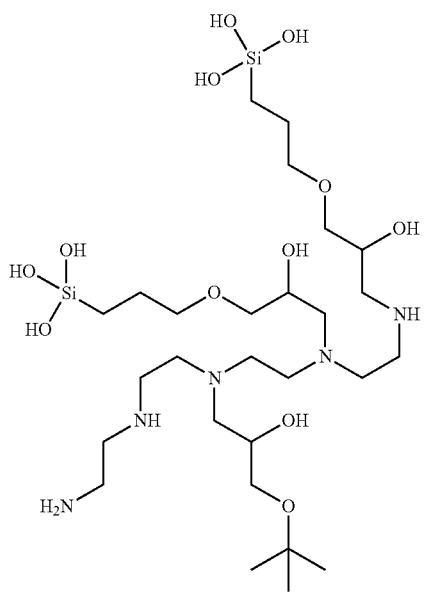
(CL)
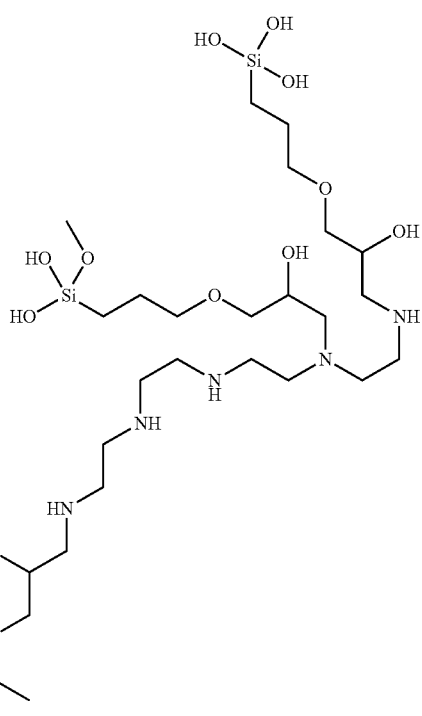
(CLII)
In at least one embodiment the small molecule is selected from the group consisting of (CLIIII), (CLIV), (CLV) and (CLVI):

(CLIII)
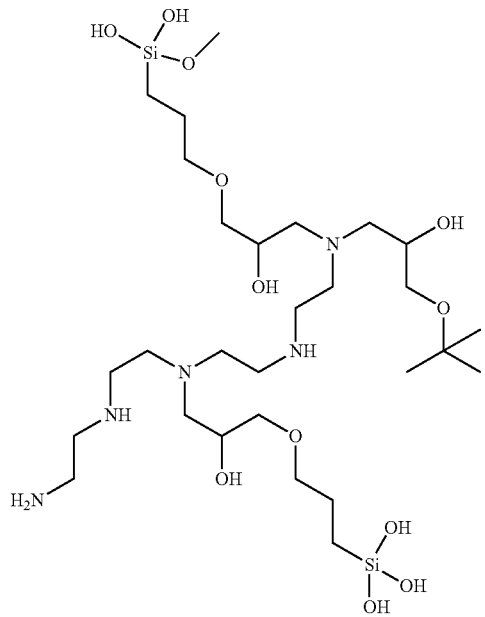
(CLIV)
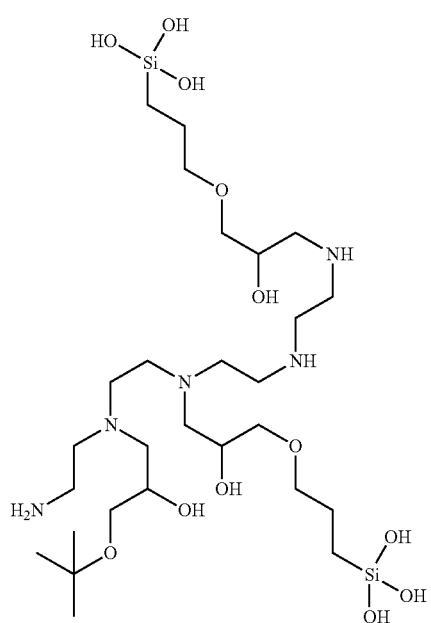
-continued
(CLV)
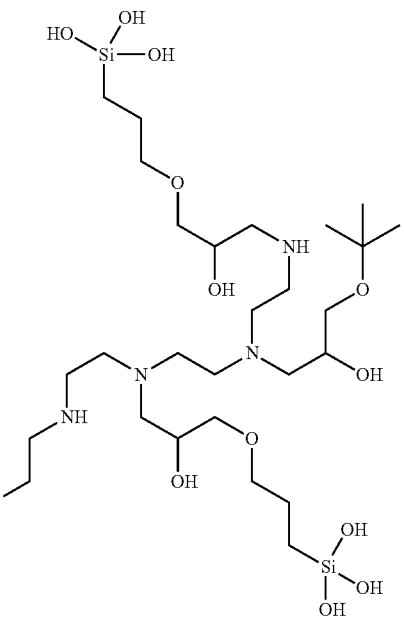
(CLVI)
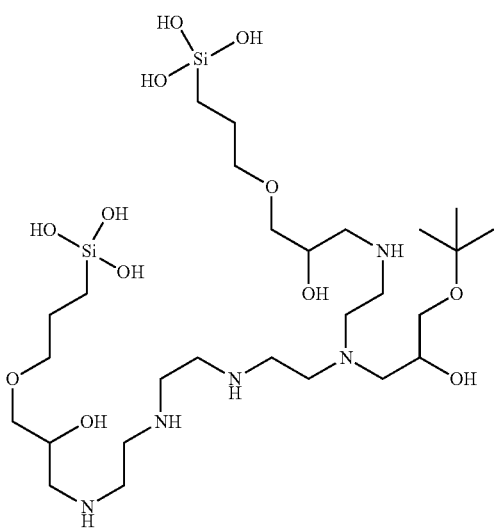
In at least one embodiment the small molecule is selected from the group consisting of: (CLVII), (CLVIII), (CLIX) and (CLX):

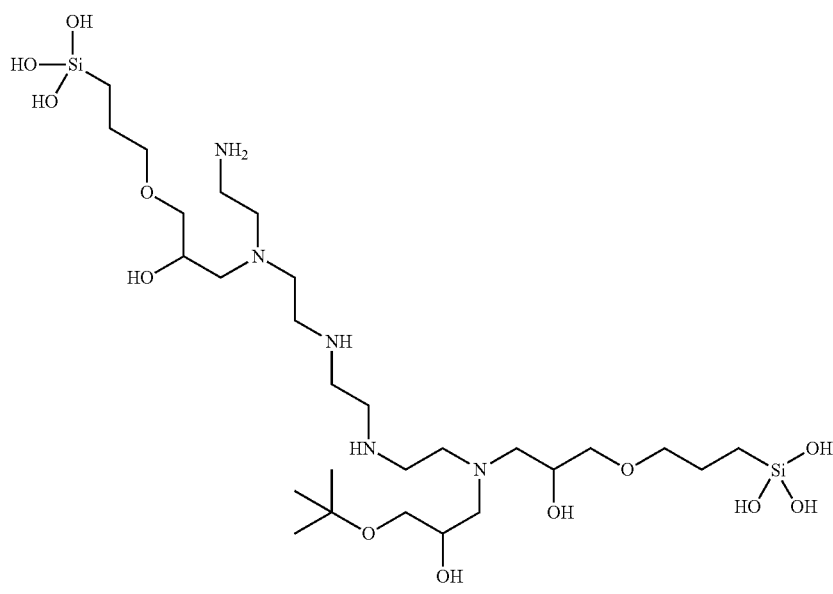
(CLVII)
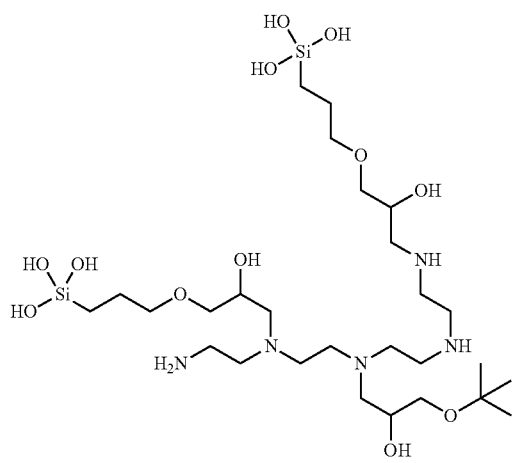
(CLVIII)
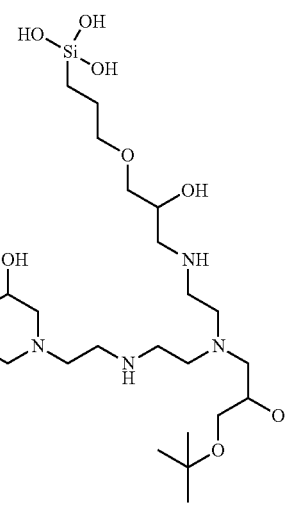
(CLIX)
(CLX)
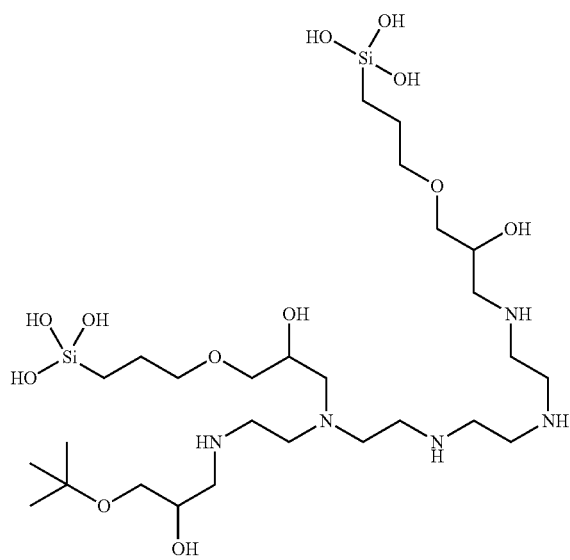

In at least one embodiment the small molecule is selected from the group consisting of: (CLXI), (CLXII), and (CLXIII):

(CLXI)

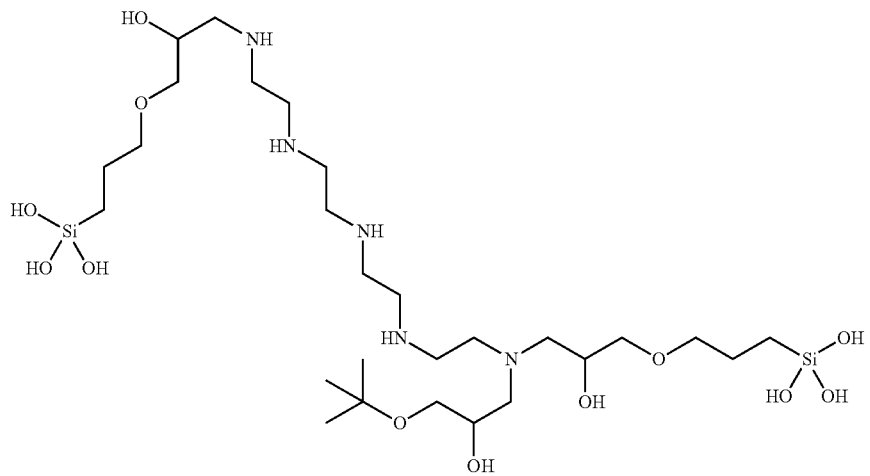

(CLXII)

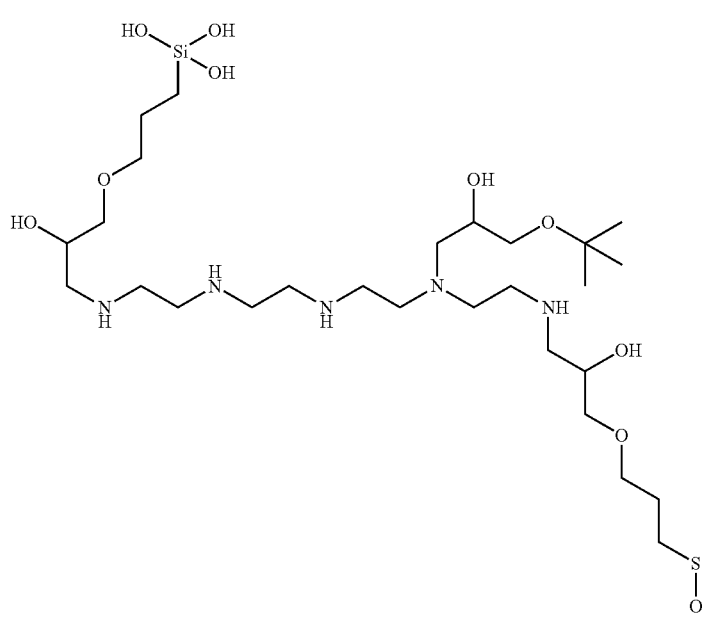

(CLXIII)

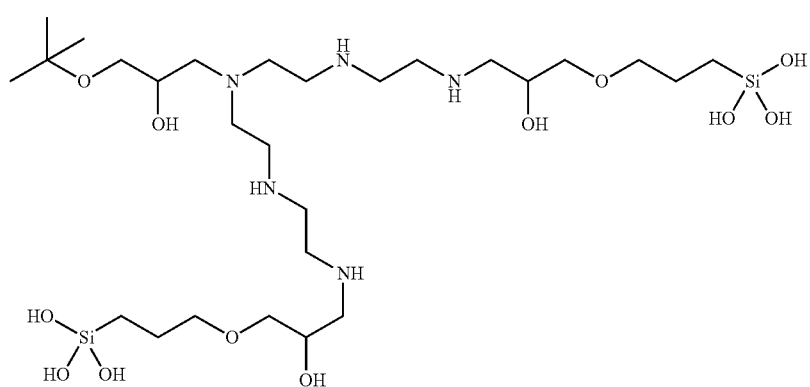

In at least one embodiment the small molecule is present in a solution in an amount ranging from about 0.01 to about 100 wt %. The composition may further comprise one item selected from the list consisting of: amines, activators, antifoaming agents, co-absorbents, corrosion inhibitors, coloring agents, and any combination thereof. The composition may comprise a solvent, the solvent is selected from the group consisting of: water, alcohols, polyols, other industrial solvents, organic solvents, and any combination thereof. The components may be isolated from the reaction in the form of a solid, precipitate, salt and/or crystalline material in pH's ranging from 0 to 14.

Although some of these small molecules have been mentioned in various references, their uses are for entirely unrelated applications and their effectiveness in reducing Bayer Process scale was wholly unexpected. Some places where these or similar small molecules have been mentioned include: U.S. Pat. No. 6,551,515, scientific papers: *Ethylenediamine attached to silica as an efficient, reusable nanocatalyst for the addition of nitromethane to cyclopentenone*, By DeOliveira, Edimar; Prado, Alexandre G. S., *Journal of Molecular Catalysis* (2007), 271(1-2), 6369, *Interaction of divalent copper with two diaminealkyl hexagonal mesoporous silicas evaluated by adsorption and thermochemical data*, By Sales, Jose; Prado, Alexandre; and Airoldi, Claudio, *Surface Science*, Volume 590, Issue 1, pp. 51-62 (2005), and *Epoxide silyant agent ethylenediamine reaction product anchored on silica gel-thermodynamics of cation-nitrogen interaction at solid/liquid interface*, Journal of Noncrystalline Solids, Volume 330, Issue 1-3, pp. 142-149 (2003), international patent applications: WO 2003002057 A2, WO 2002085486, WO 2009056778 A2 and WO 2009056778 A3, French Patents: 2922760 A1 and 2922760 B1, European Patent: 2214632 A2, and Chinese patent application: CN 101747361.

The effectiveness of these small molecules was unexpected as the prior art teaches that only high molecular weight polymers are effective. Polymer effectiveness was presumed to depend on their hydrophobic nature and their size. This was confirmed by the fact that cross-linked polymers are even more effective than single chain polymers. As a result it was assumed that small molecules only serve as building blocks for these polymers and are not effective in their own right. (WO 2008/045677 [0030]). Furthermore, the scientific literature states "small molecules containing" . . . "[an] Si—O₃ grouping are not effective in preventing sodalite scaling" . . . because . . . "[t]he bulky group" . . . "is essential [in] keeping the molecule from being incorporated into the growing sodalite." *Max HT™ Sodalite Scale Inhibitor: Plant Experience and Impact on the Process*, by Donald Spitzer et. al., Page 57, *Light Metals* 2008, (2008). However it has recently been discovered that in fact, as further explained in the provided examples, small molecules such as those described herein are actually effective at reducing DSP scale.

It is believed that there are at least three advantages to using a small molecule-based inhibitor as opposed to a polymeric inhibitor with multiple repeating units of silane and hydrophobes. A first advantage is that the smaller molecular weight of the product means that there are a larger number of active, inhibiting moieties available around the DSP seed crystal sites at the DSP formation stage. A second advantage is that the lower molecular weight allows for an increased rate of diffusion of the inhibitor, which in turn favors fast attachment of the inhibitor molecules onto DSP seed crystals. A third advantage is that the lower molecular weight avoids high product viscosity and so makes handling and injection into the Bayer process stream more convenient and effective.

The invention further relates to the synthesis of new small molecule chemical entities that show surprisingly improved performance for the inhibition of DSP scale in Bayer liquor compared to those previously disclosed. In this work, the extension of the diamine structure by increasing the number of reactive nitrogen groups to between 3 to 5 with spacing by one, two or three alkylene groups (e.g., ethylene or propylene) as indicated by the general structure below, has resulted in remarkably improved rates of adsorption of the inhibitor onto DSP seed surfaces as well as DSP scale inhibition performance over earlier compositions, for example those based on hexane diamine, ethylene diamine and 1-amino-2-propanol.

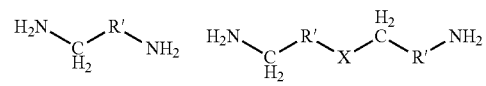

where R'=CH₂, or, CH₂—CH₂; and X=NH2, NH2-R'—NH2, or NH2-R'—NH2-R'—NH2

Thus, the following readily available amine compounds (A) (from Sigma-Aldrich), can be used:

N¹-(2-aminoethyl)ethane-1,2-diamine, commonly known as diethylenetriamine, (DETA), N¹-(3-aminopropyl)propane-1,3-diamine, commonly known as dipropylenetriamine, (DPTA), N¹,N¹'-(ethane-1,2-diyl)bis(ethane-1,2-diamine), commonly known as triethylenetetramine, (TETA), N¹,N¹'-(propane-1,3-diyl)bis(propane-1,3-diamine), commonly known as triproylenetetramine, (TPTA), N¹-(2-aminoethyl)-N²-(2-((2-aminoethyl)amino)ethyl)ethane-1,2-diamine, commonly known as tetraethylenepentamine, (TEPA).

The preferred synthesis for the formation of these new A:G:E chemical entities involves the reaction of the amine with component G first (in an amount ranging between 1.0-2.5 mole ratio to amine) followed by the reaction with component E (in an amount ranging between 0.5-2.0 mole ratio to amine) in a semi-batch method.

A preferred A:G:E compositions range, in general, having mole ratios of between:

About 1.0:1.0:0.5 to about 1.0:3.0:2.0 A:G:E and more preferred compositions with mole ratio of:

About 1.0:1.0:0.5 to about 1.0:2.0:1.0 A:G:E and most preferred are compositions with mole ratio of:

About 1.0:2.0:0.8 A:G:E.

The improved DSP scale inhibition performance for these compositions over early small molecules are surprising from the following aspects:

1. The A:G:E complexes or adducts have low molecular weights (<1000 g/mole) compared to the silane substituted highly polymeric structures based on polyacrylate acrylamide copolymers or polyethyleninimine polymers disclosed in the prior art, and, more specifically including the chemistries disclosed as examples in the Cytec patent application WO/045677 A1 involving silane substituted polyamines or amine mixtures that have been extensively cross-linked using epichlorohydrin.

2. The small molecule silane containing A:G:E complexes (or adducts) have a unique structure compared to the 0.5 mole % silane substituted polymers disclosed in the prior art. The preferred order of addition of the component G followed by the component E leads to a more preferred spatial arrangement or distribution of the silane group with respect to the more hydrophobic E group in the small molecule, compared to a totally random distribution of G and E that would be anticipated from in a true batch reaction.

It should be noted that an obvious extension of this invention is that combinations of A:G:E compositions can also be added as mixtures as an inhibiting amount for reduction of aluminosilicate scale.

In at least one embodiment these small molecules can be isolated as the unhydrolized alkoxysilane, protected with methyl or ethyl ether groups. These compounds can be sold and transported to the customer site as a dry granular-product instead of as a caustic solution (liquid). This can provide the following benefits over exiting scale inhibitors:
  Lower transportation costs and delivery of high actives products
  Significantly lower environmental and human exposure hazards during manufacture, transportation and handling due to non-hazardous solid gel compared to a potentially corrosive caustic solution.

These compounds can be hydrolyized on-site at a 0.01-50% concentration, more preferably between 0.01-25% and most preferably between 0.1-10% concentration in a caustic solution containing between 5-100 gpL sodium hydroxide and more preferably between 5-50 g/L and most preferably in a caustic solution containing between 5-25 gpL, sodium hydroxide, or they can be hydrolyzed directly in-situ in the Bayer process, in either case, hydrolysis of the alkyl ether on the silane occurs to form the—corresponding hydroxysilane compound(s) with —Si—(OH)$_3$ groups which are readily soluble in the caustic and Bayer solutions.

In some embodiments, a further improvement in scale inhibition performance is achieved using A:G:E compositions synthesized as described above and further treating the resulting mixture of compounds with a very small amount of a di-oxirane coupling agent, e.g., those available from CVC Thermoset Specialties. The di-oxirane coupling agent may have the general structure:

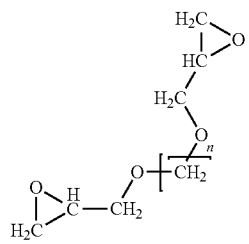

where n =1, 2, 4, or 6.

Desirably, the di-oxirane coupling agent may be any of the following:
  Ethylene glycol diglycidyl ether ("EGDGE"),
  1,4-butanediol diglycidyl ether,
  1,6-hexanediol diglycidyl ether,
  propylene glycol diglycidyl ether
and combinations thereof.

Post addition of between about 0.2 to about 0.5 mole % of the coupling agent is expect to form portions of a dimer having the general structure:

[A:G:E]$_2$:X

Trace amounts of extended adduct, for example, trimeric species, tetrameric, etc., compounds might also be formed in the process however, addition of too much of the di-oxirane coupling agent results solids that are not readily soluble in caustic solution. It is important that the composition be readily soluble in caustic to ensure successful application in the Bayer process liquor.

The preferred A:G:E:X compositions range, in general, having mole ratios of between:
  About 1.0:1.0:0.5:0.2 to about 1.0:2.5:2.0:0.5 A:G:E:X
and more preferred are compositions with mole ratio of between:

About 1.0:1.5:0.5:0.25 to about 1.0:2.0:1.0:0.5 A:G:E:X and even more preferred are compositions with mole ratio of between
  About 1.0:2.0:0.8:0.25 to about 1.0:2.0:0.5:0.5
and most preferred are compositions with mole ratio of about:
  1.0:2.0:0.8:0.25 A:G:E:X.

Below is a schematic of at least one possible compound, where R independently represents H, alkyl, alkylamine, inorganic and organic species such as salts, ethers, anhydrides etc. in the possible mixture of small molecules that are formed in these reactions.

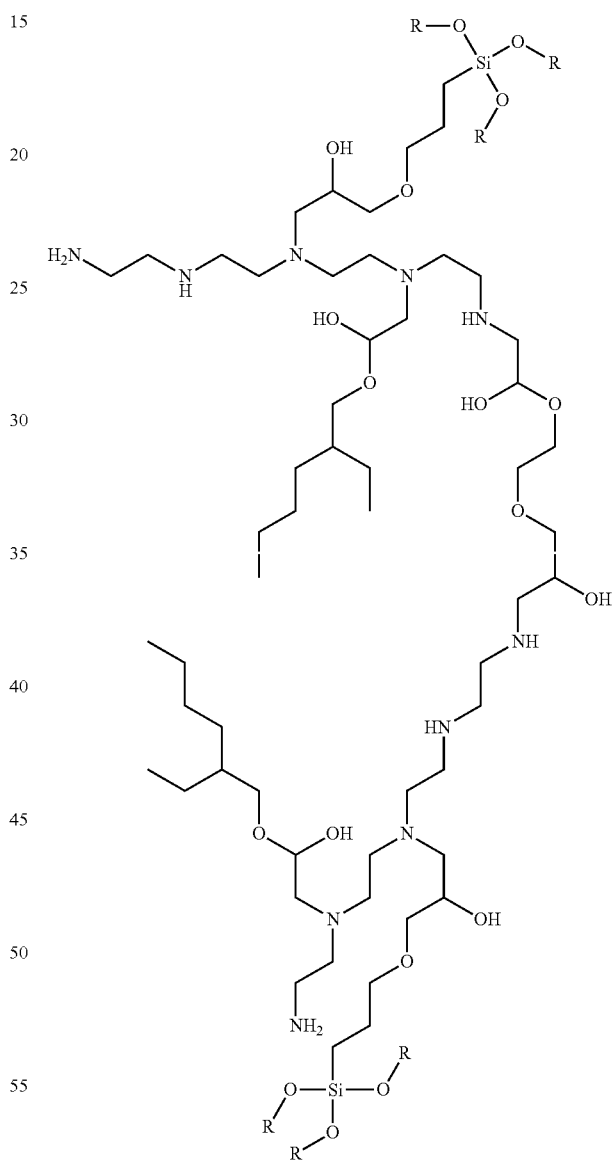

In at least one embodiment these small molecules can be isolated as the unhydrolized alkoxysilane, protected with methyl or ethyl ether groups. These compounds can be sold and transported to the customer site as a dry granular product instead of as a caustic liquid solution. This can provide the following benefits over exiting scale inhibitors:
  Lower transportation costs and delivery of high actives products Significantly lower environmental and human exposure hazards during manufacture, transportation and handling due to non-hazardous solid gel compared to a potentially corrosive caustic solution.

These compounds can be hydrolyzed on-site at a 0.01-50.0% concentration, more preferably between 0.01-25% and most preferably between 0.1-10% concentration in a caustic solution containing between 5-100 gpL sodium hydroxide and more preferably between 5-50 g/L and most preferably in a caustic solution containing between 5-25 g/L sodium hydroxide, or they can be hydrolyzed directly in-situ in the Bayer process, in either case, hydrolysis of the alkyl ether on the silane occurs to form the now soluble hydroxysilane compound(s) with —Si—(OH)$_3$ groups.

EXAMPLES

The foregoing may be better understood by reference to the following examples, which are presented for purposes of illustration and are not intended to limit the scope of the invention.

I. Example of a Synthesis Reaction A, E and G.

In a typical synthesis reaction the three constituents: A (e.g., hexane diamine), G (e.g. 3-glycidoxypropyltrimethoxysilane) and E (e.g. ethyl hexyl glycidyl ether) are added to a suitable reaction vessel at a temperature between 23-40° C. and allowed to mix. The reaction vessel is then warmed to 65-70° C. during which time the reaction begins and a large exotherm is generated. The reaction becomes self-sustaining and depending on the scale of the reaction, can reach temperatures as high as 125 to 180° C. Typically the reaction is complete after 1 to 2 hours and then the mixture is allowed to cool down. As an aspect of this invention this un-hydrolyzed product mixture can be isolated as a liquid or gel or a solid in a suitable manner. Alternatively, the reaction product mixture can be hydrolyzed, via a number of methods, to prepare a solution of the hydrolyzed product mixture in water. The hydrolysis of the alkoxysilane groups in the component G results in the formation of the corresponding alcohol (e.g methanol, ethanol etc., depending on the akloxysilane used in the synthesis).

It is common to those skilled in the art to conduct the ring opening of an epoxide with a reactive amine in a batch mode (where the components are mixed together), heated to an initiation temperature above room temperature (e.g. 50-65° C.) with the reaction temperatures allowed to reach as high as 125 to 180° C. This can cause internal cross-linking and side reactions to occur—which is often desired in the resin manufacturing processes.

However, at least one embodiment involves the use of a continuous or semi-batch synthesis method which provides several advantages over the batch process commonly used. This involves adding only a portion of the G and E constituents either together or sequentially or individually in a form of a slow feed to initiate the primary epoxide ring opening reaction, followed by the slow continuous feeding of the two constituents G and E (either together or separately and at the same time or sequentially). This method allows for a much better control over the overall reaction, the reaction temperature and provides a better overall yield of the active compounds in the product also avoiding the undesired side reactions.

In at least one embodiment the synthesis reaction utilizes constituent G=3-glycidoxypropyltrimethoxysilane. Prolonged exposure at high temperatures above 120° C. can result in internal coupling reactions and multiple substitutions with the reactive amine groups such as hexane diamine or ethylene diamine. The resulting un-hydrolyzed reaction products will turn to a gel over shorter time period accompanied by an increase in the reaction product viscosity. Use of a semi-batch process or continuous or separate or slow sequential or individual or combined feed of the E and G epoxides into the reaction mixture allows better control of the reaction temperature thereby reducing the amount of methanol that is generated and isolated during the reaction. Furthermore the reaction mixture has a lower viscosity and accounts for fewer undesired side reactions (see Table 1).

TABLE 1

Synthesis Reaction Data for A:G:E reactions by various methods

| Batch # | Method | Reaction Temp F. | Viscosity of Reaction Intermediate, cps | MeOH Isolated, lbs |
| --- | --- | --- | --- | --- |
| 1 | Batch | 240-265 | 550 | 9.8 |
| 2 | Batch on Batch | 225-235 | 240 | 1.6 |
| 3 | Semi-Batch | 180-200 | 65 | 0.7 |

Examples of the Relative DSP Scale Inhibition of Various A:G:E Small Molecules Formed During the Synthesis Reaction Disclosed Above.

The scale inhibition performance of the small molecule is typically performed as follows:

1) A small amount of sodium silicate (0.25-1.5 g/L as SiO$_2$) is added to a Bayer refinery spent liquor at room temperature to raise the silica concentration in the liquor.
2) Portions of this liquor sample are dosed with varying amounts of the new scale inhibitor compound or mixture.
3) Dosed and untreated (or Blank) liquor samples are subjected to elevated temperatures between 96 to 105° C. for 4 to 6 hours.
4) Samples are then cooled and the amount of DSP scale formed in each of the dosed liquors samples are measured and compared to that formed in the untreated or blank samples.

As an example, Table 2 shows the relative DSP Scale Inhibition for several A:G:E synthesized mixtures using the synthesis reaction disclosed earlier, with various amine constituents as the core.

TABLE 2

Relative DSP Scale Inhibition for Various A:G:E
Synthesized Reaction Mixtures, where
A = Amine
G = Glycidoxypropyltrimethoxysilane
E = 2-Ethylhexyl glycidyl ether

| A:G:E Compounds A = Amine Used | Amount of DSP Scale mg, versus Treatment | | | % Reduction in DSP Scale versus Blank | |
|---|---|---|---|---|---|
| | Un-treated | Low Dose | High Dose | Low Dose | High Dose |
| Hexane Diamine | 26.20 | 0.18 | 0.06 | 99.3% | 99.8% |
| Ethylene Diamine | 27.30 | 20.40 | 8.12 | 25.3% | 70.3% |
| Diethylene Triamine | 26.70 | 18.30 | 10.27 | 31.5% | 61.5% |
| Tetraethylene pentaamine | 24.60 | 22.50 | 16.80 | 8.5% | 31.7% |
| 1-amino-2-propanol | 26.20 | 3.50 | 0.05 | 86.6% | 99.8% |

As an example but not limiting the scope of this invention, is the synthesis and improved DSP scale inhibition performance for a series of new TEPA:G:E and TEPA:G:E:EGDGE adduct compositions examples of which are given in Table 3 below.

TABLE 3

New Amine:G:E chemistries and [Amine:G:E]2-X adducts as DSP Scale Inhibitors

| Sample ID | Amine | Mole Ratio Amine | Mole Ratio G | Mole Ratio E | Mole Ratio EGDGE |
|---|---|---|---|---|---|
| 1 | HMDA | 1 | 1 | 0.8 | 0 |
| 2 | MIPA | 1 | 1 | 0.8 | 0 |
| A | TEPA | 1 | 1 | 1.0 | 0 |
| B | TEPA | 1 | 1 | 1.0 | 0.25 |
| C | TEPA | 1 | 2 | 0.8 | 0 |
| D | TEPA | 1 | 2 | 0.8 | 0.25 |
| E | TEPA | 1 | 2 | 0.8 | 0.5 |
| F | TEPA | 1 | 2 | 0.5 | 0.5 |
| G | TEPA | 1 | 3 | 0.8 | 0 |
| H | TEPA | 1 | 3 | 0.8 | 0.25 |
| I | TEPA | 1 | 2 | 0.5 | 0 |
| J | TEPA | 1 | 2 | 0.5 | 0.25 |

Table 4 shows the % decrease in net DSP scale for the 1.0:2.0:0.8 mole ratio TEPA:G:E chemistry (sample C) and corresponding coupled adduct with 0.25 mole ratio EGDGE (sample D) and over the 1.0:1.0:0.8 mole ratio HDA:G:E C compositions (sample 1) disclosed previously.

TABLE 4

Efficacy results as related to decrease in net DSP

| Sample | Dose ppm | Mass 1, g | Mass 2, g | Avg. DSP, g | Std. D. | Net DSP, g | Decrease in Net DSP |
|---|---|---|---|---|---|---|---|
| Control | | 0.3220 | 0.3312 | 0.3266 | 0.0046 | 0.3266 | x |
| Control DSP | 0 | 0.5199 | 0.4939 | 0.5119 | 0.0127 | 0.4119 | 0 |
| 1 | 30 | 0.4015 | 0.3933 | 0.3974 | 0.0041 | 0.2974 | 27.9% |
| C | 30 | 0.3091 | 0.3148 | 0.3120 | 0.0028 | 0.2120 | 48.5% |
| C | 40 | 0.2706 | 0.2822 | 0.2764 | 0.0058 | 0.1764 | 57.2% |
| C | 60 | 0.2399 | 0.2416 | 0.2408 | 0.0009 | 0.1408 | 65.8% |
| D | 30 | 0.2226 | 0.2215 | 0.2221 | 0.0006 | 0.1221 | 70.4% |

Table 5 shows how the adsorption rate of the new 1.0:2.0:0.8 mole ratio TEPA:G:E composition (sample C) applied at a constant dose over various contact times with DSP seed crystals is significantly faster than that found for the previously disclosed 1.0:1.0:0.8 mole ratio HMDA:G:E (sample 1) scale inhibitor.

TABLE 5

Efficacy results versus time at a constant dosage of inhibitor

| Sample | Contact Time, min. | Mass 1, g | Mass 2, g | Avg. DSP, g | Std. D. | Net DSP, g | Decrease in Net DSP |
|---|---|---|---|---|---|---|---|
| Control | — | 0.0462 | 0.0619 | 0.0541 | 0.0079 | 0.0541 | x |
| Control DSP | — | 0.3090 | 0.3041 | 0.3284 | 0.0310 | 0.1284 | 0 |
| C | 2 | 0.2984 | 0.3010 | 0.2997 | 0.0013 | 0.0997 | 22.3% |
| C | 5 | 0.2595 | 0.2746 | 0.2671 | 0.0075 | 0.0671 | 47.7% |
| C | 8 | 0.2415 | 0.2528 | 0.2472 | 0.0057 | 0.0472 | 63.2% |
| 1 | 2 | 0.3166 | 0.3200 | 0.3183 | 0.0017 | 0.1183 | 7.9% |
| 1 | 5 | 0.2944 | 0.2795 | 0.2870 | 0.0074 | 0.0870 | 32.2% |
| 1 | 8 | 0.2627 | 0.2764 | 0.2696 | 0.0069 | 0.0696 | 45.8% |

Table 6 shows the continuous reduction in net DSP scale formation as a function of the dosage applied of the small molecule sample C from 0 to 80 ppm as product. Complete scale inhibition was found at dosages above 80 ppm.

TABLE 6

Complete inhibition of DSP by sample C

| Dose, ppm | Mass 1, g | Mass 2, g | Mass 3, g | Avg. DSP, g | Std. D. | % DSP Precipitated |
|---|---|---|---|---|---|---|
| 0 Control | 0.2904 | 0.2754 | 0.2798 | 0.2819 | 0.0063 | 100.0 |
| 20 | 0.1330 | 0.1479 | | 0.1405 | 0.0075 | 49.8 |
| 30 | 0.0663 | 0.0924 | | 0.0794 | 0.0131 | 28.2 |
| 40 | 0.0219 | 0.0270 | | 0.0245 | 0.026 | 8.7 |
| 60 | 0.0075 | 0.0042 | | 0.0059 | 0.0017 | 2.1 |
| 80 | 0.0000 | 0.0000 | | 0.0000 | 0.0000 | 0.0 |

As an example but not limiting the scope of this invention, is the synthesis and improved DSP inhibition performance for the 1.0:2.0:0.8:0.25 mole ratio TEPA:G:E:EGDGE coupled adduct (sample D) over the performance for the 1.0:2.0:0.8 mole ratio TEPA:G:E uncoupled chemistry (sample C) and 1.0:1.0:0.8 HMDA:G:E (sample 1).

Table 4 provided some data for the improved performance of the coupled adduct sample D over sample C. As a further example, Table 7 shows how the performance for the coupled adducts, as given in Table 3, having 1 to 2 mole ratio of alkoxysilane groups (G) provides better scale inhibition than the uncoupled TEPA:G:E chemistries and 1.0:1.0:0.8 HMDA:G:E (sample 1).

TABLE 7

Enhanced efficacy for the coupled adducts as related to a decrease in net DSP

| Sample | Mass 1, g | Mass 2, g | Mass 3, g | Avg. DSP, g | Std. D. | Net DSP, g | Decrease in Net DSP |
|---|---|---|---|---|---|---|---|
| Control | 0.0575 | 0.0785 | | 0.0680 | 0.0105 | 0.0680 | x |
| Control DSP | 0.3240 | 0.3388 | 0.3778 | 0.3469 | 0.0227 | 0.1469 | 0 |
| 1 | 0.3370 | 0.3190 | | 0.3280 | 0.0090 | 0.1280 | 12.9% |
| A | 0.2726 | 0.2831 | | 0.2779 | 0.0053 | 0.0779 | 47.0% |
| B | 0.2493 | 0.2587 | | 0.2540 | 0.0047 | 0.0540 | 63.2% |
| C | 0.2701 | 0.2828 | | 0.2765 | 0.0063 | 0.0765 | 47.9% |
| D | 0.2382 | 0.2336 | | 0.2359 | 0.0023 | 0.0359 | 75.6% |
| G | 0.3145 | 0.3454 | | 0.3300 | 0.0155 | 0.1300 | 11.5% |
| H | 0.3064 | 0.3192 | | 0.3128 | 0.0064 | 0.1128 | 23.2% |

For example, compare the performance of
sample B versus sample A, and,
sample D versus sample C, and,
sample H versus sample G.

Furthermore, the results from Table 7 indicate that the preferred composition is 2 moles equivalents of alkoxysilane groups G based on the amine compared to 1 mole equivalent of alkoxysilane group G for either the uncoupled or coupled small molecules, for example compare the results for sample C with sample A and sample D with sample B.

Surprisingly, increasing the level of alkoxysilane groups G to greater than two, e.g., three, mole equivalents does not lead to a further enhancement in the DSP scale inhibition performance in contrast to what might be expected. In fact the addition of three equivalents leads to a lower performance than for compounds with only one equivalent of alkoxysilane group G.

Evidence for this is in Table 7, compare the performance of
 the uncoupled sample G versus samples C and A, and,
 EGDGE coupled sample H versus samples D and B Thus, it is postulated that it is not only the presence of the silane that is key to ensure binding of the inhibitor to the DSP seed or nuclei to prevent further growth of the crystal. It is possible that the presence of unhindered amine sites also helps to improve adsorption and scale inhibition. A spatial separation of the silane was achieved in previously disclosed HDA:G:E compounds. The unhindered amine may help to facilitate improved binding of the small molecule to the DSP seed crystal.

Evidence for this is the observed relative differences in the rate of adsorption between these chemistries onto the DSP seed crystals. As an example, Table 8 shows that the new 1.0:2.0:0.8:0.25 mole ratio TEPA:G:E:EGDGE composition (sample D) adsorbs significantly faster to the surface of a DSP seed crystal compared to the 1.0:1.0:0.8 mole ratio HDA:G:E) composition (sample 1).

TABLE 8

Faster adsorption of coupled adducts versus uncoupled chemistries.

| Sample | Contact Time, min | Mass 1, g | Mass 2, g | Mass 3, g | Avg. DSP, g | Std. D. | Net DSP, g | Decrease in Net DSP |
|---|---|---|---|---|---|---|---|---|
| Control | | 0.0427 | 0.0445 | | 0.0436 | 0.0009 | 0.0436 | x |
| ContDSP | | 0.3101 | 0.3033 | 0.3569 | 0.3234 | 0.0238 | 0.1234 | 0 |
| D | 2 | 0.2922 | 0.2895 | | 0.2909 | 0.0013 | 0.0908 | 26.4% |
| D | 5 | 0.2527 | 0.2641 | | 0.2584 | 0.0057 | 0.0584 | 52.9% |
| D | 8 | 0.2219 | 0.2261 | | 0.2240 | 0.0021 | 0.0240 | 83.5% |
| 1 | 2 | 0.3167 | 0.3136 | | 0.3152 | 0.0016 | 0.1152 | 6.6% |
| 1 | 5 | 0.3091 | 0.2871 | | 0.2981 | 0.0110 | 0.0981 | 20.5% |
| 1 | 8 | 0.3000 | 0.3106 | | 0.3053 | 0.0053 | 0.1053 | 14.7% |

Table 9 shows the continuous reduction and complete elimination of DSP scale formation as a function of the applied dosage of the sample D from 0 to 80 ppm as product. Further supporting the improvement over the uncoupled composition complete scale inhibition was found at dosages between 50-60 ppm compared to 80 ppm for sample C (see Table 4).

TABLE 9

Complete inhibition of DSP by sample D

| Dose, ppm | Avg. Mass DSP, g | % DSP Precipitated |
|---|---|---|
| 0 Control | 0.4540 | 100.0% |
| 20 | 0.3015 | 66.4% |
| 30 | 0.1850 | 40.7% |
| 40 | 0.0585 | 12.9% |
| 60 | 0.0000 | 0.0% |
| 80 | 0.0000 | 0.0% |

Tables 10 and 11 provided additional examples of improved performance of the coupled A:G:E adducts over uncoupled A:G:E compositions, for example compare the results for samples E, F, H and J against the corresponding uncoupled samples C, 1, G, and sample 1 (from table 3). Additionally these samples show how the relative scale inhibition performance is influenced by subtle changes in the mole ratio of components E and di-oxirane coupling agent in the compositions. The results indicate that for the uncoupled compositions the preferred amount of the E component is about 0.8 mole ratio. However, for compositions with the coupling agent EGDGE, scale inhibition improves with a slight decrease in component E from about 0.8 to about 0.5 mole ratio when the EGDGE component is increased from a mole ratio of about 0.25 to 0.5.

TABLE 10

Advantages of coupled [Amine:G:E]2-X adducts versus uncoupled Amine:G:E chemistries as related to net DSP

| Sample | Mass 1, g | Mass 2, g | Mass 3, g | Avg. DSP, g | Std. D. | Net DSP, g | Decrease in Net DSP |
|---|---|---|---|---|---|---|---|
| Control | 0.0351 | 0.0323 | | 0.0337 | 0.0014 | 0.0337 | x |
| Control DSP | 0.3093 | 0.3079 | 0.2958 | 0.3043 | 0.0061 | 0.1043 | 0 |
| I | 0.2932 | 0.2898 | | 0.2915 | 0.0017 | 0.0915 | 12.3% |
| J | 0.2544 | 0.2466 | | 0.2505 | 0.0039 | 0.0505 | 51.6% |
| F | 0.2133 | 0.2158 | | 0.2146 | 0.0013 | 0.0146 | 86.1% |
| C | 0.2553 | 0.2634 | | 0.2594 | 0.0040 | 0.0594 | 43.1% |
| D | 0.2276 | 0.2260 | | 0.2268 | 0.0008 | 0.0268 | 74.3% |
| E | 0.2133 | 0.2081 | | 0.2107 | 0.0026 | 0.0107 | 89.7% |

TABLE 11

Advantages of coupled [Amine:G:E]2-X adducts versus uncoupled Amine:G:E chemistries; Additional Examples

| Sample | Mass 1, g | Mass 2, g | Mass 3, g | Avg. DSP, g | Std. D. | Net DSP, g | Decrease in Net DSP |
|---|---|---|---|---|---|---|---|
| Control | 0.0352 | 0.0361 | | 0.0357 | 0.0005 | 0.0357 | x |
| Control DSP | 0.3214 | 0.3291 | 0.3269 | 0.3258 | 0.0032 | 0.1258 | 0 |
| F | 0.2132 | 0.2152 | | 0.2142 | 0.0010 | 0.0142 | 88.7% |
| D | 0.2288 | 0.2345 | | 0.2317 | 0.0029 | 0.0317 | 74.8% |
| D | 0.2421 | 0.2338 | | 0.2380 | 0.0042 | 0.0380 | 69.8% |
| E | 0.2213 | 0.2270 | | 0.2242 | 0.0029 | 0.0241 | 80.8% |

While this invention may be embodied in many different forms, there are shown in the drawings and described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all sub-ranges assumed and subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the illustrated specific embodiments or examples is intended or should be inferred. The disclosure is intended to cover by the appended claims all such modifications as fall within the scope of the claims.

What is claimed is:

1. A method of reducing aluminosilicate containing scale in a Bayer process comprising:

adding to a Bayer process stream upstream from or at a heat exchanger a composition comprising a non-polymeric molecule comprising at least three components, wherein a first component of the at least three components is tetraethylene pentaamine ("TEPA");

a second component of the at least three components is 3-glycidoxypropyltrimethyloxysilane;

and a third component of the at least three components is 2-ethylhexylglycidyl ether;

wherein the composition comprising the non-polymeric molecule is treated with from about 0.2 mole to about 0.5 mole di-oxirane coupling agent per mole of amine present in the non-polymeric molecule, the di-oxirane coupling agent having the structure:

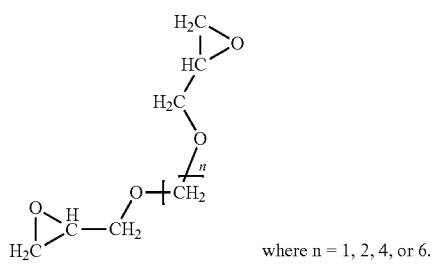

where n = 1, 2, 4, or 6.

2. The method of claim 1, wherein the first component, the second component, and the third component are present in the non-polymeric molecule at a mole ratio ranging from about 1.0:1.0:0.5 to about 1.0:3.0:2.0.

3. The method of claim 1, wherein the first component, the second component, and the third component are present in the non-polymeric molecule at a mole ratio ranging from about 1.0:1.0:0.5 to about 1.0:2.0:1.0.

4. The method of claim 1, wherein the first component, the second component, and the third component are present in the non-polymeric molecule at a mole ratio of about 1.0:2.0:0.8.

5. The method of claim 1, wherein the composition is a solid.

6. The method of claim 1, wherein the non-polymeric molecule is isolated as an unhydrolized alkoxysilane protected with methyl or ethyl ether groups.

7. The method of claim 1, wherein the composition is a gel, a liquid, a solid, or a powder.

8. The method of claim 1, wherein the first component, the second component, the third component, and the di-oxirane coupling agent are present in the composition at a mole ratio ranging from about 1.0:2.0:0.8:0.25 to about 1.0:2.0:0.5:0.5.

9. A method of reducing aluminosilicate containing scale in a Bayer process comprising: adding to a Bayer process stream a non-polymeric molecule having the following structure:

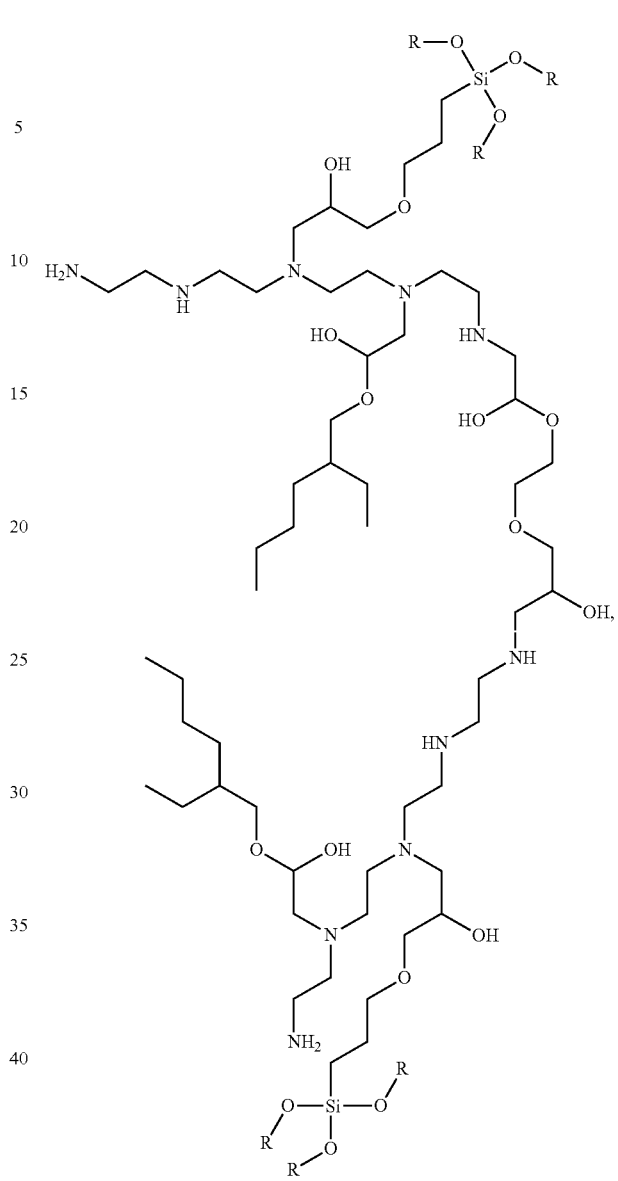

wherein the R-groups are independently selected from the group consisting of: 1-1, alkyl, alkylamine, an inorganic salt, an organic salt, an ether, and an anhydride.

10. The method of claim 1, wherein the composition is added to the Bayer process stream in an amount of from about 20 ppm to about 80 ppm.

11. The method of claim 1, wherein the composition is added to the Bayer process stream in an amount of from about 50 ppm to about 60 ppm.

12. The method of claim 1, wherein the non-polymeric molecule comprises 2 mole equivalents of 3-glycidoxypropyltrimethyloxysilane per 1 mole equivalent of TEPA.

* * * * *

UNITED STATES PATENT AND TRADEMARK OFFICE
CERTIFICATE OF CORRECTION

PATENT NO. : 9,487,408 B2
APPLICATION NO. : 13/403282
DATED : November 8, 2016
INVENTOR(S) : Everett C. Phillips et al.

Page 1 of 1

It is certified that error appears in the above-identified patent and that said Letters Patent is hereby corrected as shown below:

In the Claims

At Column 106, Line 47, please change "I-I" to --H--

Signed and Sealed this
Seventh Day of March, 2017

Michelle K. Lee
*Director of the United States Patent and Trademark Office*